United States Patent
Mackenzie et al.

(10) Patent No.: US 9,476,040 B2
(45) Date of Patent: Oct. 25, 2016

(54) PLANTS WITH USEFUL TRAITS AND RELATED METHODS

(75) Inventors: Sally Ann Mackenzie, Lincoln, NE (US); Roberto De la Rosa Santamaria, Lincoln, NE (US)

(73) Assignee: BOARD OF REGENTS OF THE UNIVERSITY OF NEBRASKA, Lincoln, NE (US)

( * ) Notice: Subject to any disclaimer, the term of this patent is extended or adjusted under 35 U.S.C. 154(b) by 529 days.

(21) Appl. No.: 13/462,216

(22) Filed: May 2, 2012

(65) Prior Publication Data
US 2012/0284814 A1    Nov. 8, 2012

Related U.S. Application Data

(60) Provisional application No. 61/481,519, filed on May 2, 2011, provisional application No. 61/540,236, filed on Sep. 28, 2011.

(51) Int. Cl.
*C12N 15/82* (2006.01)
*C12N 15/113* (2010.01)
*A01H 1/04* (2006.01)

(52) U.S. Cl.
CPC .............. *C12N 15/113* (2013.01); *A01H 1/04* (2013.01); *C12N 15/8218* (2013.01)

(58) Field of Classification Search
USPC ....................................................... 800/278
See application file for complete search history.

(56) References Cited

U.S. PATENT DOCUMENTS

| 2002/0010953 | A1* | 1/2002 | Vliet | .................. | 800/317.4 |
| 2004/0210962 | A1 | 10/2004 | Mackenzie et al. | | |
| 2006/0248613 | A1* | 11/2006 | Mackenzie et al. | .......... | 800/287 |
| 2014/0157452 | A1 | 6/2014 | Mackenzie et al. | | |

FOREIGN PATENT DOCUMENTS

WO    2012/151254 A1    11/2012

OTHER PUBLICATIONS

Sandhu et al., Transgenic induction of mitochondrial rearrangements for cytoplasmic male sterility in crop plants, 104 PNAS, 1766-1770 (2007).*
Boyko et al 2010 (PLOS One 5:3, p. 1-12).*
Molinier et al 2006 (442:31, p. 1046-1049).*
Shedge et al., "Extensive Rearrangement of the Arabidopsis Mitochondrial Genome Elicits Cellular Conditions for Thermotolerance", Plant Physiology, Apr. 2010, pp. 1960-1970, vol. 152, No. 4.
Arrieta-Montiel et al., "Diversity of the Arabidopsis Mitochondrial Genome Occurs via Nuclear-Controlled Recombination Activitiy", Genetics, 2009, pp. 1261-1268, vol. 183.
Davila et al., "Double-Strand Break Repair Processes Drive Evolution of the Mitochondrial Genome in Arabidopsis", BMC Biology: Journal of Biology, 2011, pp. 1-14, vol. 9, No. 64.
Sandhu et al., "Trangenic Induction of Mitochondrial Rearrangements for Cytoplasmic Male Sterility", Proceedings of the National Academy of Sciences, 2007, pp. 1766-1770, vol. 104, No. 6.
Xu et al., "MutS HOMOLOG1 is a Nucleoid Protein that Alters Mitochondrial and Plastid Properties and Plant Responses to High Light", The Plant Cell, 2011, pp. 3428-3441, vol. 23.
Xu et al., "The Chloroplast Triggers Developmental Reprogramming When MUTS HOMOLOG1 is Supressed in Plants", Plant Physiology, 2012, pp. 710-720, vol. 159.
Yang et al., "MSH1-Derived Epigenetic Breeding Potential in Tomato", Plant Physiology Preview, Mar. 3, 2015, 34 pages.
Gao et al., "Analysis of the Leaf Methylomes of Parents and Their Hybrids Provides New Insight Into Hybrid Vigor in Populus Deltoides", BMC Genetics, 2014, 17 pages, vol. 15, Suppl. 1, No. S8.
Santamaria et al., "MSH1-Induced Non-Genetic Variation Provides a Source of Phenotypic Diversity in Sorghum Bicolor", PLOS One, Oct. 2014, 8 pages, vol. 9, Issue 10, e108407.
Shen et al., "Genome-Wide Analysis of DNA Methylation and Gene Expression Changes in Two Arabidopsis Ecotypes and Their Reciprocal Hybrids", The Plant Cell, March 212, pp. 875-892, vol. 24.
Groszmann et al., "The Role of Epigenetics in Hybrid Vigour", Trends in Genetics, Dec. 2013, pp. 684-690, vol. 29 No. 12.
Greaves et al., "Inheritance of Trans Chromosomal Methylation Patterns from Arabidopsis F1 Hybrids", Proceedings of the National Academy of Sciences, Feb. 4, 2014, pp. 2017-2022, vol. 111, No. 5.
Virdi et al., "Arabidopsis MSH1 Mutation Alters the Epigenome and Produces Heritable Changes in Plant Growth", Nature Communications, Feb. 27, 2015, 9 pages.
Dahlgren et al., "Analysis of siRNA Specificity on Targets with Double-Nucleotide Mismatches", Nucleic Acids Research, 2008, pp. 1-7, vol. 36 No. 9.
Du et al., "A Systematic Analysis of the Silencing Effects of an Active siRNA at all Single-Nucleotide Mismatched Target Sites", Nucleic Acids Research, 2005, pp. 1671-1677, vol. 33, No. 5.
Giannelos et al., "Tobacco Seed Oil as an Alternative Diesel Fuel: Physical and Chemical Properties", Industrial Crops and Products, Jul. 2002, pp. 1-9, vol. 16 Issue 1.
Groszmann et al., "Intraspecific Arabidopsis Hybrids Show Different Patterns of Heterosis Despite the Close Relatedness of the Parental Genomes", Plant Physiology, Sep. 2014, pp. 265-280, vol. 166.

(Continued)

*Primary Examiner* — Brent Page
*Assistant Examiner* — Matthew Keogh
(74) *Attorney, Agent, or Firm* — Thompson Coburn LLP; Charles Romano

(57) ABSTRACT

The present invention provides methods for obtaining plants that exhibit useful traits by transient suppression of the MSH1 gene of the plants. Methods for identifying genetic loci that provide for useful traits in plants and plants produced with those loci are also provided. In addition, plants that exhibit the useful traits, parts of the plants including seeds, and products of the plants are provided as well as methods of using the plants.

14 Claims, 21 Drawing Sheets

(56) References Cited

OTHER PUBLICATIONS

Shao et al., "Ws-2 Introgression in a Proportion of Arabidopsis Thaliana Col-0 Stock Seed Produces Specific Phenotypes and Highlights the Importance of Routine Genetic Verification", Department of Agronomy and Horticulture, University of Nebraska, pp. 1-47, manuscript received for publication in the Plant Cell Jan. 26, 2016.

Virdi et al., "Arabidopsis MSH1 Mutation Alters the Epigenome and Produces Heritable Changes in Plant Growth", Nature Communications, Feb. 27, 2015, 23 pages including Supplemental Figures_2015b.

Virdi et al., "MSH1 is a Plant Organellar DNA Binding and Thylakoid Protein under Precise Spatial Regulation to Alter Development", Molecular Plant, 2015, pp. 1-16.

Wesley et al., "Construct Design for Efficient, Effective and High-Throughput Gene Silencing in Plants", The Plant Journal, Sep. 2001, pp. 581-590, vol. 27 Issue 6.

Abdelnoor et al., "Mitochondrial Genome Dynamics in Plants and Animals: Convergent Gene Fusions of a MutS Homologue" J Mol. Evol, Mar. 1, 2006, pp. 165-173, vol. 63.

\* cited by examiner

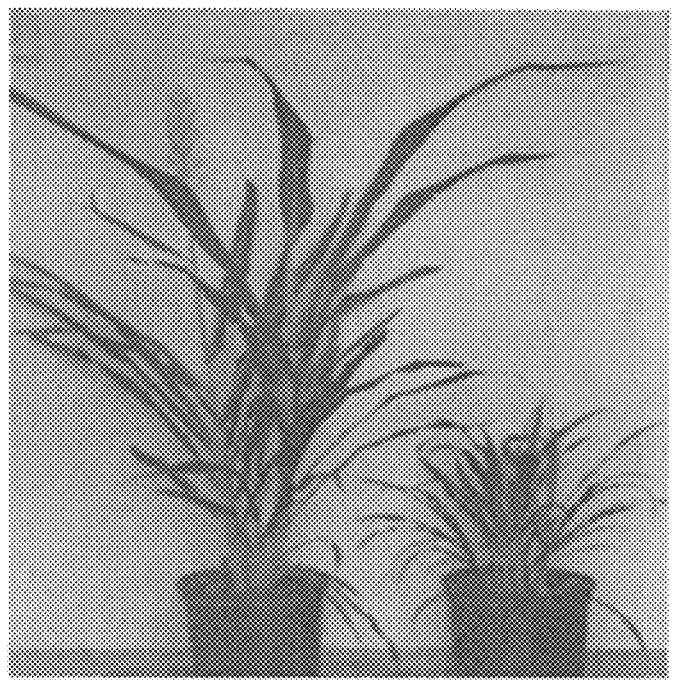
Sorghum
Tomato
FIGURE 3

| Col-0 (wild-type parent) | msh1 x Col-0 F₃ (MSH1 positive progeny) | |
|---|---|---|
| 4.9 | 6.3 | Fresh biomass (g) |
| 2.2 | 2.9 | Base diameter (mm) |
| 1.6 | 2.0 | Stalk diameter (mm) |

FIG. 11 A, B, C, D, E, F, G, H

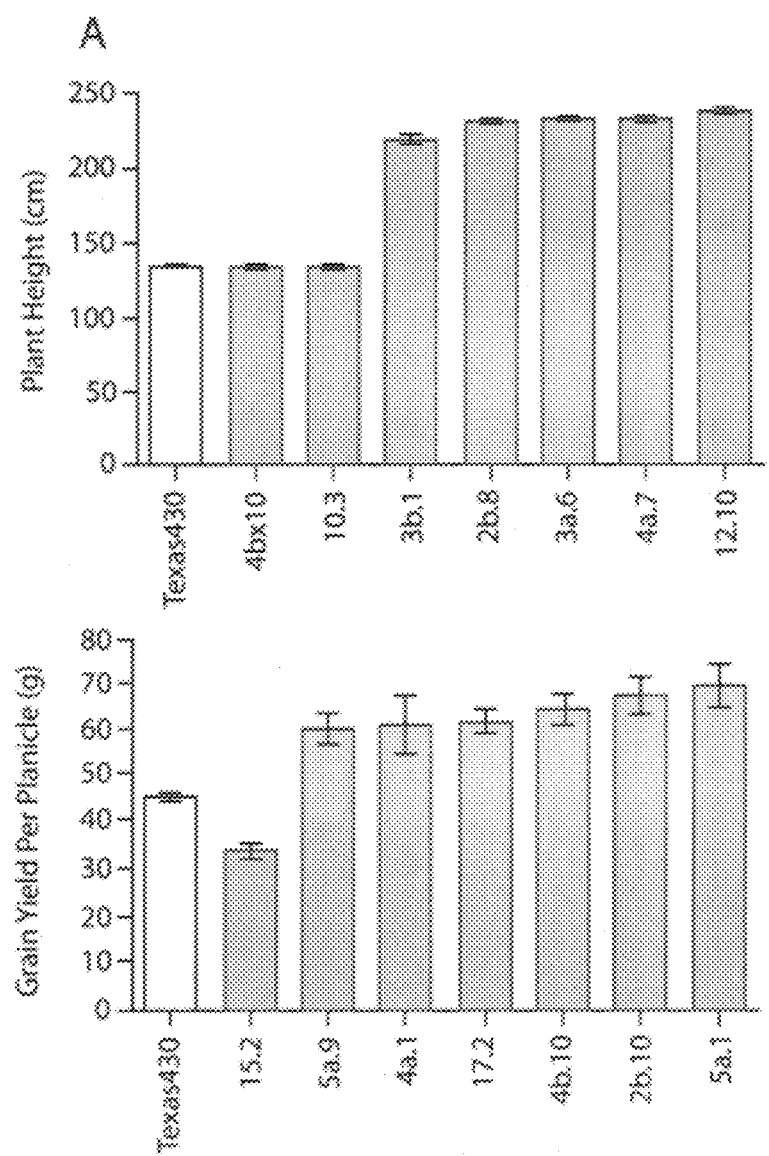
13A

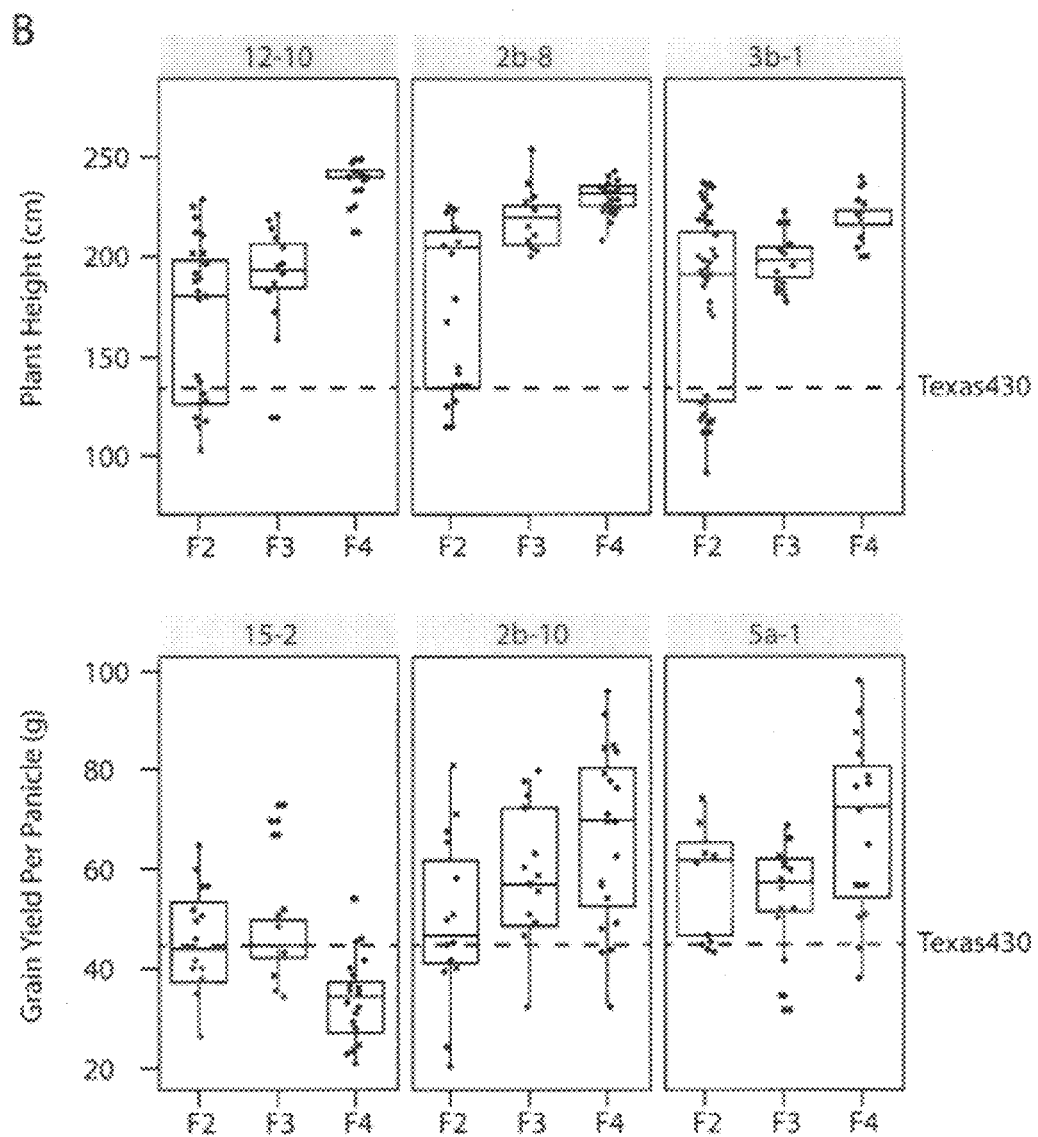
13B

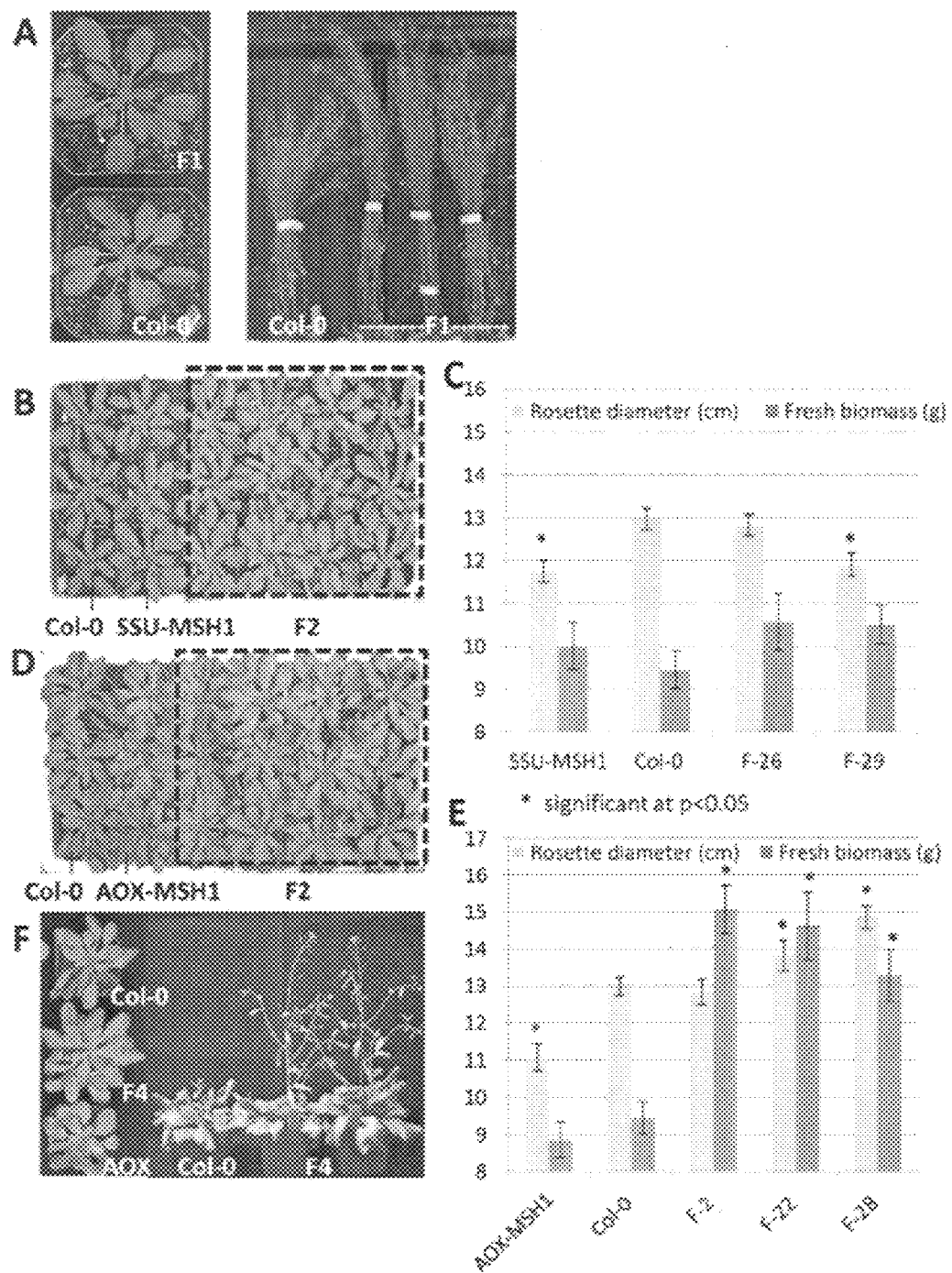
FIG. 14 A, B, C, D, E, F

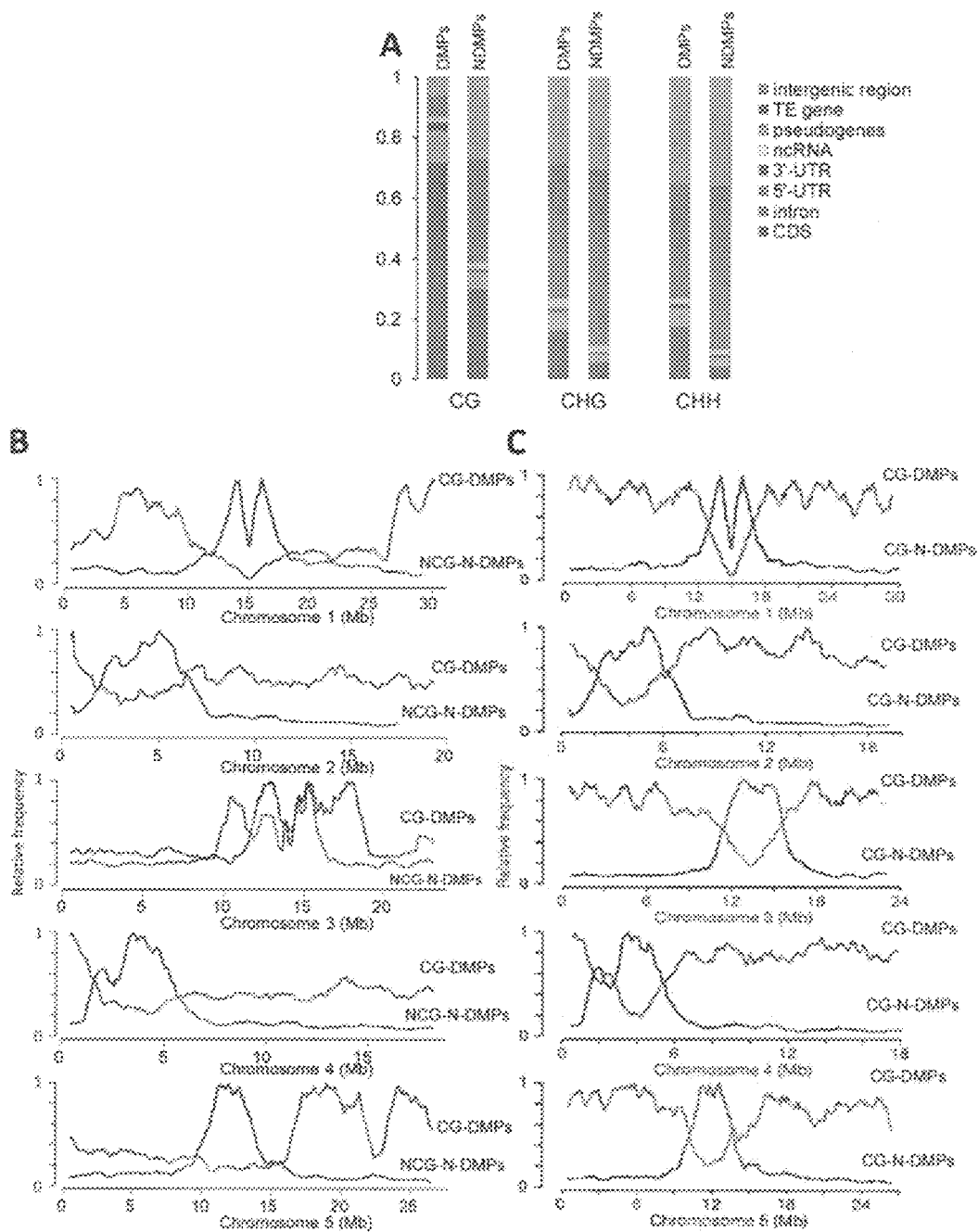
FIGURE 15 A, B, C

PLANTS WITH USEFUL TRAITS AND RELATED METHODS

CROSS-REFERENCE TO RELATED APPLICATIONS

This application claims the benefit under 35 U.S.C. §119(e) of U.S. Provisional Application No. 61/540,236, filed Sep. 28, 2011 and incorporated herein by reference in its entirety, and the benefit under 35 U.S.C. §119(e) of U.S. Provisional Application No. 61/481,519, filed May 2, 2011 and incorporated herein by reference in its entirety.

STATEMENT REGARDING FEDERALLY SPONSORED RESEARCH OR DEVELOPMENT

This invention was made with Government Support under a grant from the Department of Energy (DE-FG02-07ER15564 and DE-FG02-10ER16189) and the National Science Foundation (IOS 0820668 and IOS 1126935). The government has certain rights to this invention.

INCORPORATION OF SEQUENCE LISTING

The sequence listing contained in the file named "46589_103288_SEQ_LST_ST25.txt", which is 75,938 bytes in size (measured in operating system MS-Windows) and was created on May 1, 2012, is contemporaneously filed with this specification by electronic submission (using the United States Patent Office EFS-Web filing system) and is incorporated herein by reference in its entirety.

BACKGROUND OF INVENTION

The MSH1 gene represents a MutS homolog that has undergone at least two important changes in gene structure within land plants (Abdelnoor et al. 2003). MutS is a prokaryotic gene that participates in mismatch repair and suppression of homologous recombination. Consistent with a model of direct protein-DNA interaction, MSH1 encodes not only DNA binding (Domain I) and ATPase (Domain V) domains, but has undergone gene fusion early in its evolution to acquire a carboxy-terminal GIY-YIG type endonuclease domain (Domain VI) (Abdelnoor et al. 2006). The protein has also gained domains II, III, and IV, appearing well-conserved among all land plants. This complexity of gene structure suggests that MSH1 has acquired new functions in plants. While numerous MutS homologs are characterized in eukaryotic lineages, no gene outside of land plants has been found to display the unusual features of MSH1.

MSH1 function has been studied in *Arabidopsis* with MSH1 null (EMS and T-DNA insertion) mutants (i.e. msh1 mutants) and in other plant species by MSH1 RNAi suppression (Sandhu et al. 2007; Xu et al. 2011). What emerged from these studies is that the phenotypic consequences of RNAi suppression are quite similar among species, including leaf variegation, cytoplasmic male sterility (CMS), a reduced growth-rate phenotype, delayed or non-flowering phenotype, and enhanced susceptibility to pathogens. Exposure to heat (Shedge et al. 2010), high light stress (Xu et al. 2011) and other environmental stress conditions (Hruz et al. 2008) result in markedly reduced MSH1 transcript levels.

Initial MSH1 investigations suggested its direct influence on plant mitochondrial genome stability. Null msh1 mutants in *Arabidopsis* display enhanced recombination activity at 47 mitochondrial repeats that, over multiple generations, creates significant genomic rearrangement. A genomic consequence of MSH1 disruption is the process of substoichiometric shifting (SSS) (Arrieta-Montiel et al. 2009). SSS activity produces dramatic changes in relative copy number of parts of the mitochondrial genome, causing selective amplification or suppression of genes residing on affected subgenomes. There are phenotypic consequences to these genomic changes; the SSS process participates in expression of cytoplasmic male sterility (Sandhu et al. 2007), as well as its spontaneous reversion to fertility in natural populations (Janska et al. 1998; Bellaoui et al. 1998; Davila et al. 2011; Mackenzie, 2011). In fact, MSH1 may have played a role in the evolution of gynodioecy as a reproductive strategy in plants (McCauley and Olson, 2008).

Prior to its cloning and identification as a MutS homolog, the MSH1 gene was first named Chloroplast Mutator (CHM) by G. Redei, because its mutation resulted in variegation and altered growth that appeared to derive from chloroplast dysfunction (Redei 1973). In fact, MSH1 encodes a dual targeted protein. A MSH1-GFP transgene fusion protein localizes to both mitochondrial and plastid nucleoids (Xu et al. 2011). The nucleoid is a small, dense protein-RNA-DNA complex that envelopes the organellar genomes. Unlike the mitochondrion however, where recombination is prevalent, no evidence of enhanced chloroplast repeat-mediated recombination is observed in the msh1 mutant. It is possible that MSH1 disruption affects replication features of the plastid genome.

In summary, the effects of MSH1 suppression that have been disclosed in the aforementioned references are limited to effects on plant mitochondria and plastids.

Evidence exists in support of a link between environmental sensing and epigenetic changes in both plants and animals (Bonasio et al., *Science* 330, 612, 2010). Trans-generational heritability of these changes remains a subject of active investigation (Youngson et al. *Annu. Rev. Genom. Human Genet.* 9, 233, 2008). Previous studies have shown that altered methylation patterns are highly heritable over multiple generations and can be incorporated into a quantitative analysis of variation (Vaughn et al. 2007; Zhang et al. 2008; Johannes et al. 2009). Earlier studies of methylation changes in *Arabidopsis* suggest amenability of the epigenome to recurrent selection and also suggest that it is feasible to establish new and stable epigenetic states (F. Johannes et al. *PLoS Genet.* 5, e1000530 (2009); F. Roux et al. *Genetics* 188, 1015 (2011). Manipulation of the *Arabidopsis* met1 and ddmt mutants has allowed the creation of epi-RIL populations that show both heritability of novel methylation patterning and epiallelic segregation, underscoring the likely influence of epigenomic variation in plant adaptation (F. Roux et al. *Genetics* 188, 1015 (2011)). In natural populations, a large proportion of the epiallelic variation detected in *Arabidopsis* is found as CpG methylation within gene-rich regions of the genome (C. Becker et al. *Nature* 480, 245 (2011), R. J. Schmitz et al. *Science* 334, 369 (2011).

SUMMARY OF INVENTION

Methods for producing a plant exhibiting useful traits, methods for identifying one or more altered chromosomal loci in a plant that can confer a useful trait, methods for obtaining plants comprising modified chromosomal loci that can confer a useful trait, plants exhibiting the useful traits, parts of those plants including cells, leafs, stems, flowers and seeds, methods of using the plants and plant parts, and products of those plants and plant parts, including processed products such as a feed or a meal are provided herein.

In certain embodiments, methods for producing a plant exhibiting a useful trait comprising the steps of: a) suppressing expression of MSH1 gene(s) in a first parental plant or plant cell; b) outcrossing the parental plant of step (a), progeny of the parental plant of step (a), a plant obtained from the plant cell of step (a), or progeny of a plant obtained from the plant cell of step (a) to a second plant wherein MSH1 had not been suppressed; c). screening a population of progeny plants obtained from the outcross of step (b) for at least one useful trait, wherein a portion of the population of progeny plants express MSH1; and, d). selecting a progeny plant comprising the trait that expresses MSH1, wherein the trait is heritable and reversible, are provided. In certain embodiments of the methods, the trait is associated with one or more altered chromosomal loci. In certain embodiments, such altered chromosomal loci can comprise loci that are methylated. In certain embodiments, methods for producing a plant exhibiting a useful trait comprising the steps of: a) suppressing expression of MSH1 gene(s) in a first parental plant or plant cell; b) outcrossing the parental plant of step (a), progeny of the parental plant of step (a), a plant obtained from the plant cell of step (a), or progeny of a plant obtained from the plant cell of step (a) to a second plant wherein MSH1 had not been suppressed; c) screening a population of progeny plants obtained from the outcross of step (b) for at least one useful trait, wherein a portion of the population of progeny plants express MSH1; and, d) selecting a progeny plant comprising the trait that expresses MSH1, wherein the trait is associated with one or more mutated chromosomal loci, are provided. In certain embodiments, the mutated chromosomal loci comprise nucleotide inversions, insertions, deletions, substitutions, or combinations thereof. In certain embodiments, the chromosomal loci comprise mutations are reversible. In certain embodiments, the chromosomal loci comprise mutations are irreversible. In certain embodiments of any of the preceding methods, the method further comprises the step of producing seed from: i) a selfed progeny plant of step (d), ii) an out-crossed progeny plant of step (d), or, iii) from both of a selfed and an out-crossed progeny plant of step (d). In certain embodiments, the methods can further comprise the step of assaying seed or plants grown from the seed for the presence of the trait. In certain embodiments of any of the preceding methods, the first parental plant or plant cell comprises a transgene that can suppress expression of MSH1. In certain embodiments of the methods, the transgene is selected from the group of transgenes that suppress expression of MSH1 by producing a small inhibitory RNA (siRNA), a microRNA (miRNA), a co-suppressing sense RNA, and/or an anti-sense RNA. In certain embodiments of any of the preceding methods, the first parental plant or plant cell can be obtained by crossing a female plant with a distinct male plant, wherein at least one of the female or male plants comprise a transgene that suppresses expression of the endogenous MSH1 gene of the parental plant(s), and wherein the plants were isogenic inbred lines prior to introduction of the transgene. In certain embodiments of any of the preceding methods, the first parental plant or plant cell was isogenic to the second parental plant prior to suppression of MSH1 in the first parental plant or plant cell. In certain embodiments of any of the preceding methods the trait is selected from the group consisting of yield, male sterility, non-flowering, resistance to biotic stress, and resistance to abiotic stress. In certain embodiments, abiotic stress can be selected from the group consisting of drought stress, osmotic stress, nitrogen stress, phosphorous stress, mineral stress, heat stress, cold stress, and/or light stress. In certain embodiments, resistance to abiotic stress can include drought tolerance, high light tolerance, heat tolerance, cold tolerance, and salt tolerance. In certain embodiments of the methods, biotic stress can be selected from the group consisting of plant fungal pathogens, plant bacterial pathogens, plant viral pathogens, insects, nematodes, and herbivores, and any combination thereof. In certain embodiments of any of the preceding methods, the trait is not caused by substoichiometric shifting (SSS) in mitochondria of the progeny plant. In certain embodiments of any of the preceding methods, the trait is male sterility and is not caused by substoichiometric shifting (SSS) in mitochondria of the progeny plant. In certain embodiments of any of the preceding methods, the progeny plant in step (d) or progeny thereof exhibit an improvement in the trait in comparison to a plant that had not been subjected to suppression of MSH1 expression but was otherwise isogenic to the first parental plant or plant cell parental plants. In certain embodiments of any of the preceding methods, the plant is a crop plant. In certain embodiments of any of the preceding methods, the crop plant is selected from the group consisting of cotton, canola, wheat, barley, flax, oat, rye, turf grass, sugarcane, alfalfa, banana, broccoli, cabbage, carrot, cassava, cauliflower, celery, citrus, a cucurbit, eucalyptus, garlic, grape, onion, lettuce, pea, peanut, pepper, potato, poplar, pine, sunflower, safflower, soybean, strawberry, sugar beet, sweet potato, tobacco, cassava, cauliflower, celery, citrus, cotton, a cucurbit, eucalyptus, garlic, grape, onion, lettuce, pea, peanut, pepper, potato, poplar, pine, sunflower, safflower, strawberry, sugar beet, sweet potato, tobacco, cassava, cauliflower, celery, citrus, cucurbits, eucalyptus, garlic, grape, onion, lettuce, pea, peanut, pepper, poplar, pine, sunflower, safflower, soybean, strawberry, sugar beet, tobacco, *Jatropha, Camelina*, and *Agave*. In certain embodiments of any of the preceding methods, the crop plant is selected from the group consisting of corn, soybean, cotton, canola, wheat, rice, tomato, tobacco, millet, and sorghum. In certain embodiments of any of the preceding methods, the crop is sorghum. In certain embodiments of any of the preceding methods, the crop is sorghum and the trait is selected from the group consisting of panicle length, panicle weight, dry biomass, and combinations thereof.

Also provided herein are plants, plant parts including seeds, or products of the plants or seeds, that exhibit useful traits caused by alterations and/or mutations in chromosomal loci resulting from suppression of MSH1. In certain embodiments, the plant seed, or products thereof that exhibit useful traits caused by alterations and/or mutations in chromosomal loci resulting from suppression of MSH1 exhibits an improvement in at least one useful trait in comparison to a plant, plant parts including seeds, or products of the plants or seeds, that had not been subjected to suppression of MSH1 expression but was otherwise isogenic to the first parental plant or plant cell. In certain embodiments, such plants, seeds or products of the invention that exhibit useful traits caused by alterations and/or mutations in chromosomal loci resulting from suppression of MSH1 can comprise one or more alterations and/or mutations in one or more chromosomal loci that were induced by MSH1 suppression. In certain embodiments, a plant or a crop plant produced by any of the preceding methods, wherein the crop plant exhibits an improvement in at least one useful trait in comparison to a plant that had not been subjected to suppression of MSH1 expression but was otherwise isogenic to the first parental plant or plant cell is provided. In certain embodiments, any of the aforementioned plants or crop plants is inbred and exhibits an improvement in at least one useful trait in comparison to the parental plant or parental plants. Also provided herein are seed obtained from any of the aforementioned plants or crop plants. Also provided herein are processed products from any of the aforementioned plants, crop plants or seeds, wherein the product comprises a detectable amount of a chromosomal DNA, a mitochondrial DNA, a plastid DNA, plastid and mitochondrial DNA, or any combination thereof. In certain embodiments, the product can comprises a detectable amount of a chromosomal DNA that comprise one or more alterations and/or mutations in one or more chromosomal loci that were induced by MSH1 suppression. In certain embodiments of any of the aforementioned processed products, the product can be oil, meal, lint, hulls, or a pressed cake.

Also provided herein are methods for producing seed that comprise harvesting seed from any of the aforementioned plants or crop plants of the invention. In certain embodiments, methods for producing a lot of seed comprising the steps of selfing a population of plants or crop plants of the invention, growing the selfed plants, and harvesting seed therefrom are provided. In certain embodiments, the harvested seed or a plant obtained therefrom exhibits the improvement in at least one useful trait.

Also provided herewith are methods of using any of the aforementioned plants or crop plants of the invention that comprise any of the improved traits, where the methods comprise growing, propagating, or cultivating the plants or crop plants of the invention that exhibit the improved trait. Methods of obtaining improved yields that comprise harvesting any plant part including a seed of any of the aforementioned plants or crop plants of the invention are also provided. In certain embodiments, the harvested seed or a plant obtained therefrom exhibits the improvement in at least one useful trait.

In certain embodiments, methods for identifying one or more altered chromosomal loci in a plant that can confer a useful trait are provided. In one embodiment, methods comprising the steps of: a. comparing one or more chromosomal regions in a reference plant that does not exhibit the useful trait to one or more corresponding chromosomal regions in a test plant that does exhibit the useful trait, wherein the test plant expresses MSH1 and was obtained from a parental plant or plant cell wherein MSH1 had been suppressed; and, b. selecting for one or more altered chromosomal loci present in the test plant that are absent in the reference plant and that are associated with the useful trait are provided. In certain embodiments, an altered chromosomal locus comprises a chromosomal DNA methylation state, a post-translation modification of a histone protein associated with a chromosomal locus, or any combination thereof. In certain embodiments, the selection comprises isolating a plant or progeny plant comprising the altered chromosomal locus or obtaining a nucleic acid associated with the altered chromosomal locus. In certain embodiments, both the reference plant and the test plant are obtained from a population of progeny plants obtained from a parental plant or plant cell wherein MSH1 had been suppressed. In certain embodiments, both the reference plant and the parental plant or plant cell were isogenic prior to suppression of MSH1 in the parental plant or plant cell. In certain embodiments, the useful trait is selected from the group consisting of yield, male sterility, non-flowering, biotic stress resistance, and abiotic stress resistance. In certain embodiments, abiotic stress can be selected from the group consisting of drought stress, osmotic stress, nitrogen stress, phosphorous stress, mineral stress, heat stress, cold stress, and/or light stress. In certain embodiments, resistance to abiotic stress can include drought tolerance, high light tolerance, heat tolerance, cold tolerance, and salt tolerance. In certain embodiments of the methods, the biotic stress resistance can be selected from the group consisting of plant fungal pathogen resistance, plant bacterial pathogen resistance, plant viral pathogen resistance, insect resistance, nematode resistance, and herbivore resistance, and any combination thereof. In certain embodiments, the useful trait is selected from the group consisting of enhanced lodging resistance, enhanced growth rate, enhanced biomass, enhanced tillering, enhanced branching, delayed flowering time, and delayed senescence. Also provided herein are altered chromosomal loci identified by any of the preceding methods. Such altered chromosomal loci can comprise a chromosomal DNA methylation state, a post-translation modification of a histone protein associated with a chromosomal locus, or any combination thereof.

Also provided herein are plants comprising any of the altered chromosomal loci identified by any of the preceding methods.

Also provided herein are methods for producing a plant exhibiting a useful trait. In certain embodiments, these methods can comprise the steps of: a. introducing a chromosomal modification associated with a useful trait into a plant, wherein the chromosomal modification comprises an altered chromosomal locus induced by MSH1 suppression associated with the useful trait, a transgene that provides for the same genetic effect as an altered chromosomal locus induced by MSH1 suppression associated with the useful trait, or a chromosomal mutation that provides for the same genetic effect as an altered chromosomal locus induced by MSH1 suppression associated with the useful trait; and, b. selecting for a plant that comprises the chromosomal modification and exhibits the useful trait. In certain embodiments, the methods can further comprise the step of producing seed from: i) a selfed progeny plant of the selected plant of step (b), ii) an out-crossed progeny plant of the selected plant of step (b), or, iii) from both of a selfed and an out-crossed progeny plant of the selected plant of step (b). In certain embodiments of the methods, the chromosomal modification can comprise an altered chromosomal locus and the plant is selected by assaying for the presence of a chromosomal DNA methylation state, a post-translation modification of a histone protein associated with a chromosomal locus, or any combination thereof, that is associated with the altered chromosomal locus. In certain embodiments, the chromosomal modification comprises the transgene or the chromosomal mutation and the plant is selected by assaying for the presence of the transgene or the chromosomal mutation. In other embodiments, the plant is selected by assaying for the presence of the useful trait. In certain embodiments, the chromosomal modification comprises an altered chromosomal locus and the altered chromosomal locus comprises a chromosomal DNA methylation state, a post-translation modification of a histone protein associated with a chromosomal locus, or any combination thereof. In certain embodiments, the altered chromosomal locus has a genetic effect that comprises a reduction in expression of a gene and the chromosomal modification comprises a transgene or a chromosomal mutation that provides for a reduction in expression of the gene. In certain embodiments where the altered chromosomal locus has a genetic effect that comprises a reduction in expression of a gene and the chromosomal modification comprises a transgene, the transgene reduces expression of the gene by producing a small inhibitory RNA (siRNA), a microRNA (miRNA), a co-suppressing sense RNA, and/or an anti-sense RNA directed to the gene. In certain embodiments, the altered chromosomal locus has a genetic effect that comprises an increase in expression of a gene and the chromosomal modification comprises a transgene or a chromosomal mutation that provides for an increase in expression of the gene. In certain embodiments of any of the preceding methods, the useful trait is selected from the group consisting of yield, male sterility, non-flowering, biotic stress resistance, and abiotic stress resistance. In certain embodiments, abiotic stress can be selected from the group consisting of drought stress, osmotic stress, nitrogen stress, phosphorous stress, mineral stress, heat stress, cold stress, and/or light stress. In certain embodiments, resistance to abiotic stress can include drought tolerance, high light tolerance, heat tolerance, cold tolerance, and salt tolerance. In certain embodiments of the methods, biotic stress can be selected from the group consisting of plant fungal pathogens, plant bacterial pathogens, plant viral pathogens, insects, nematodes, and herbivores, and any combination thereof. In certain embodiments of the methods, the useful trait is selected from the group consisting of enhanced lodging resistance, enhanced growth rate, enhanced biomass, enhanced tillering, enhanced branching, delayed flowering time, and delayed senescence. Also provided herein are plants made by any of the preceding methods. In certain embodiments of any of the preceding methods, the plant is a crop plant. In certain embodiments of any of the preceding methods, the crop plant is selected from the group consisting of cotton, canola, wheat, barley, flax, oat, rye, turf grass, sugarcane, alfalfa, banana, broccoli, cabbage, carrot, cassava, cauliflower, celery, citrus, a cucurbit, eucalyptus, garlic, grape, onion, lettuce, pea, peanut, pepper, potato, poplar, pine, sunflower, safflower, soybean, strawberry, sugar beet, sweet potato, tobacco, cassava, cauliflower, celery, citrus, cotton, a cucurbit, eucalyptus, garlic, grape, onion, lettuce, pea, peanut, pepper, potato, poplar, pine, sunflower, safflower, strawberry, sugar beet, sweet potato, tobacco, cassava, cauliflower, celery, citrus, cucurbits, eucalyptus, garlic, grape, onion, lettuce, pea, peanut, pepper, poplar, pine, sunflower, safflower, soybean, strawberry, sugar beet, tobacco, *Jatropha, Camelina*, and *Agave*. In certain embodiments of any of the preceding methods, the crop plant is selected from the group consisting of corn, soybean, cotton, canola, wheat, rice, tomato, tobacco, millet, and *sorghum*. In certain embodiments of any of the preceding methods, the crop is *sorghum*. In certain embodiments of any of the preceding methods, the crop is *sorghum* and the trait is selected from the group consisting of panicle length, panicle weight, dry biomass, and combinations thereof.

Also provided herein are plants, plant parts, including but not limited to, seeds, leaves, stems roots, and flowers, or products of the plants, or plant parts including but not limited to seeds, that comprise a chromosomal modification associated with a useful trait or a chromosomal alteration associated with a useful trait. In certain embodiments, the plant part can comprise a non-regenerable plant part or non-regenerable portion of a plant part. In certain embodiments, the products can be processed products that include, but are not limited to, a feed or a meal obtained from a plant part. In certain embodiments, the plants seed, or products thereof that exhibit useful traits caused by a chromosomal modification exhibits an improvement in at least one useful trait in comparison to a plant, plant parts including seeds, or products of the plants or seeds, that do not comprise the chromosomal modification. In certain embodiments, such plants, seeds or products that that exhibit useful traits, can comprise a chromosomal modification that comprises a altered chromosomal locus induced by MSH1 suppression associated with the useful trait, a transgene that provides for the same genetic effect as an altered chromosomal locus induced by MSH1 suppression associated with the useful trait, or a chromosomal mutation that provides for the same genetic effect as an altered chromosomal locus induced by MSH1 suppression associated with the useful trait. In certain embodiments, such plants, plant parts, seeds or products that exhibit useful traits can comprise an altered chromosomal locus that comprises a chromosomal DNA methylation state, a post-translation modification of a histone protein associated with a chromosomal locus, or any combination thereof. In certain embodiments, the altered chromosomal locus that comprises a chromosomal DNA methylation state can comprise a distinguishing portion of the altered chromosomal locus that is not found in plants, plant parts, or plant products that have not been subject to MSH1 supression. In certain embodiments, the distinguishing portion of the altered chromosomal locus can comprise a methylated DNA molecule of at least about 25 nucleotides, 50 nucleotides, 100 nucleotides, 200 nucleotides, 500 nucleotides, or more. In certain embodiments, a plant, plant cell, or plant product produced by any of the preceding methods, wherein the plant exhibits an improvement in at least one useful trait in comparison to a plant that does not comprise the chromosomal alteration but was otherwise isogenic to the first parental plant or plant cell is provided. In certain embodiments, any of the aforementioned plants is inbred and exhibits an improvement in at least one useful trait in comparison to the parental plant or parental plants. Also provided herein are seed obtained from any of the aforementioned plants, plant cells, or crop plants. Also provided herein are processed products from any of the aforementioned plants, crop plants or plant parts including, but not limited to seeds, wherein the product comprises a detectable amount of a chromosomal DNA comprising any of the aforementioned chromosomal modifications that include, but are not limited to, an altered chromosomal locus, a transgene that provides for the same genetic effect as an altered chromosomal locus induced by MSH1 suppression associated with the useful trait, or a chromosomal mutation that provides for the same genetic effect as an altered chromosomal locus induced by MSH1 suppression associated with the useful trait. In certain embodiments of any of the aforementioned processed products, the product can be oil, meal, lint, hulls, or a pressed cake.

Also provided herein are methods for producing seed that comprise harvesting seed from any of the aforementioned plants or crop plants of the invention. In certain embodiments, methods for producing a lot of seed comprising the steps of selfing a population of plants or crop plants of the invention, growing the selfed plants, and harvesting seed therefrom are provided.

Also provided herewith are methods of using any of the aforementioned plants or crop plants of the invention that comprise any of the improved traits, where the methods comprise growing, propagating, or cultivating the plants or crop plants of the invention that exhibit the improved trait. Methods of obtaining improved yields that comprise harvesting any plant part including a seed of any of the aforementioned plants or crop plants of the invention are also provided.

Use in any process of any of the plants, plant parts or portions thereof including but not limited to plant cells, non-regenerable plant parts or portions thereof including but not limited to plant cells, or processed plant products is also provided herein. Processes for which the plants, plant parts or portions thereof, non-regenerable plant parts or portions thereof, or processed plant products provided herein can be used include, but are not limited to, use in breeding, use as biofuel, use as animal feed, use in human food products, and use in any industrial, food, or feed manufacturing processes.

Also provided herein are seed that exhibit the useful trait(s) and plants obtained from the seed that exhibit the improvement in the useful trait(s). In certain embodiments, the seed can comprise an altered chromosomal loci that is associated with the useful trait(s) or that impart the useful trait(s).

In certain embodiments, the plants, plant parts, non-regenerable plant parts, plant cells, non-regenerable plant cells, plant products or processed plant product provided herein can comprise a detectable amount of a chromosomal DNA that comprises an altered chromosomal locus induced by MSH1 suppression associated with the useful trait, a transgene that provides for the same genetic effect as an altered chromosomal locus induced by MSH1 suppression associated with the useful trait, or a chromosomal mutation that provides for the same genetic effect as an altered chromosomal locus induced by MSH1 suppression associated with the useful trait. In certain embodiments, the altered chromosomal locus that comprises a chromosomal DNA methylation state can comprise a distinguishing portion of the altered chromosomal locus that is not found in plants, plant cells, non-regenerable plant cells, plant parts, non-regenerable plant parts, plant products, or processed plant products that have not been subject to MSH1 suppression. In certain embodiments, the distinguishing portion of the altered chromosomal locus can comprise a methylated DNA molecule of at least about 25 nucleotides, 50 nucleotides, 100 nucleotides, 200 nucleotides, 500 nucleotides, or more. Processed products provided herein comprising the chromosomal DNA or distinguishing portions thereof include, but are not limited to, products that comprise oil, meal, lint, hulls, or a pressed cake.

BRIEF DESCRIPTION OF THE DRAWINGS

The accompanying drawings, which are incorporated in and form a part of the specification, illustrate certain embodiments of the present invention. In the drawings:

FIG. 3 illustrates dwarfing in *Sorghum* (top) and tomato (bottom panel) plants that had been subjected to MSH1 suppression.

FIG. 13A, B illustrate phenotypic variation in *sorghum* MSH1-epiF2, F3 and F4 lines. (A) MSH1-epiF4 lines selected for plant height and grain yield per panicle. For plant height, lines 4b-10, 10.3 and 3a.2 were selected for low plant height, all others were selected for tall. For grain yield, line 15.2 was selected for low yield, all others were selected for high. (B) Box plots showing individual population response to selection for four independent populations. Horizontal dashed line represents mean for Tx430 wildtype. In the case of grain yield, F3 selection was carried out in the greenhouse.

FIG. 14A-E illustrates that MSH1-epi enhanced growth in *Arabidopsis* is associated with chloroplast effects. (A) Mitochondrial hemi-complementation line AOX-MSH1×Col-0 F1; (B) Plastid-complemented SSU-MSH1×Col-0 F2 appears identical to Col-0 wildtype, (C) Rosette diameter and fresh biomass of SSU-MSH1-derived F2 lines relative to Col-0; (D) Mitochondrial-complemented AOX-MSH1× Col-0 F2 showing enhanced growth; (E) Rosette diameter and fresh biomass of AOX-MSH1-derived F2 lines is significantly greater (P<0.05) than Col-0. (F) Enhanced growth phenotype in the F4 generation of A0X-MSH1×Col-0.

FIG. 15A-C illustrates Genome-wide 5-methyl-cytosine patterns in *Arabidopsis* Col-0 wildtype and MSH1-epiF3 lines. (A) Relative contributions of CG, CHG and CHH methylation to differential and non-differential methylation of the genome. Note that the intergenic region is at the top of the bar, followed in order by TE gene, pseudogenes, ncRNA, 3'-UTR, 5'-UTR, intron, and CDS. (B) Distribution of CG-DMPs and CG-N-DMPs along each chromosome, with data normalized to the highest value for each chromosome in parallel to the analysis procedure used by Becker et al. *Nature* 480, 245 (2011). (C) Col-0 methylation analysis taken from FIG. 1c in Becker et al. (Ibid) to demonstrate the similarity of NDMP patterns and the dissimilarity of DMP.

Figure 16:
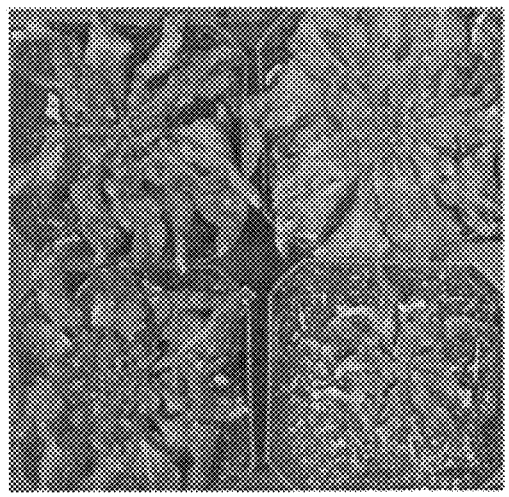

FIG. 16 illustrates *Arabidopsis* F1 plants resulting from crosses of the msh1 chloroplast hemi-complementation line×Col-0 wildtype. Transgene-mediated chloroplast hemi-complementation of msh1 restores the wildtype phenotype. However, crosses of these hemicomplemented lines to Col-0 results in ca. 25% of the plants displaying leaf curl to varying intensities in the F1. The cause of this phenotype is not yet known, but it is no longer visible in derived F2 populations.

Figure 17:
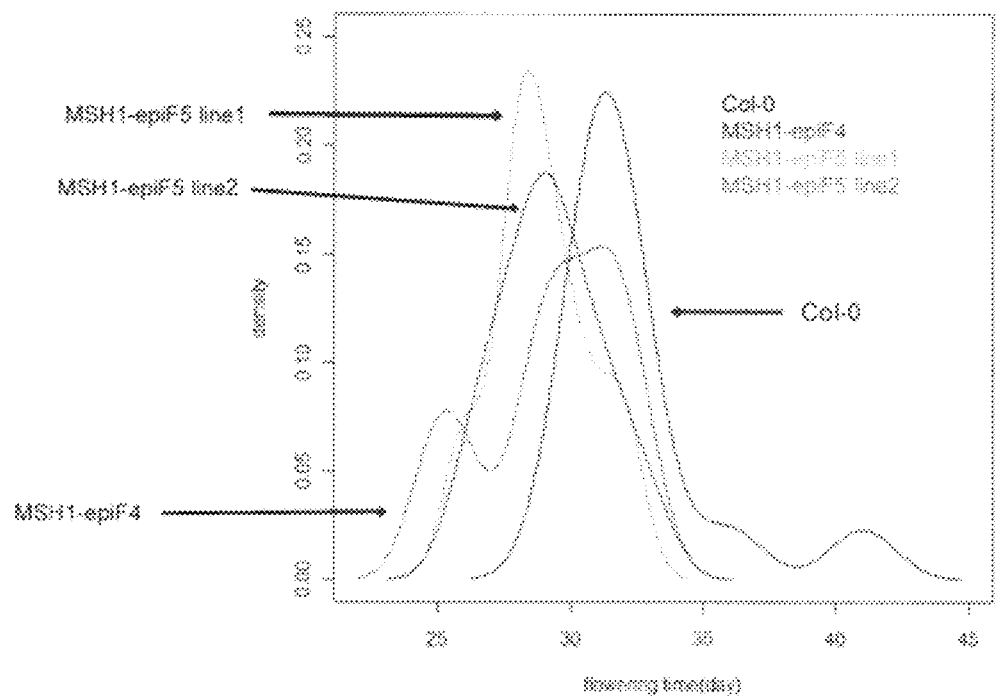

FIG. 17 illustrates the distribution of flowering time in *Arabidopsis* Col-0, epiF4 and epiF5 lines. Each distribution is plotted based on a minimum of 50 plants.

Figure 18A:
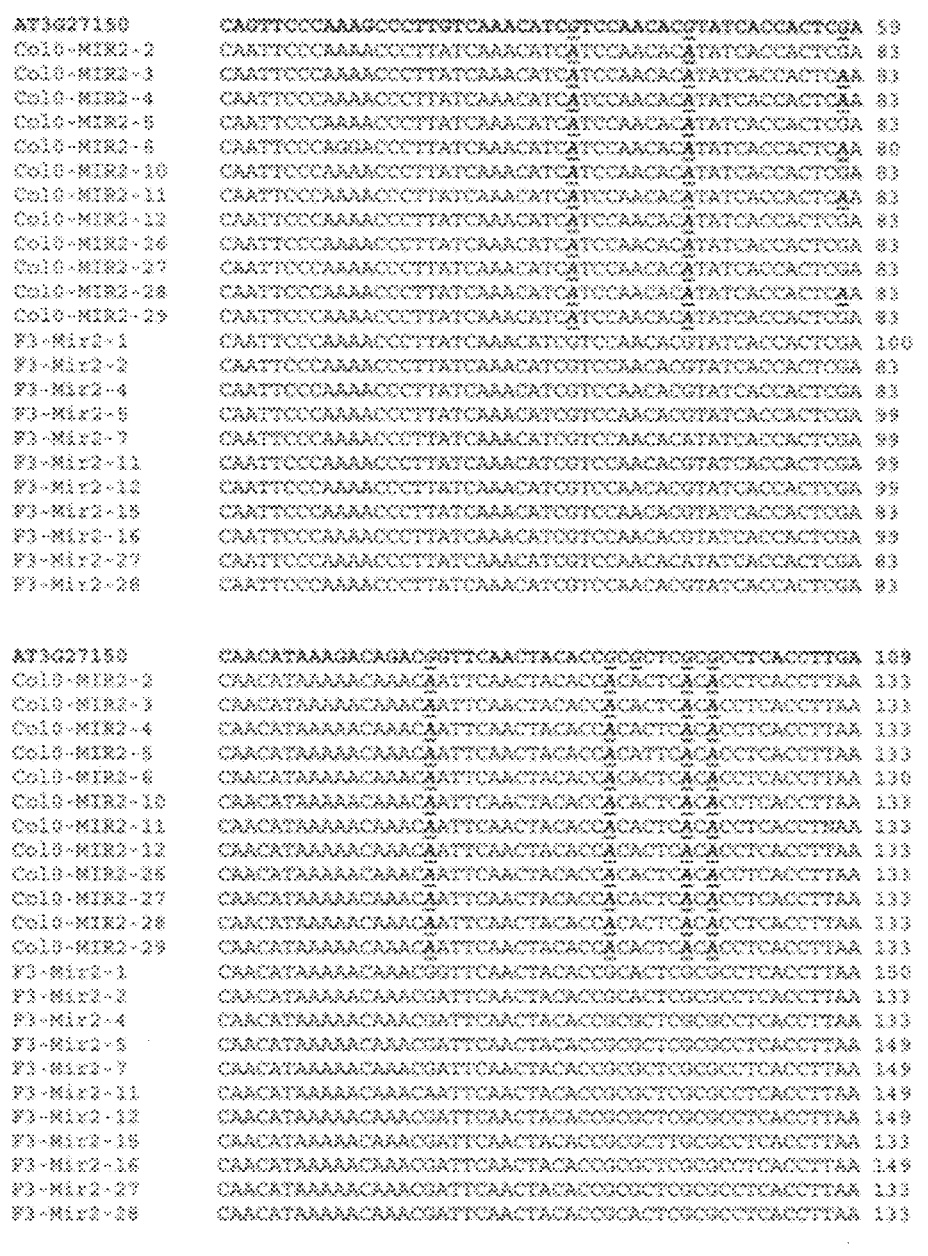

FIG. 18A, B, C illustrates the validation of differentially methylated regions between *arabidopsis* lines col-0 and msh1-epif3 using bisulfate sequencing. Alignment of DMR region within AT3G27150 (Target gene of MIR2111-5p). Highlighted Gs (i.e. underlined in the figure) are predicted to be unmethylated in Col-0 and methylated in MSH1-epiF3. The sequences of FIG. 18A, B, and C are provided in the sequence listing as follows: AT3G27150 (SEQ ID NO:27), Col0-MIR2-2 (SEQ ID NO:28), Col0-MIR2-3 (SEQ ID NO:29), Col0-MIR2-4 (SEQ ID NO:30), Col0-MIR2-5 (SEQ ID NO:31), Col0-MIR2-6 (SEQ ID NO:32), Col0-MIR2-10 (SEQ ID NO:33), Col0-MIR2-11 (SEQ ID NO:34), Col0-MIR2-12 (SEQ ID NO:35), Col0-MIR2-26 (SEQ ID NO:36), Col0-MIR2-27 (SEQ ID NO:37), Col0-MIR2-28 (SEQ ID NO:38), Col0-MIR2-29 (SEQ ID NO:39), F3-Mir2-1 (SEQ ID NO:40), F3-Mir2-2 (SEQ ID NO:41), F3-Mir2-4 (SEQ ID NO:42), F3-Mir2-5 (SEQ ID NO:43), F3-Mir2-7 (SEQ ID NO:44), F3-Mir2-11 (SEQ ID NO:45), F3-Mir2-12 (SEQ ID NO:46), F3-Mir2-15 (SEQ ID NO:47), F3-Mir2-16 (SEQ ID NO:48), F3-Mir2-27 (SEQ ID NO:49), and F3-Mir2-28 (SEQ ID NO:50).

DETAILED DESCRIPTION

I. Definitions

As used herein, the phrase "chromosomal modification" refers to any of: a) an "altered chromosomal loci" and an "altered chromosomal locus"; b) "mutated chromosomal loci", a "mutated chromosomal locus", "chromosomal mutations" and a "chromosomal mutation"; or c) a transgene.

As used herein, the phrases "altered chromosomal loci" (plural) or "altered chromosomal locus (singular) refer to portions of a chromosome that have undergone a heritable and reversible epigenetic change relative to the corresponding parental chromosomal loci. Heritable and reversible changes in altered chromosomal loci include, but are not limited to, methylation of chromosomal DNA, and in particular, methylation of cytosine residues to 5-methylcytosine residues, and/or post-translational modification of histone proteins, and in particular, histone modifications that include, but are not limited to, acetylation, methylation, ubiquitinylation, phosphorylation, and sumoylation (covalent attachment of small ubiquitin-like modifier proteins). As used herein, "chromosomal loci" refer to loci in chromosomes located in the nucleus of a cell.

As used herein, the term "comprising" means "including but not limited to".

As used herein, the phrases "mutated chromosomal loci" (plural) (plural), "mutated chromosomal locus" (singular), "chromosomal mutations" and "chromosomal mutation" refer to portions of a chromosome that have undergone a heritable genetic change in a nucleotide sequence relative to the nucleotide sequence in the corresponding parental chromosomal loci. Mutated chromosomal loci comprise mutations that include, but are not limited to, nucleotide sequence inversions, insertions, deletions, substitutions, or combinations thereof. In certain embodiments, the mutated chromosomal loci can comprise mutations that are reversible. In this context, reversible mutations in the chromosome can include, but are not limited to, insertions of transposable elements, defective transposable elements, and certain inversions. In certain embodiments, the chromosomal loci comprise mutations are irreversible. In this context, irreversible mutations in the chromosome can include, but are not limited to, deletions.

As used herein, the term "discrete variation" or "$V_D$" refers to distinct, heritable phenotypic variation that includes traits of male sterility, dwarfing, variegation, and/or delayed flowering time that can be observed either in any combination or in isolation.

As used herein, the term "MSH-dr" refers to changes in plant tillering, height, internode elongation and stomatal density that are observed in plants subjected to MSH1 suppression.

As used herein, the phrase "quantitative variation" or "$V_Q$" refers to phenotypic variation that is observed in individual progeny lines derived from outcrosses of plants where MSH1 expression was suppressed and that exhibit discrete variation to other plants.

As used herein the terms "microRNA" or "miRNA" refers to both a miRNA that is substantially similar to a native miRNA that occurs in a plant as well as to an artificial miRNA. In certain embodiments, a transgene can be used to produce either a miRNA that is substantially similar to a native miRNA that occurs in a plant or an artificial miRNA.

As used herein, the phrase "obtaining a nucleic acid associated with the altered chromosomal locus" refers to any method that provides for the physical separation or enrichment of the nucleic acid associated with the altered chromosomal locus from covalently linked nucleic that has not been altered. In this context, the nucleic acid does not necessarily comprise the alteration (i.e. such as methylation) but at least comprises one or more of the nucleotide base or bases that are altered. Nucleic acids associated with an altered chromosomal locus can thus be obtained by methods including, but not limited to, molecular cloning, PCR, or direct synthesis based on sequence data.

The phrase "operably linked" as used herein refers to the joining of nucleic acid sequences such that one sequence can provide a required function to a linked sequence. In the context of a promoter, "operably linked" means that the promoter is connected to a sequence of interest such that the transcription of that sequence of interest is controlled and regulated by that promoter. When the sequence of interest encodes a protein and when expression of that protein is desired, "operably linked" means that the promoter is linked to the sequence in such a way that the resulting transcript will be efficiently translated. If the linkage of the promoter to the coding sequence is a transcriptional fusion and expression of the encoded protein is desired, the linkage is made so that the first translational initiation codon in the resulting transcript is the initiation codon of the coding sequence. Alternatively, if the linkage of the promoter to the coding sequence is a translational fusion and expression of the encoded protein is desired, the linkage is made so that the first translational initiation codon contained in the 5' untranslated sequence associated with the promoter is linked such that the resulting translation product is in frame with the translational open reading frame that encodes the protein desired. Nucleic acid sequences that can be operably linked include, but are not limited to, sequences that provide gene expression functions (i.e., gene expression elements such as promoters, 5' untranslated regions, introns, protein coding regions, 3' untranslated regions, polyadenylation sites, and/or transcriptional terminators), sequences that provide DNA transfer and/or integration functions (i.e., site specific recombinase recognition sites, integrase recognition sites), sequences that provide for selective functions (i.e., antibiotic resistance markers, biosynthetic genes), sequences that provide scoreable marker functions (i.e., reporter genes), sequences that facilitate in vitro or in vivo manipulations of the sequences (i.e., polylinker sequences, site specific recombination sequences, homologous recombination sequences), and sequences that provide replication functions (i.e., bacterial origins of replication, autonomous replication sequences, centromeric sequences).

As used herein, the phrase "suppressing expression of MSH1 gene(s)" refers to any genetic or environmental manipulation that provides for decreased levels of functional MSH1 activity in a plant or plant cell relative to the levels of functional MSH1 activity that occur in an otherwise isogenic plant or plant cell that had not been subjected to this genetic or environmental manipulation.

As used herein, the term "transgene", in the context of a chromosomal modification, refers to any DNA from a heterologous source that has been integrated into a chromosome that is stably maintained in a host cell. In this context, heterologous sources for the DNA include, but are not limited to, DNAs from an organism distinct from the host cell organism, species distinct from the host cell species, varieties of the same species that are either distinct varieties or identical varieties, DNA that has been subjected to any in vitro modification, recombinant DNA, and any combination thereof.

As used herein, the term "non-regenerable" refers to a plant part or plant cell that can not give rise to a whole plant.

II. Description Overview

Methods for introducing heritable and epigenetic and/or genetic variation that result in plants that exhibit useful traits are provided herewith along with plants, plant seeds, plant parts, plant cells, and processed plant products obtainable by these methods. In certain embodiments, methods provided herewith can be used to introduce epigenetic and/or genetic variation into varietal or non-hybrid plants that result in useful traits as well as useful plants, plant parts including, but not limited to, seeds, plant cells, and processed plant products that exhibit, carry, or otherwise reflect benefits conferred by the useful traits. In other embodiments, methods provided herewith can be used to introduce epigenetic and/or genetic variation into plants that are also amenable to hybridization.

In most embodiments, methods provided herewith involve suppressing expression of the plant MSH1 gene, restoring expression of a functional plant MSH1 gene, and selecting progeny plants that exhibit one or more useful traits. In certain embodiments, these useful traits are associated with either one or more altered chromosomal loci that have undergone a heritable and reversible epigenetic change, with one or more mutated chromosomal loci that have undergone a heritable genetic change, or combinations thereof.

III. Suppression of MSH1 Expression in Plants or Plant Cells.

In general, methods provided herewith for introducing epigenetic and/or genetic variation plants simply require that MSH1 expression be suppressed for a time sufficient to introduce the variation. As such, a wide variety of MSH 1 suppression methods can be employed to practice the methods provided herewith and the methods are not limited to a particular suppression technique.

Since both the MSH1 gene and the effects of MSH1 gene depletion appear to be highly conserved in plants, it is further anticipated that the methods provided herein can be applied to a variety of different plants or plant cells. Sequences of MSH1 genes or fragments thereof from *Arabidopsis*, soybean, *Zea mays, Sorghum*, rice, *Brachypodium, Vitis vinifera*, cotton, and cucumber are provided herewith. In certain embodiments, such genes may be used directly in either the homologous or a heterologous plant species to provide for suppression of the endogenous MSH1 gene in either the homologous or heterologous plant species. A non-limiting, exemplary demonstration where a MSH1 gene from one species was shown to be effective in suppressing the endogenous MSH1 gene in both a homologous and a heterologous species is provided by Sandhu et al. 2007, where a transgene that provides for an MSH1 inhibitory RNA (RNAi) with tomato MSH1 sequences was shown to inhibit the endogenous MSH1 genes of both tomato and tobacco. A transgene that provides for an MSH1 inhibitory RNA (RNAi) with maize MSH1 sequences can inhibit the endogenous MSH1 genes of millet, *sorghum*, and maize. MSH1 genes from other plants including, but not limited to, cotton, canola, wheat, barley, flax, oat, rye, turf grass, sugarcane, alfalfa, banana, broccoli, cabbage, carrot, cassava, cauliflower, celery, citrus, a cucurbit, eucalyptus, garlic, grape, onion, lettuce, pea, peanut, pepper, potato, poplar, pine, sunflower, safflower, soybean, strawberry, sugar beet, sweet potato, tobacco, cassava, cauliflower, celery, citrus, cotton, a cucurbit, eucalyptus, garlic, grape, onion, lettuce, pea, peanut, pepper, potato, poplar, pine, sunflower, safflower, strawberry, sugar beet, sweet potato, tobacco, cassava, cauliflower, celery, citrus, cucurbits, eucalyptus, garlic, grape, onion, lettuce, pea, peanut, pepper, poplar, pine, sunflower, safflower, soybean, strawberry, sugar beet, tobacco, *Jatropha, Camelina*, and *Agave* can be obtained by a variety of techniques and used to suppress expression of either the corresponding MSH1 gene in those plants or the MSH1 gene in a distinct plant. Methods for obtaining MSH1 genes for various plants include, but are not limited to, techniques such as: i) searching amino acid and/or nucleotide sequence databases comprising sequences from the plant species to identify the MSH1 gene by sequence identity comparisons; ii) cloning the MSH1 gene by either PCR from genomic sequences or RT-PCR from expressed RNA; iii) cloning the MSH1 gene from a genomic or cDNA library using PCR and/or hybridization based techniques; iv) cloning the MSH1 gene from an expression library where an antibody directed to the MSH1 protein is used to identify the MSH1 containing clone; v) cloning the MSH1 gene by complementation of an msh1 mutant or MSH1 deficient plant; or vi) any combination of (i), (ii), (iii), (iv), and/or (v). Recovery of the MSH1 gene from the plant can be readily determined or confirmed by constructing a plant transformation vector that provides for suppression of the gene, transforming the plants with the vector, and determining if plants transformed with the vector exhibit the characteristic responses that are typically observed in various plant species when MSH1 expression is suppressed that include leaf variegation, cytoplasmic male sterility (CMS), a reduced growth-rate phenotype, delayed or non-flowering phenotype, and enhanced susceptibility to pathogens.

In certain embodiments, MSH1 genes or fragments thereof used in the methods provided herein will have nucleotide sequences with at least 50%, 60%, 70%, 80%, 90%, 95%, 98%, 99%, or 100% nucleotide sequence identity to one or more of the MSH1 genes or fragments thereof provided herein that include, but are not limited to, SEQ ID NO:1, SEQ ID NO: 3-10, and SEQ ID NO:14. In certain embodiments, MSH1 genes or fragments thereof used in the methods provided herein encode MSH1 proteins or portions thereof will have amino acid sequences with at least 50%, 60%, 70%, 80%, 90%, 95%, 98%, 99%, or 100% amino acid sequence identity to one or more of the MSH1 proteins provided herein that include, but are not limited to, SEQ ID NO:2, and the MSH1 proteins encoded by SEQ ID NO: 3-10. In certain embodiments, MSH1 genes or fragments thereof used in the methods provided herein will have nucleotide sequences with at least 50%, 60%, 70%, 80%, 90%, 95%, 98%, 99%, or 100% nucleotide sequence identity to one or more of the MSH1 genes fragments thereof, orthologs thereof, or homologs thereof, provided herein that include, but are not limited to, SEQ ID NO:51 and SEQ ID NO:52. In certain embodiments, MSH1 genes or fragments thereof used in the methods provided herein encode MSH1 proteins or portions thereof will have amino acid sequences with at least 50%, 60%, 70%, 80%, 90%, 95%, 98%, 99%, or 100% amino acid sequence identity to one or more of the MSH1 proteins or MSH1 homologs provided herein that include, but are not limited to, the proteins encoded by SEQ ID NO:51 and SEQ ID NO:52. MSH1 genes from plants other than those provided herein can also be identified by the encoded DNA binding (Domain I), ATPase (Domain V), and carboxy-terminal GIY-YIG type endonuclease (Domain VI) domains that characterize many MSH1 genes (Abdelnoor et al. 2006). In this regard, it is anticipated that MSH1 nucleic acid fragments of 18 to 20 nucleotides, but more preferably 21 nucleotides or more, can be used to effect suppression of the endogenous MSH1 gene. In certain embodiments, MSH1 nucleic acid fragments of at least 18, 19, 20, or 21 nucleotides to about 50, 100, 200, 500, or more nucleotides can be used to effect suppression of the endogenous MSH1 gene.

In certain embodiments, suppression of MSH1 in a plant is effected with a transgene. Transgenes that can be used to suppress expression of MSH1 include, but are not limited to, transgenes that produce dominant-negative mutants of MSH1, a small inhibitory RNA (siRNA), a microRNA (miRNA), a co-suppressing sense RNA, and/or an anti-sense RNA that provide for inhibition of the endogenous MSH1 gene. US patents incorporated herein by reference in their entireties that describe suppression of endogenous plant genes by transgenes include U.S. Pat. Nos. 7,109,393, 5,231,020 and 5,283,184 (co-suppression methods); and U.S. Pat. Nos. 5,107,065 and 5,759,829 (antisense methods). In certain embodiments, transgenes specifically designed to produce double-stranded RNA (dsRNA) molecules with homology to the MSH1 gene can be used to decrease expression of the endogenous MSH1 gene. In such embodiments, the sense strand sequences of the dsRNA can be separated from the antisense sequences by a spacer sequence, preferably one that promotes the formation of a dsRNA (double-stranded RNA) molecule. Examples of such spacer sequences include, but are not limited to, those set forth in Wesley et al., Plant J., 27(6):581-90 (2001), and Hamilton et al., Plant J., 15:737-746 (1998). One exemplary and non-limiting vector that has been shown to provide for suppression of MSH1 in tobacco and tomato has been described by Sandhu et al., 2007 where an intron sequence separates the sense and antisense strands of the MSH1 sequence.

In certain embodiments, transgenes that provide for MSH1 suppression can comprise regulated promoters that provide for either induction or down-regulation of operably linked MSH1 inhibitory sequences. In this context, MSH1 inhibitory sequences can include, but are not limited to, dominant-negative mutants of MSH1, a small inhibitory RNA (siRNA), a microRNA (miRNA), a co-suppressing sense RNA, and/or an anti-sense RNA that provide for inhibition of the endogenous MSH1 gene of a plant. Such promoters can provide for suppression of MSH1 during controlled time periods by either providing or withholding the inducer or down regulator. Inducible promoters include, but are not limited to, a PR-1a promoter (US Patent Application Publication Number 20020062502) or a GST II promoter (WO 1990/008826 A1). In other embodiments, both a transcription factor that can be induced or repressed as well as a promoter recognized by that transcription factor and operably linked to the MSH1 inhibitory sequences are provided. Such transcription factor/promoter systems include, but are not limited to: i) RF2a acidic domain-ecdysone receptor transcription factors/cognate promoters that can be induced by methoxyfenozide, tebufenozide, and other compounds (US Patent Application Publication Number 20070298499); ii) chimeric tetracycline repressor transcription factors/cognate chimeric promoters that can be repressed or de-repressed with tetracycline (Gatz, C., et al. (1992). Plant J. 2, 397-404), and the like.

In still other embodiments, transgenic plants are provided where the transgene that provides for MSH1 suppression is flanked by sequences that provide for removal for the transgene. Such sequences include, but are not limited to, transposable element sequences that are acted on by a cognate transposase. Non-limiting examples of such systems that have been used in transgenic plants include the cre-lox and FLP-FRT systems.

MSH1 suppression can be readily identified or monitored by molecular techniques. In certain embodiments where the endogenous MSH1 is intact but its expression is inhibited, production or accumulation of the RNA encoding MSH1 can be monitored. Molecular methods for monitoring MSH1 RNA expression levels include, but are not limited to, use of semi-quantitive or quantitative reverse transcriptase polymerase chain reaction (qRT-PCR) techniques. The use of semi-quantitive PCR techniques to monitor MSH1 suppression resulting from RNAi mediated suppression of MSH1 has been described (Sandhu et al. 2007). Various quantitative RT-PCR procedures including, but not limited to, TaqMan™ reactions (Applied Biosystems, Foster City, Calif. US), use of Scorpion™ or Molecular Beacon™ probes, or any of the methods disclosed in Bustin, S. A. (Journal of Molecular Endocrinology (2002) 29, 23-39) can be used. It is also possible to use other RNA quantitation techniques such as Quantitative Nucleic Acid Sequence Based Amplification (Q-NASBA™) or the Invader™ technology (Third Wave Technologies, Madison, Wis.).

In certain embodiments where MSH1 suppression is achieved by use of a mutation in the endogenous MSH1 gene of a plant, the presence or absence of that mutation in the genomic DNA can be readily determined by a variety of techniques. Certain techniques can also be used that provide for identification of the mutation in a hemizygous state (i.e. where one chromosome carries the mutated msh1 gene and the other chromosome carries the wild type MSH1 gene). Mutations in MSH1 DNA sequences that include insertions, deletions, nucleotide substitutions, and combinations thereof can be detected by a variety of effective methods including, but not limited to, those disclosed in U.S. Pat. Nos. 5,468,613, 5,217,863; 5,210,015; 5,876,930; 6,030,787; 6,004,744; 6,013,431; 5,595,890; 5,762,876; 5,945,283; 5,468,613; 6,090,558; 5,800,944; 5,616,464; 7,312,039; 7,238,476; 7,297,485; 7,282,355; 7,270,981 and 7,250,252 all of which are incorporated herein by reference in their entireties. For example, mutations can be detected by hybridization to allele-specific oligonucleotide (ASO) probes as disclosed in U.S. Pat. Nos. 5,468,613 and 5,217,863. U.S. Pat. No. 5,210,015 discloses detection of annealed oligonucleotides where a 5' labelled nucleotide that is not annealed is released by the 5'-3' exonuclease activity. U.S. Pat. No. 6,004,744 discloses detection of the presence or absence of mutations in DNA through a DNA primer extension reaction. U.S. Pat. No. 5,468,613 discloses allele specific oligonucleotide hybridizations where single or multiple nucleotide variations in nucleic acid sequence can be detected by a process in which the sequence containing the nucleotide variation is amplified, affixed to a support and exposed to a labeled sequence-specific oligonucleotide probe. Mutations can also be detected by probe ligation methods as disclosed in U.S. Pat. No. 5,800,944 where sequence of interest is amplified and hybridized to probes followed by ligation to detect a labeled part of the probe. U.S. Pat. Nos. 6,613,509 and 6,503,710, and references found therein provide methods for identifying mutations with mass spectroscopy. These various methods of identifying mutations are intended to be exemplary rather than limiting as the methods of the present invention can be used in conjunction with any polymorphism typing method to identify the presence of absence of mutations in an MSH1 gene in genomic DNA samples. Furthermore, genomic DNA samples used can include, but are not limited to, genomic DNA isolated directly from a plant, cloned genomic DNA, or amplified genomic DNA.

Mutations in endogenous plant MSH1 genes can be obtained from a variety of sources and by a variety of techniques. A homologous replacement sequence containing one or more loss of function mutations in the MSH1 gene and homologous sequences at both ends of the double stranded break can provide for homologous recombination and substitution of the resident wild-type MSH1 sequence in the chromosome with a msh1 replacement sequence with the loss of function mutation(s). Such loss of function mutations include, but are not limited to, insertions, deletions, and substitutions of sequences within an MSH1 gene that result in either a complete loss of MSH1 function or a loss of MSH1 function sufficient to elicit alterations (i.e. heritable and reversible epigenetic changes) in other chromosomal loci or mutations in other chromosomal loci. Loss-of-function mutations in MSH1 include, but are not limited to, frameshift mutations, pre-mature translational stop codon insertions, deletions of one or more functional domains that include, but are not limited to, a DNA binding (Domain I), an ATPase (Domain V) domain, and/or a carboxy-terminal GIY-YIG type endonuclease domain, and the like. Also provided herein are mutations analogous the *Arabidopsis* msh1 mutation that are engineered into endogenous MSH1 plant gene to obtain similar effects. Methods for substituting endogenous chromosomal sequences by homologous double stranded break repair have been reported in tobacco and maize (Wright et al., Plant J. 44, 693, 2005; D'Halluin, et al., Plant Biotech. J. 6:93, 2008). A homologous replacement msh1 sequence (i.e. which provides a loss of function mutation in an MSH1 sequence) can also be introduced into a targeted nuclease cleavage site by non-homologous end joining or a combination of non-homologous end joining and homologous recombination (reviewed in Puchta, J. Exp. Bot. 56, 1, 2005; Wright et al., Plant J. 44, 693, 2005). In certain embodiments, at least one site specific double stranded break can be introduced into the endogenous MSH1 gene by a meganuclease. Genetic modification of meganucleases can provide for meganucleases that cut within a recognition sequence that exactly matches or is closely related to specific endogenous MSH1 target sequence (WO/06097853A1, WO/06097784A1, WO/04067736A2, U.S. 20070117128A1). It is thus anticipated that one can select or design a nuclease that will cut within a target MSH1 sequence. In other embodiments, at least one site specific double stranded break can be introduced in the endogenous MSH1 target sequence with a zinc finger nuclease. The use of engineered zinc finger nuclease to provide homologous recombination in plants has also been disclosed (WO 03/080809, WO 05/014791, WO 07014275, WO 08/021207). In still other embodiments, mutations in endogenous MSH1 genes can be identified through use of the TILLING technology (Targeting Induced Local Lesions in Genomes) as described by Henikoff et al. where traditional chemical mutagenesis would be followed by high-throughput screening to identify plants comprising point mutations or other mutations in the endogenous MSH1 gene (Henikoff et al., Plant Physiol. 2004, 135:630-636).

In certain embodiments, MSH1 suppression can be effected by exposing whole plants, or reproductive structures of plants, to stress conditions that result in suppression of endogenous MSH1 gene. Such stress conditions include, but are not limited to, high light stress, and heat stress. Exemplary and non-limiting high light stress conditions include continuous exposure to about 300 to about 1200 µmol photons/m2.s for about 24 to about 120 hours. Exemplary and non-limiting heat stress conditions include continuous exposure to temperatures of about 32° C. to about 37° C. for about 2 hours to about 24 hours. Exemplary and non-limiting heat, light, and other environmental stress conditions also that can provide for MSH1 suppression are also disclosed for heat (Shedge et al. 2010), high light stress (Xu et al. 2011) and other environmental stress conditions (Hruz et al. 2008).

Methods where MSH1 suppression is effected in cultured plant cells are also provided herein. In certain embodiments, MSH1 suppression can be effected by culturing plant cells under stress conditions that result in suppression of endogenous MSH1 gene. Such stress conditions include, but are not limited to, high light stress. Exemplary and non-limiting high light stress conditions include continuous exposure to about 300 to about 1200 µmol photons/m2.s for about 24 to about 120 hours. Exemplary and non-limiting heat stress conditions include continuous exposure to temperatures of about 32° C. to about 37° C. for about 2 hours to about 24 hours. Exemplary and non-limiting heat, light, and other environmental stress conditions also that can provide for MSH1 suppression are also disclosed for heat (Shedge et al. 2010), high light stress (Xu et al. 2011) and other environmental stress conditions (Hruz et al. 2008). In certain embodiments, MSH1 suppression is effected in cultured plant cells by introducing a nucleic acid that provides for such suppression into the plant cells. Nucleic acids that can be used to provide for suppression of MSH1 in cultured plant cells include, but are not limited to, transgenes that produce a small inhibitory RNA (siRNA), a microRNA (miRNA), a co-suppressing sense RNA, and/or an anti-sense RNA directed to the MSH1 gene. Nucleic acids that can be used to provide for suppression of MSH1 in cultured plant cells include, but are not limited to, a small inhibitory RNA (siRNA) or a microRNA (miRNA) directed against the endogenous MSH1 gene. RNA molecules that provide for inhibition of MSH1 can be introduced by electroporation. Introduction of inhibitory RNAs to cultured plant cells to inhibit target genes can in certain embodiments be accomplished as disclosed in Vanitharani et al. (Proc Natl Acad Sci USA., 2003, 100(16):9632-6), Qi et al. (Nucleic Acids Res. 2004 Dec. 15;32(22):e179), or J. Cheon et al. (Microbiol. Biotechnol. (2009), 19(8), 781-786).

Figure 1:
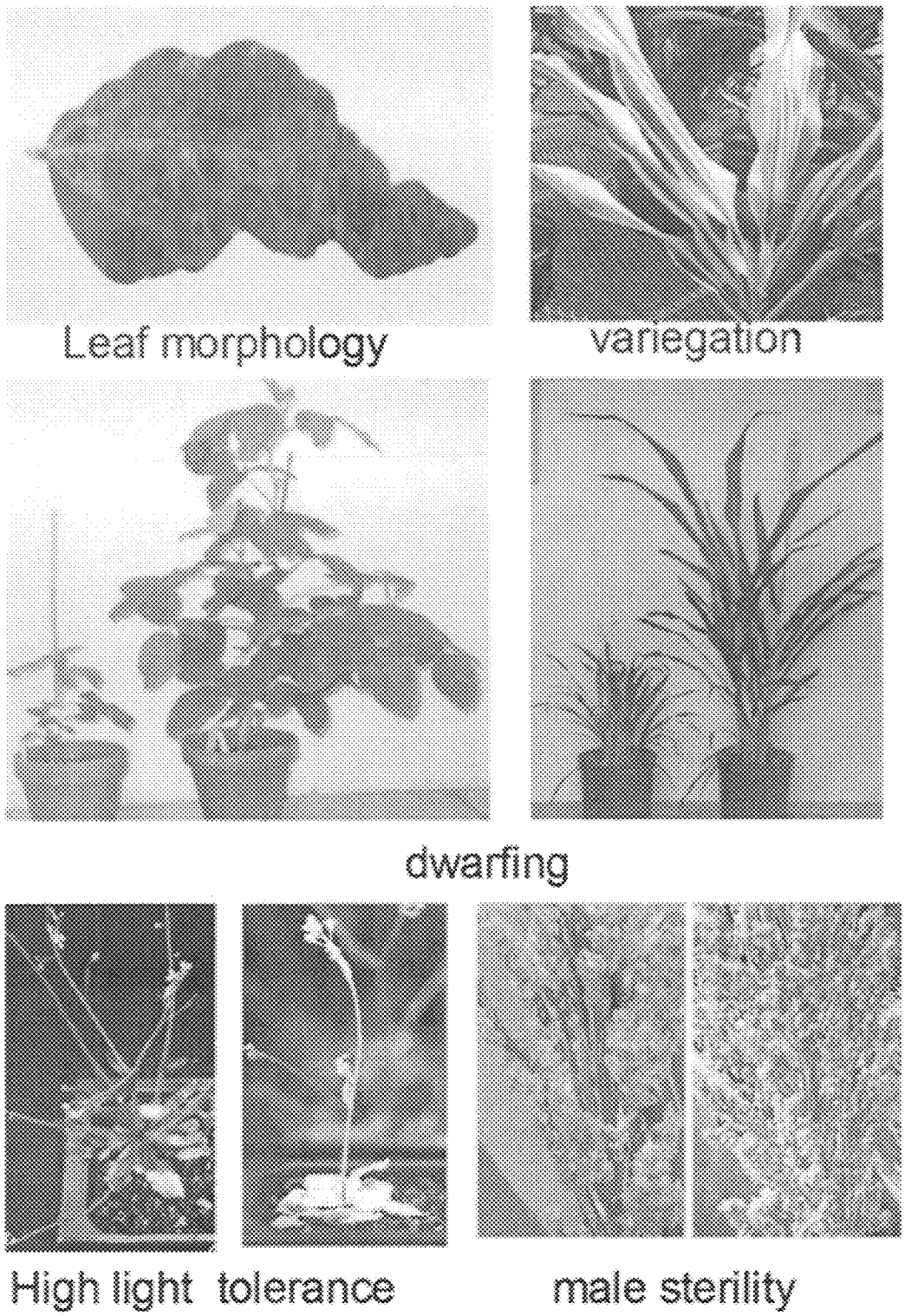
FIG. 1 illustrates various phenotypes that are observed in various plants subjected to MSH1 suppression such as cytoplasmic male sterility, variegation and altered chloroplast development, reduced growth rate and dwarfing, altered flowering time or non-flowering, reduced flavonoid biosynthesis and lack of anthocyanins, enhanced pathogen susceptibility, altered leaf morphologies, and high light tolerance.
Figure 2:
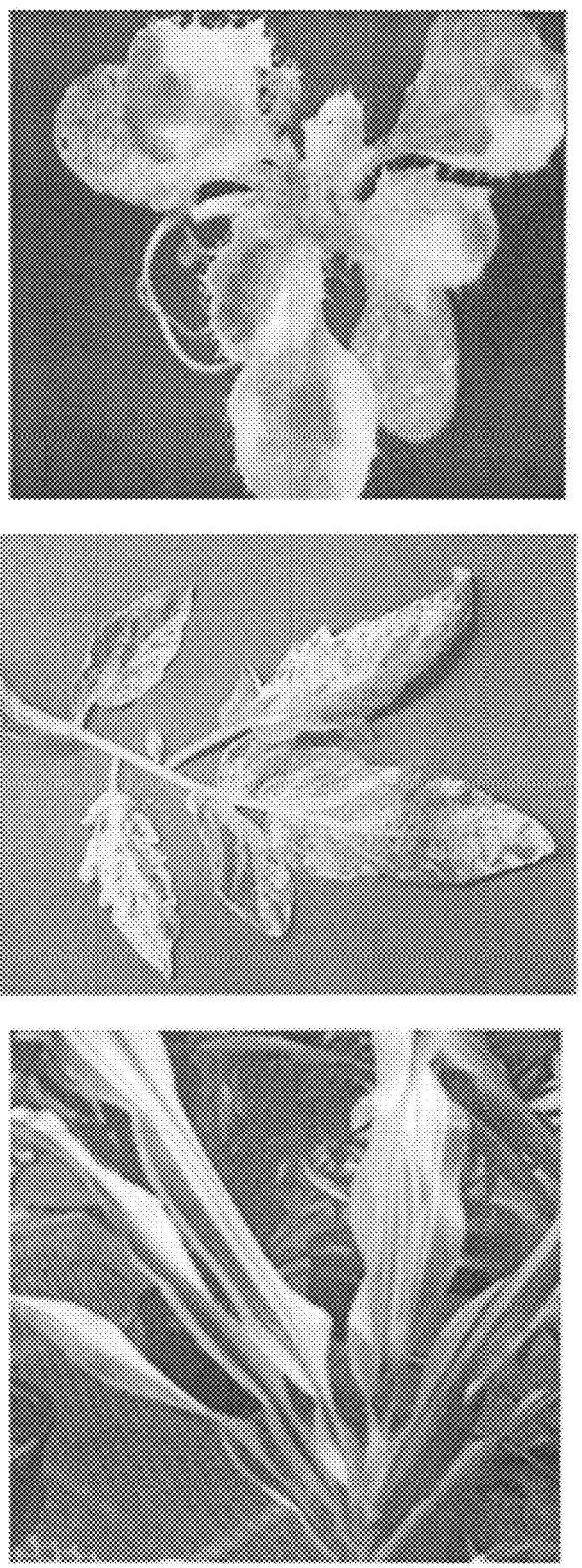
FIG. 2 illustrates leaf variegation in *Arabidopsis* (top), tomato (middle), and *sorghum* (bottom panel) plants that had been subjected to MSH1 suppression.

MSH1 suppression can also be readily identified or monitored by traditional methods where plant phenotypes are observed. For example, MSH1 suppression can be identified or monitored by observing organellar effects that include leaf variegation, cytoplasmic male sterility (CMS), a reduced growth-rate phenotype, delayed or non-flowering phenotype, and/or enhanced susceptibility to pathogens. Phenotypes indicative of MSH1 suppression in various plants are shown in FIGS. 1, 2, and 3. These phenotypes that are associated with MSH1 suppression are referred to herein as "discrete variation" ($V_D$). MSH1 suppression can also produce changes in plant tillering, height, internode elongation and stomatal density (referred to herein as "MSH1-dr") that can be used to identify or monitor MSH1 suppression in plants. Other biochemical and molecular traits can also be used to identify or monitor MSH1 suppression in plants MSH1 suppression. Such molecular traits can include, but are not limited to, changes in expression of genes involved in cell cycle regulation, Giberrellic acid catabolism, auxin biosynthesis, auxin receptor expression, flower and vernalization regulators (i.e. increased FLC and decreased SOC1 expression), as well as increased miR156 and decreased miR172 levels. Such biochemical traits can include, but are not limited to, up-regulation of most compounds of the TCA, NAD and carbohydrate metabolic pathways, down-regulation of amino acid biosynthesis, depletion of sucrose in certain plants, increases in sugars or sugar alcohols in certain plants, as well as increases in ascorbate, alphatocopherols, and stress-responsive flavones apigenin, and apigenin-7-oglucoside. isovitexin, kaempferol 3-O-beta-glucoside, luteolin-7-O-glucoside, and vitexin. It is further contemplated that in certain embodiments, a combination of both molecular, biochemical, and traditional methods can be used to identify or monitor MSH1 suppression in plants.

IV. Recovery, Selfing, and Outcrossing of Progeny of MSH1 Suppressed Plants

A variety of methods that provide for suppression of MSH1 in a plant followed by recovery of progeny plants where MSH1 function is restored are provided herein. In certain embodiments, such progeny plants can be recovered by downregulating expression of an MSH1-inhibiting transgene or by removing the MSH1-inhibiting transgene with a transposase. In certain embodiments of the methods provided herein, MSH1 is suppressed in a target plant or plant cell and progeny plants that express MSH1 are recovered by traditional genetic techniques. In one exemplary and non-limiting embodiment, progeny plants can be obtained by selfing a plant that is heterozygous for the transgene that provides for MSH1 segregation. Selfing of such heterozygous plants (or selfing of heterozygous plants regenerated from plant cells) provides for the transgene to segregate out of a subset of the progeny plant population. Where MSH1 is suppressed by use of a recessive mutation in an endogenous MSH1 gene (i.e. an msh1 plant), msh1/msh1 plants can, in yet another exemplary and non-limiting embodiment, be crossed to MSH1 plants and then selfed to obtain progeny plants that are homozygous for a functional, wild-type MSH1 allele. In other embodiments, MSH1 is suppressed in a target plant or plant cell and progeny plants that express MSH1 are recovered by molecular genetic techniques. Non limiting and exemplary embodiments of such molecular genetic techniques include: i) downregulation of an MSH1 suppressing transgene under the control of a regulated promoter by withdrawal of an inducer required for activity of that promoter or introduction of a repressor of that promoter; or, ii) exposure of the an MSH1 suppressing transgene flanked by transposase recognition sites to the cognate transposase that provides for removal of that transgene.

In certain embodiments of the methods provided herein, progeny plants derived from plants where MSH1 expression was suppressed that exhibit male sterility, dwarfing, variegation, and/or delayed flowering time and express functional MSH1 are obtained and maintained as independent breeding lines. It has been found that such phenotypes appear to sort, so that it is feasible to select a cytoplasmic male sterile plant displaying normal growth rate and no variegation, for example, or a stunted, male fertile plant that is highly variegated. We refer to this phenomenon herein as discrete variation ($V_D$). An exemplary and non-limiting illustration of this phenomenon as it occurs in selfed plant populations that have lost an MSH1-inhibiting transgene by segregation is provided in FIG. 6. It is further contemplated that such individual lines that exhibit discrete variation ($V_D$) can be obtained by any of the aforementioned traditional genetic techniques, molecular genetic techniques, or combinations thereof.

Individual lines obtained from plants where MSH1 expression was suppressed that exhibit discrete variation ($V_D$) can be crossed to other plants to obtain progeny plants that lack the phenotypes associated with discrete variation ($V_D$) (i.e. male sterility, dwarfing, variegation, and/or delayed flowering time). It has surprisingly been found that progeny of such outcrosses can be selfed to obtain individual progeny lines that exhibit significant phenotypic variation. Such phenotypic variation that is observed in these individual progeny lines derived from outcrosses of plants where MSH1 expression was suppressed and that exhibit discrete variation to other plants is herein referred to as "quantitative variation" ($V_Q$). Certain individual progeny plant lines obtained from the outcrosses of plants where MSH1 expression was suppressed to other plants can exhibit useful phenotypic variation where one or more traits are improved relative to either parental line and can be selected. Useful phenotypic variation that can be selected in such individual progeny lines includes, but is not limited to, increases in fresh and dry weight biomass relative to either parental line. An exemplary and non-limiting illustration of this phenomenon as it occurs in F2 progeny of outcrosses of plants that exhibit discrete variation to plants that do not exhibit discrete variation is provided in FIG. 6.

In certain embodiments, an outcross of an individual line exhibiting discrete variability can be to a plant that has not been subjected to MSH1 suppression but is otherwise isogenic to the individual line exhibiting discrete variation. In certain exemplary embodiments, a line exhibiting discrete variation is obtained by suppressing MSH1 in a given germplasm and can outcrossed to a plant having that same germplasm that was not subjected to MSH1 suppression. In other embodiments, an outcross of an individual line exhibiting discrete variability can be to a plant that has not been subjected to MSH1 suppression but is not isogenic to the individual line exhibiting discrete variation. Thus, in certain embodiments, an outcross of an individual line exhibiting discrete variability can also be to a plant that comprises one or more chromosomal polymorphisms that do not occur in the individual line exhibiting discrete variability, to a plant derived from partially or wholly different germplasm, or to a plant of a different heterotic group (in instances where such distinct heterotic groups exist). It is also recognized that such an outcross can be made in either direction. Thus, an individual line exhibiting discrete variability can be used as either a pollen donor or a pollen recipient to a plant that has not been subjected to MSH1 suppression in such outcrosses. In certain embodiments, the progeny of the outcross are then selfed to establish individual lines that can be separately screened to identify lines with improved traits relative to parental lines. Such individual lines that exhibit the improved traits are then selected and can be propagated by further selfing. An exemplary and non-limiting illustration of this procedure where F2 progeny of outcrosses of plants that exhibit discrete variation to plants that do not exhibit discrete variation are obtained is provided in FIG. 6. Such F2 progeny lines are screened for desired trait improvements relative to the parental plants and lines exhibiting such improvements are selected.

V. Comparing and Selecting Altered Chromosomal Loci in Plants that can Confer a Useful Trait Altered chromosomal loci that can confer useful traits can also be identified and selected by performing appropriate comparative analyses of reference plants that do not exhibit the useful traits and test plants obtained from a parental plant or plant cell that had been subjected to MSH1 suppression and obtaining either the altered loci or plants comprising the altered loci. It is anticipated that a variety of reference plants and test plants can be used in such comparisons and selections. In certain embodiments, the reference plants that do not exhibit the useful trait include, but are not limited to, any of: a) a wild-type plant; b) a distinct subpopulation of plants within a given F2 population of plants of a given plant line (where the F2 population is any applicable plant type or variety obtained in the manner shown in FIG. 6); c) an F1 population exhibiting a wild type phenotype (where the F1 population is any applicable plant type or variety obtained in the manner shown in FIG. 6); and/or, d) a plant that is isogenic to the parent plants or parental cells of the test plants prior to suppression of MSH1 in those parental plants or parental cells (i.e. the reference plant is isogenic to the plants or plant cells that were later subjected to MSH1 suppression to obtain the test plants). In certain embodiments, the test plants that exhibit the useful trait include, but are not limited to, any of: a) any non-transgenic segregants that exhibit the useful trait and that were derived from parental plants or plant cells that had been subjected to transgene mediated MSH1 suppression, b) a distinct subpopulation of plants within a given F2 population of plants of a given plant line that exhibit the useful trait (where the F2 population is any applicable plant type or variety obtained in the manner shown in FIG. 6); (c) any progeny plants obtained from the plants of (a) or (b) that exhibit the useful trait; or d) a plant or plant cell that had been subjected to MSH1 suppression that exhibit the useful trait.

In general, an objective of these comparisons is to identify differences in the small RNA profiles and/or methylation of certain chromosomal DNA loci between test plants that exhibit the useful traits and reference plants that do not exhibit the useful traits. Altered loci thus identified can then be isolated or selected in plants to obtain plants exhibiting the useful traits.

In certain embodiments, altered chromosomal loci can be identified by identifying small RNAs that are up or down regulated in the test plants (in comparison to reference plants). This method is based in part on identification of altered chromosomal loci where small interfering RNAs direct the methylation of specific gene targets by RNA-directed DNA methylation (RdDM). The RNA-directed DNA methylation (RdDM) process has been described (Chinnusamy V et al. Sci China Ser C-Life Sci. (2009) 52(4): 331-343). Any applicable technology platform can be used to compare small RNAs in the test and reference plants, including, but not limited to, microarray-based methods (Franco-Zorilla et al. Plant J. 2009 59(5):840-50), deep sequencing based methods (Wang et al. The Plant Cell 21:1053-1069 (2009)), and the like.

In certain embodiments, altered chromosomal loci can be identified by identifying histone proteins associated with a locus and that are methylated or acylated in the test plants (in comparison to reference plants). The analysis of chromosomal loci associated with methylated or acylated histones can be accomplished by enriching and sequencing those loci using antibodies that recognize methylated or acylated histones. Identification of chromosomal regions associated with methylation or acetylation of specific lysine residues of histone H3 by using antibodies specific for H3K4me3, H3K9ac, H3K27me3, and H3K36me3 has been described (Li et al., Plant Cell 20:259-276, 2008; Wang et al. The Plant Cell 21:1053-1069 (2009).

In certain embodiments, altered chromosomal loci can be identified by identifying chromosomal regions (genomic DNA) that has an altered methylation status in the test plants (in comparison to reference plants). An altered methylation status can comprise either the presence or absence of methylation in one or more chromosomal loci of a test plant comparison to a reference plant. Any applicable technology platform can be used to compare the methylation status of chromosomal loci in the test and reference plants. Applicable technologies for identifying chromosomal loci with changes in their methylation status include, but not limited to, methods based on immunoprecipitation of DNA with antibodies that recognize 5-methylcytidine, methods based on use of methylation dependent restriction endonucleases and PCR such as McrBC-PCR methods (Rabinowicz, et al. Genome Res. 13: 2658-2664 2003; Li et al., Plant Cell 20:259-276, 2008), sequencing of bisulfite-converted DNA (Frommer et al. Proc. Natl. Acad. Sci. U.S.A. 89 (5): 1827-31; Tost et al. BioTechniques 35 (1): 152-156, 2003), methylation-specific PCR analysis of bisulfite treated DNA (Herman et al. Proc. Natl. Acad. Sci. U.S.A. 93 (18): 9821-6, 1996), deep sequencing based methods (Wang et al. The Plant Cell 21:1053-1069 (2009)), methylation sensitive single nucleotide primer extension (MsSnuPE; Gonzalgo and Jones Nucleic Acids Res. 25 (12): 2529-2531, 1997), fluorescence correlation spectroscopy (Umezu et al. Anal Biochem. 415(2):145-50, 2011), single molecule real time sequencing methods (Flusberg et al. Nature Methods 7, 461-465), high resolution melting analysis (Wojdacz and Dobrovic (2007) Nucleic Acids Res. 35 (6): e41), and the like.

VI. Introducing a Chromosomal Modification Associated with a Useful Trait into a Plant Methods for introducing various chromosomal modifications that can confer a useful trait into a plant, as well as the plants, plant parts, and products of those plant parts are also provided herein. Chromosomal alterations and/or chromosomal mutations induced by suppression of MSH1 can be identified as described herein. Once identified, chromosomal modifications including, but not limited to, chromosomal alterations, chromosomal mutations, or transgenes that provide for the same genetic effect as the chromosomal alterations and/or chromosomal mutations induced by suppression of MSH1 can be introduced into host plants to obtain plants that exhibit the desired trait. In this context, the "same genetic effect" means that the introduced chromosomal modification provides for an increase and/or a reduction in expression of one or more endogenous plant genes that is similar to that observed in a plant that has been subjected to MSH1 suppression and exhibits the useful trait. In certain embodiments where an endogenous gene is methylated in a plant subjected to MSH1 suppression and exhibits both reduced expression of that gene and a useful trait, chromosomal modifications in other plants that also result in reduced expression of that gene and the useful trait are provided. In certain embodiments where an endogenous gene is demethylated in a plant subjected to MSH1 suppression and exhibits both increased expression of that gene and a useful trait, chromosomal modifications in other plants that also result in increased expression of that gene and that useful trait are provided.

In certain embodiments, the chromosomal modification that is introduced is a chromosomal alteration. Chromosomal alterations including, but not limited to, a difference in a methylation state can be introduced by crossing a plant comprising the chromosomal alteration to a plant that lacks the chromosomal alteration and selecting for the presence of the alteration in F1, F2, or any subsequent generation progeny plants of the cross. In still other embodiments, the chromosomal alterations in specific target genes can be introduced by expression of a siRNA or hairpin RNA targeted to that gene by RNA directed DNA methylation (Chinnusamy V et al. Sci China Ser C-Life Sci. (2009) 52(4): 331-343; Cigan et al. Plant J 43 929-940, 2005; Heilersig et al. (2006) Mol Genet Genomics 275 437-449; Miki and Shimamoto, Plant Journal 56(4):539-49; Okano et al. Plant Journal 53(1):65-77, 2008).

In certain embodiments, the chromosomal modification is a chromosomal mutation. Chromosomal mutations that provide for reductions or increases in expression of an endogenous gene of a chromosomal locus can include, but are not limited to, insertions, deletions, and/or substitutions of nucleotide sequences in a gene. Chromosomal mutations can result in decreased expression of a gene by a variety of mechanisms that include, but are not limited to, introduction of missense codons, frame-shift mutations, premature translational stop codons, promoter deletions, mutations that disrupt mRNA processing, and the like. Chromosomal mutations that result in increased expression of a gene include, but are not limited to, promoter substitutions, removal of negative regulatory elements from the gene, and the like. Chromosomal mutations can be introduced into specific loci of a plant by any applicable method. Applicable methods for introducing chromosomal mutations in endogenous plant chromosomal loci include, but are not limited to, homologous double stranded break repair (Wright et al., Plant J. 44, 693, 2005; D'Halluin, et al., Plant Biotech. J. 6:93, 2008), non-homologous end joining or a combination of non-homologous end joining and homologous recombination (reviewed in Puchta, J. Exp. Bot. 56, 1, 2005; Wright et al., Plant J. 44, 693, 2005), meganuclease-induced, site specific double stranded break repair (WO/06097853A1, WO/06097784A1, WO/04067736A2, U.S. 20070117128A1), and zinc finger nuclease mediated homologous recombination (WO 03/080809, WO 05/014791, WO 07014275, WO 08/021207). In still other embodiments, desired mutations in endogenous plant chromosomal loci can be identified through use of the TILLING technology (Targeting Induced Local Lesions in Genomes) as described (Henikoff et al., Plant Physiol. 2004, 135:630-636).

In other embodiments, chromosomal modifications that provide for the desired genetic effect can comprise a transgene. Transgenes that can result in decreased expression of an gene by a variety of mechanisms that include, but are not limited to, dominant-negative mutants, a small inhibitory RNA (siRNA), a microRNA (miRNA), a co-suppressing sense RNA, and/or an anti-sense RNA and the like. US patents incorporated herein by reference in their entireties that describe suppression of endogenous plant genes by transgenes include U.S. Pat. Nos. 7,109,393, 5,231,020 and 5,283,184 (co-suppression methods); and U.S. Pat. Nos. 5,107,065 and 5,759,829 (antisense methods). In certain embodiments, transgenes specifically designed to produce double-stranded RNA (dsRNA) molecules with homology to the endogenous gene of a chromosomal locus can be used to decrease expression of that endogenous gene. In such embodiments, the sense strand sequences of the dsRNA can be separated from the antisense sequences by a spacer sequence, preferably one that promotes the formation of a dsRNA (double-stranded RNA) molecule. Examples of such spacer sequences include, but are not limited to, those set forth in Wesley et al., Plant J., 27(6):581-90 (2001), and Hamilton et al., Plant J., 15:737-746 (1998). Vectors for inhibiting endogenous plant genes with transgene-mediated expression of hairpin RNAs are disclosed in U.S. Patent Application Nos. 20050164394, 20050160490, and 20040231016, each of which is incorporated herein by reference in their entirety.

Transgenes that result in increased expression of a gene of a chromosomal locus include, but are not limited to, a recombinant gene fused to heterologous promoters that are stronger than the native promoter, a recombinant gene comprising elements such as heterologous introns, 5' untranslated regions, 3' untranslated regions that provide for increased expression, and combinations thereof. Such promoter, intron, 5' untranslated, 3' untranslated regions, and any necessary polyadenylation regions can be operably linked to the DNA of interest in recombinant DNA molecules that comprise parts of transgenes useful for making chromosomal modifications as provided herein.

Exemplary promoters useful for expression of transgenes include, but are not limited to, enhanced or duplicate versions of the viral CaMV35S and FMV35S promoters (U.S. Pat. No. 5,378,619, incorporated herein by reference in its entirety), the cauliflower mosaic virus (CaMV) 19S promoters, the rice Act1 promoter and the Figwort Mosaic Virus (FMV) 35S promoter (U.S. Pat. No. 5,463,175; incorporated herein by reference in its entirety). Exemplary introns useful for transgene expression include, but are not limited to, the maize hsp70 intron (U.S. Pat. No. 5,424,412; incorporated by reference herein in its entirety), the rice Act1 intron (McElroy et al., 1990, The Plant Cell, Vol. 2, 163-171), the CAT-1 intron (Cazzonnelli and Velten, Plant Molecular Biology Reporter 21: 271-280, September 2003), the pKANNIBAL intron (Wesley et al., Plant J. 2001 27(6):581-90; Collier et al., 2005, Plant J 43: 449-457), the PIV2 intron (Mankin et al. (1997) Plant Mol. Biol. Rep. 15(2): 186-196) and the "Super Ubiquitin" intron (U.S. Pat. No. 6,596,925, incorporated herein by reference in its entirety; Collier et al., 2005, Plant J 43: 449-457). Exemplary polyadenylation sequences include, but are not limited to, and *Agrobacterium* tumor-inducing (Ti) plasmid nopaline synthase (NOS) gene and the pea ssRUBISCO E9 gene polyadenylation sequences.

VII. Screening and Selection of Outcrossed Progeny of MSH1 Suppressed Plants or Plants comprising Modified Chromosomal Loci that Exhibit Improved or Useful Traits Plant lines obtained by the methods provided herein can be screened and selected for a variety of useful traits by using a wide variety of techniques. In particular embodiments provided herein, individual progeny plant lines obtained from the outcrosses of plants where MSH1 expression was suppressed to other plants are screened and selected for the desired useful traits.

In certain embodiments, the screened and selected trait is improved plant yield. In certain embodiments, such yield improvements are improvements in the yield of a plant line relative to one or more parental line(s) under non-stress conditions. Non-stress conditions comprise conditions where water, temperature, nutrients, minerals, and light fall within typical ranges for cultivation of the plant species. Such typical ranges for cultivation comprise amounts or values of water, temperature, nutrients, minerals, and/or light that are neither insufficient nor excessive. In certain embodiments, such yield improvements are improvements in the yield of a plant line relative to parental line(s) under abiotic stress conditions. Such abiotic stress conditions include, but are not limited to, conditions where water, temperature, nutrients, minerals, and/or light that are either insufficient or excessive. Abiotic stress conditions would thus include, but are not limited to, drought stress, osmotic stress, nitrogen stress, phosphorous stress, mineral stress, heat stress, cold stress, and/or light stress. In this context, mineral stress includes, but is not limited to, stress due to insufficient or excessive potassium, calcium, magnesium, iron, manganese, copper, zinc, boron, aluminum, or silicon. In this context, mineral stress includes, but is not limited to, stress due to excessive amounts of heavy metals including, but not limited to, cadmium, copper, nickel, zinc, lead, and chromium.

Improvements in yield in plant lines obtained by the methods provided herein can be identified by direct measurements of wet or dry biomass including, but not limited to, grain, lint, leaves, stems, or seed. Improvements in yield can also be assessed by measuring yield related traits that include, but are not limited to, 100 seed weight, a harvest index, and seed weight. In certain embodiments, such yield improvements are improvements in the yield of a plant line relative to one or more parental line(s) and can be readily determined by growing plant lines obtained by the methods provided herein in parallel with the parental plants. In certain embodiments, field trials to determine differences in yield whereby plots of test and control plants are replicated, randomized, and controlled for variation can be employed (Giesbrecht F G and Gumpertz M L. 2004. Planning, Construction, and Statistical Analysis of Comparative Experiments. Wiley. New York; Mead, R. 1997. Design of plant breeding trials. In Statistical Methods for Plant Variety Evaluation. eds. Kempton and Fox. Chapman and Hall. London.). Methods for spacing of the test plants (i.e. plants obtained with the methods of this invention) with check plants (parental or other controls) to obtain yield data suitable for comparisons are provided in references that include, but are not limited to, any of Cullis, B. et al. J. Agric. Biol. Env. Stat. 11:381-393; and Besag, J. and Kempton, R A. 1986. Biometrics 42: 231-251.).

In certain embodiments, the screened and selected trait is improved resistance to biotic plant stress relative to the parental lines. Biotic plant stress includes, but is not limited to, stress imposed by plant fungal pathogens, plant bacterial pathogens, plant viral pathogens, insects, nematodes, and herbivores. In certain embodiments, screening and selection of plant lines that exhibit resistance to fungal pathogens including, but not limited to, an *Alternaria* sp., an *Ascochyta* sp., a *Botrytis* sp.; a *Cercospora* sp., a *Colletotrichum* sp., a *Diaporthe* sp., a *Diplodia* sp., an *Erysiphe* sp., a *Fusarium* sp., *Gaeumanomyces* sp., *Helminthosporium* sp., *Macrophomina* sp., a *Nectria* sp., a *Peronospora* sp., a *Phakopsora* sp., *Phialophora* sp., a *Phoma* sp., a *Phymatotrichum* sp., a *Phytophthora* sp., a *Plasmopara* sp., a *Puccinia* sp., a *Podosphaera* sp., a *Pyrenophora* sp., a *Pyricularia* sp, a *Pythium* sp., a *Rhizoctonia* sp., a *Scerotium* sp., a *Sclerotinia* sp., a *Septoria* sp., a *Thielaviopsis* sp., an *Uncinula* sp, a *Venturia* sp., and a *Verticillium* sp. is provided. In certain embodiments, screening and selection of plant lines that exhibit resistance to bacterial pathogens including, but not limited to, an *Erwinia* sp., a *Pseudomonas* sp., and a *Xanthamonas* sp. is provided. In certain embodiments, screening and selection of plant lines that exhibit resistance to insects including, but not limited to, aphids and other piercing/sucking insects such as *Lygus* sp., lepidoteran insects such as *Armigera* sp., *Helicoverpa* sp., *Heliothis* sp., and *Pseudoplusia* sp., and coleopteran insects such as *Diabroticus* sp. is provided. In certain embodiments, screening and selection of plant lines that exhibit resistance to nematodes including, but not limited to, *Meloidogyne* sp., *Heterodera* sp., *Belonolaimus* sp., *Ditylenchus* sp., *Globodera* sp., *Naccobbus* sp., and *Xiphinema* sp. is provided.

Other useful traits that can be obtained by the methods provided herein include various seed quality traits including, but not limited to, improvements in either the compositions or amounts of oil, protein, or starch in the seed. Still other useful traits that can be obtained by methods provided herein include, but are not limited to, increased biomass, non-flowering, male sterility, digestability, seed filling period, maturity (either earlier or later as desired), reduced lodging, and plant height (either increased or decreased as desired).

In addition to any of the aforementioned traits, particularly useful traits for *sorghum* that can be obtained by the methods provided herein also include, but are not limited to: i) agronomic traits (flowering time, days to flower, days to flower-post rainy, days to flower-rainy; ii) fungal disease resistance (*sorghum* downy mildew resistance—glasshouse, *sorghum* downy mildew resistance-field, *sorghum* grain mold, *sorghum* leaf blight resistance, *sorghum* rust resistance; iii) grain related trait: (Grain dry weight, grain number, grain number per square meter, Grain weight over panicle. seed color, seed luster, seed size); iv) growth and development stage related traits (basal tillers number, days to harvest, days to maturity, nodal tillering, plant height, plant height-postrainy); v) infloresence anatomy and morphology trait (threshability); vi) Insect damage resistance (*sorghum* shoot fly resistance-post-rainy, *sorghum* shoot fly resistance-rainy, *sorghum* stem borer resistance); vii) leaf related traits (leaf color, leaf midrib color, leaf vein color, flag leaf weight, leaf weight, rest of leaves weight); viii) mineral and ion content related traits (shoot potassium content, shoot sodium content); ix) panicle related traits (number of panicles, panicle compactness and shape, panicle exertion, panicle harvest index, panicle length, panicle weight, panicle weight without grain, panicle width); x) phytochemical compound content (plant pigmentation); xii) spikelet anatomy and morphology traits (glume color, glume covering); xiii) stem related trait (stem over leaf weight, stem weight); and xiv) miscellaneous traits (stover related traits, metabolised energy, nitrogen digestibility, organic matter digestibility, stover dry weight).

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Construction of Transgenic Plants that provide for Suppression of MSH1

A vector that provides for suppression of MSH1 in tomato and tobacco was constructed as follows. A segment encoding amino acids 651-870 of the MSH1 protein was derived from a tomato EST sequence (SEQ ID NO:5) by using the primer sequences TOM-CD1F (5'-CGCAGGTATCAC-GAGGCAAGTGCTAAGG-3; SEQ ID NO:11) and TOM-CD1R (5'-ATCCCCAAACAGCCAATTTCGTCCAG-GATCCCCAAACAGCCAATTTCGTCCAGG-3; SEQ ID NO:12) and cloned in forward and reverse orientation, separated by an intron sequence. The base vector, pUCR-NAi-intron harbors the second intron of the *Arabidopsis* small nuclear riboprotein (At4g02840; SEQ ID NO: 13). The CaMV35S promoter and transcription terminator regulate expression of the construction and the neomycin phosphotransferase II (nptII) reporter gene, and the insert is flanked by right border and left border integration sequences. *Agrobacterium tumefaciens* strain C58C1/pMP90 (28) was used for transformation in tobacco (Horsch R B, et al. (1985) *Science* 227:1229-1231) and tomato (McCormick et al. 1986) *Plant Cell Rep* 5:81-84).

Millet and *sorghum* RNAi lines were derived by similar procedures and materials, with transformations and plant regeneration carried out according to the procedures of Howe et al. (Plant Cell Rep 25:784-91, 2006). The RNAi vector for millet was directed against the millet MSH1 gene whereas the RNAi vector for *sorghum* was directed against the *sorghum* MSH1 gene (SEQ ID NO: 6). Segments encoding 157 amino acids from the MSH1 C-terminal were amplified from total cDNA of pearl millet and *sorghum* using primers: zm-msf8 (5'-GGTTGAGGAGCCT-GAATCTCTGAAGAAC-3'; SEQ ID NO:15) and zm-msr8 (5'-CTCGCCAGAGATTCGAGATATACCGAAG-3'; SEQ ID NO:16). PCR products were cloned in forward and reverse orientation, separated by an intron sequence. The base vector, pUCRNAi-intron, which harbors the second intron of the *Arabidopsis* small nuclear riboprotein (At4g02840; SEQ ID NO: 13), was provided by H. Cerutti (University of Nebraska, Lincoln, Nebr.). The vector pPTN290, a derivative of pPZP212 (Hajdukiewicz et al. 1994, Plant Mol Biol.; 25(6):989-94), was used to introduce the Msh1-RNAi cassettes under the control of the maize ubiquitin 1 promoter coupled with its first intron, and its transcription is terminated by CaMV 35S terminator. The CaMV 35S promoter and terminator regulate the expression of the neomycin phosphotransferase II (nptII) reporter gene, and the insert is flanked by right border and left border integration sequences. The *Agrobacterium tumefaciens* strain NTL4 (Luo Z-Q et al., 2001, Mol Plant Microbe Interact., 14(1):98-103) was used for inoculating embryos from pearl millet maintainer Tift23 DBE1 and *sorghum* Tx430 lines. Detailed transformation procedures used for pearl millet are the same as for *sorghum* (Howe et al., 2006, Plant Cell Rep 25:784-91).

Example 2

Phenotypic Effects of MSH1 Suppression

Figure 4:
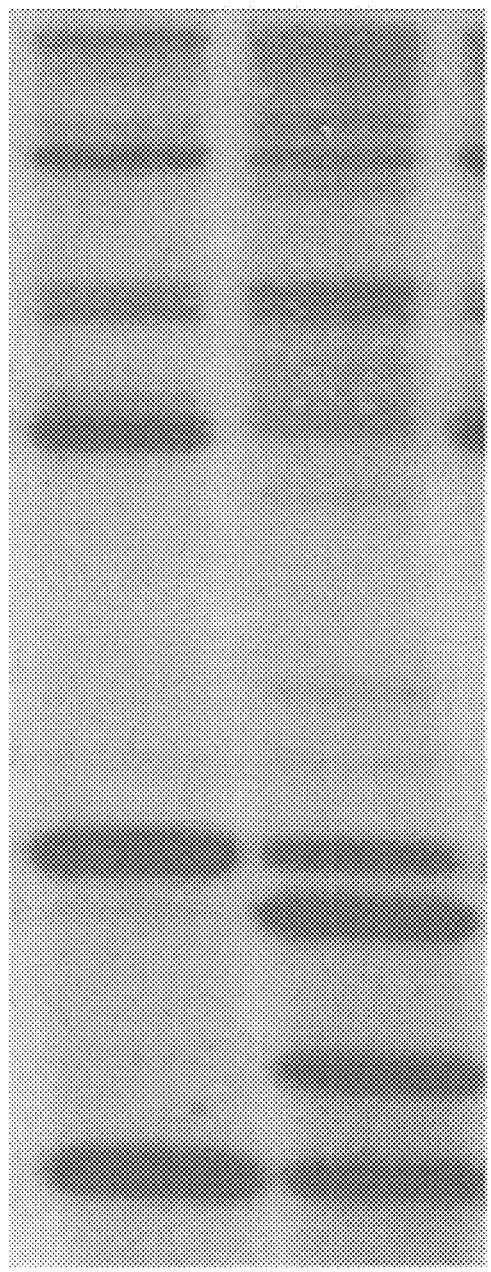
FIG. 4 illustrates mitochondrial DNA rearrangements in *Arabidopsis* that had been subjected to MSH1 suppression.
Figure 5:
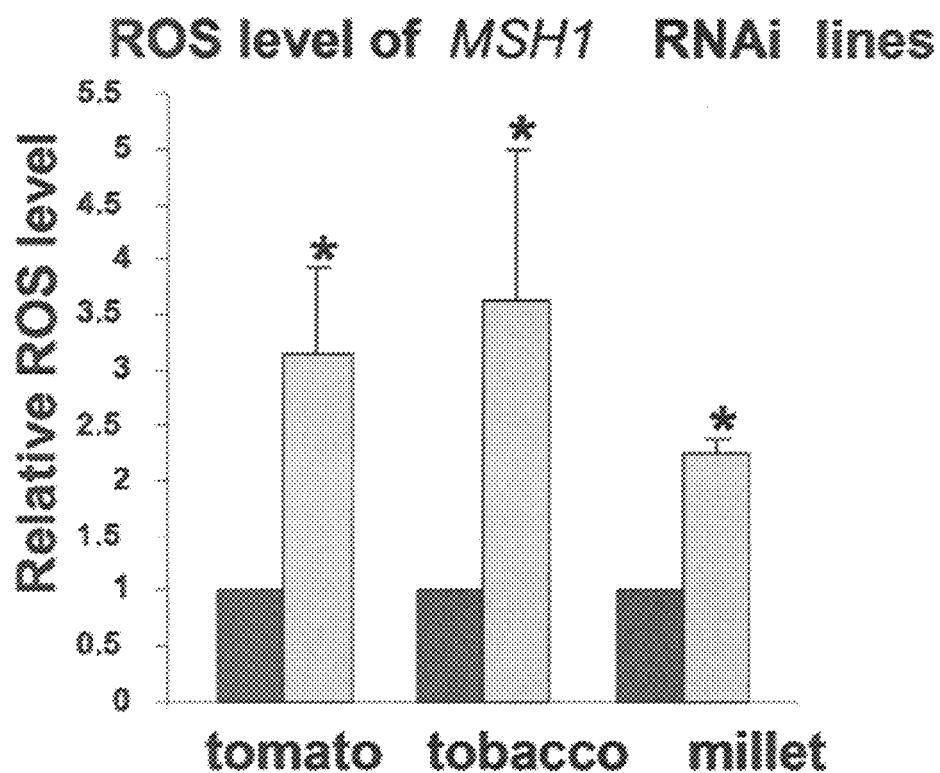
FIG. 5 illustrates increases in Reactive Oxygen Species (ROS) that are observed in tomato, tobacco, and millet plants subjected to MSH1 suppression.

MSH1 expression suppressed transgenically by use of RNAi in five plant species: soybean (*Glycine max* (L.) Merr), tomato (*Solanum lycopersicum* L), tobacco (*Nicotiana tabacum* L.), millet (*Pennisetum glaucum* (L.) R. Br.) and *sorghum* (*Sorghum bicolor* (L.) Moench). In each case, similar changes were observed, including cytoplasmic male sterility, evidence of variegation and altered chloroplast development, reduced growth rate and dwarfing, altered flowering time or non-flowering, enhanced branching, reduced flavonoid biosynthesis and lack of anthocyanins, enhanced pathogen susceptibility, and altered leaf morphologies (see FIG. 1). Variegation, dwarfing, and mitochondrial DNA rearrangements are also observed in various plants subjected to MSH1 suppression as shown in FIGS. 2, 3, and 4, respectively. Physiologically, plants show reduced ATP and enhanced ROS levels, reduced mitochondrial motility, enhanced mitophagy, expression of stress response pathways, and altered cytokinin and GA metabolism (ROS data in FIG. 5).

The striking phenotypic similarities among plant species indicate that many of the msh1-associated changes are programmed responses. Transcript and metabolic analyses have identified several pathways associated with the emerging phenotypes (Table 1). Sorghum and *Arabidopsis* transcript profiling experiments show reduced expression of cell cycle genes, altered flowering gene expression (FLC), and enhanced GA catabolism (GA20-ox2 and GA20-ox6) in the reduced growth phenotypes. Plants are restored in growth rate and flower induction with the application of gibberellic acid.

TABLE 1

Sample transcript/metabolic profiling results in *Arabidopsis* showing correspondence in pathway changes.

| | Transcript Profiling | | | Metabolic Profiling | |
|---|---|---|---|---|---|
| AGI | Gene | msh1* | metabolite | Col-0 | msh1 |
| A. Redox/oxidative stress response | | | | | |
| AT3G22370 | AOX1A | 2.2 | Glutathione† | 22,520 | 33,322 |
| AT5G20230 | ATBCB | 10.9 | Ascorbate† | 289,996 | 460,261 |
| AT2G21640 | Oxid Stress Response | 2.9 | phosphate | 12.3M | 32.1M |
| AT4G20830 | FAD-binding domain protein | 2.6 | | | |
| B. Photosynthesis genes | | | | | |
| AT5G66570 | PSBO-1 | −1.3 | Sucrose† | 26,969.4 | N.D. |
| AT3G50820 | PSBO-2 | −1.4 | Raffinose† | 49,427.8 | N.D. |
| AT4G02770 | PSAD-1 | −1.6 | | | |
| AT2G30790 | PSBP-2 | −2 | | | |
| C. GA response | | | | | |
| AT1G30040 | ATGA20X2 (GA catabolism) | 1.7 | GA53 | 11 ng/g DW | N.D. |
| AT1G02400 | ATGA20X6 (GA catabolism) | 9.3 | GA19 | 7 ng/g DW | N.D. |
| AT2G14900 | GA-regulated protein | −3.3 | | | |

*Fold change of levels in msh1 relative to Col-0,
†values are normalized raw area count from mass spectrometer analysis,
N.D. non detectable
A limited dataset is shown. Shading indicates downregulation in msh1.

Example 3

Figure 6:
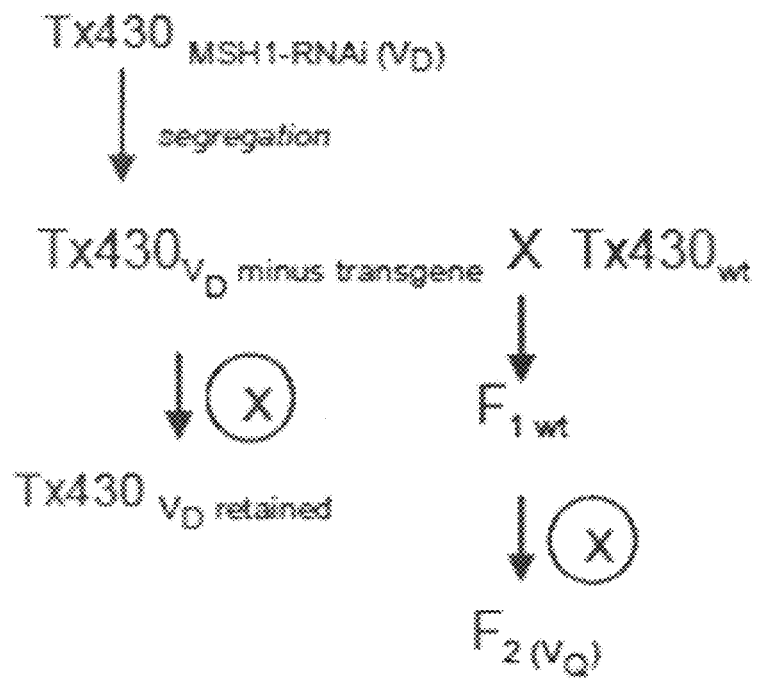
FIG. 6 illustrates an exemplary and non-limiting scheme for obtaining plants that exhibit various types of heritable phenotypic variation referred to herein as "discrete variation" ($V_D$) as a result of having been subjected to MSH1 suppression and for obtaining plant lines that can exhibit "quantitative variation" or "$V_Q$" and various useful traits.

Genetic Analysis of Tx430 *Sorghum* Lines following Exposure to and Loss of the MSH1 RNAi Transgene by Segregation A non-transgenic, highly dwarfed, delayed flowering and variegated TX430 *sorghum* plant was obtained from a segregation population of progeny plants from a parental Tx430 *sorghum* plant that was heterozygous for a transgene that inhibits MSH1 expression by RNA interference (RNAi). Tx430 was the original genotype used to obtain the transgenic *sorghum* plant comprising the transgene that inhibits MSH1 expression. Crossing of this non-transgenic, highly dwarfed, delayed flowering and variegated TX430 *sorghum* plant by isogenic TX430 wildtype as pollen parent, produced a wildtype F1 phenotype that showed no evidence of the original dwarfing, delay in flowering or variegation phenotypes (FIG. 6). This was a surprising result, since we had assumed the RNAi-induced changes to be organellar, and anticipated maternal transmission of the phenotypes. Introduction of the wildtype genome neutralized the original RNAi-induced effects. The F2 population, derived by self-pollination of these F1 plants, produced a broad distribution of phenotypic variation, referred to as quantitative variation (VQ), some of which is described in Table 2. SAS PROC MIXED was used for all analyses in Table 2. Each trait was analyzed with the fixed effect of line in the model and heterogeneous variances among the lines were assumed and estimated, along with standard errors of the estimates. A chi-square test of the heterogeneous variance model against the homogeneous variance model was performed. A significant chi-square value indicates statistically significant differences among line variances. While a small proportion (ca. 1/50 plants) shows the dwarfed, variegated phenotype, and about 50% show cytoplasmic male sterility as a likely mitochondrial genetic lesion (Hanson and Bentolila, 2004), a large proportion of the population shows significant quantitative variation in aboveground fresh and dry weight biomass, panicle weight, and other useful agronomic features. Particularly intriguing in these data is the observed capacity within the population to out-perform either parent for several traits. The range of diversity cannot reasonably be accounted for by nuclear genetic variation, since the original cross is TX430×TX430 (made in the greenhouse with bagged panicles).

TABLE 2

Assessment of phenotypic variation in *Sorghum*

| | Line | $N^1$ | Lsmean | Variance | SE variance | Chi-Square$^2$ | P-value |
|---|---|---|---|---|---|---|---|
| Plant Height (cm) | F1 | 31 | 156.65 | 1195.5 | 308.68 | 156.98 | <0.0001 |
| Plant Height (cm) | F2 | 274 | 143.63 | 1400.33 | 119.86 | | |
| Plant Height (cm) | Dwarf | 55 | 48.29 | 61.17 | 11.77 | | |
| Plant Height (cm) | Wild-type | 18 | 131.11 | 32.58 | 11.17 | | |
| Panicle Length (cm) | F1 | 13 | 27.154 | 11.81 | 4.82 | 4.75 | 0.0931 |
| Panicle Length (cm) | F2 | 275 | 27.171 | 17.20 | 1.47 | | |
| Panicle Length (cm) | Wild Type | 11 | 26.636 | 5.85 | 2.61 | | |

TABLE 2-continued

Assessment of phenotypic variation in Sorghum

| | Line | N[1] | Lsmean | Variance | SE variance | Chi-Square[2] | P-value |
|---|---|---|---|---|---|---|---|
| Panicle Weight (grams) | F1 | 16 | 46.63 | 252.65 | 92.25 | 14.49 | 0.0007 |
| Panicle Weight (grams) | F2 | 368 | 45.26 | 365.78 | 27.00 | | |
| Panicle Weight (grams) | Wild Type | 17 | 33.53 | 67.51 | 23.87 | | |
| Dry Biomass (grams) | F1 | 3 | 294.7 | 12258[3] | 12258 | 16.46 | 0.0009 |
| Dry Biomass (grams) | F2 | 52 | 224.8 | 3023.4 | 598.7 | | |
| Dry Biomass (grams) | Dwarf | 11 | 195.8 | 2696.6 | 1205.9 | | |
| Dry Biomass (grams) | Wild Type | 10 | 193.6 | 283.1 | 133.5 | | |

[1]N = number of observations in a line
[2]Chi-square test is test for differences among line variances
[3]The unusually high variance is the consequence of small sample size for this trait.

Example 4

Analysis of *Arabidopsis* MSH1/MSH1 F3 Progeny of a msh1/msh1×MSH1/MSH1 Cross In these experiments, the recessive msh1 mutation was removed by segregation. The recessive msh1/msh1 Columbia ecotype parent was first crossed to wild type Columbia ecotype plants as pollen donor (Col-0 msh1×Col-0wt) to obtain an F1 population of msh1/MSH1 plants. The F1 progeny were (selfed to obtain an F2 population segregating for the msh1locus. MSH1/MSH1 F2 progeny were selected from the F2 population and selfed to obtain MSH1/MSH1 F3 progeny of the selected MSH1/MSH1 F2 parent.

Figure 7:
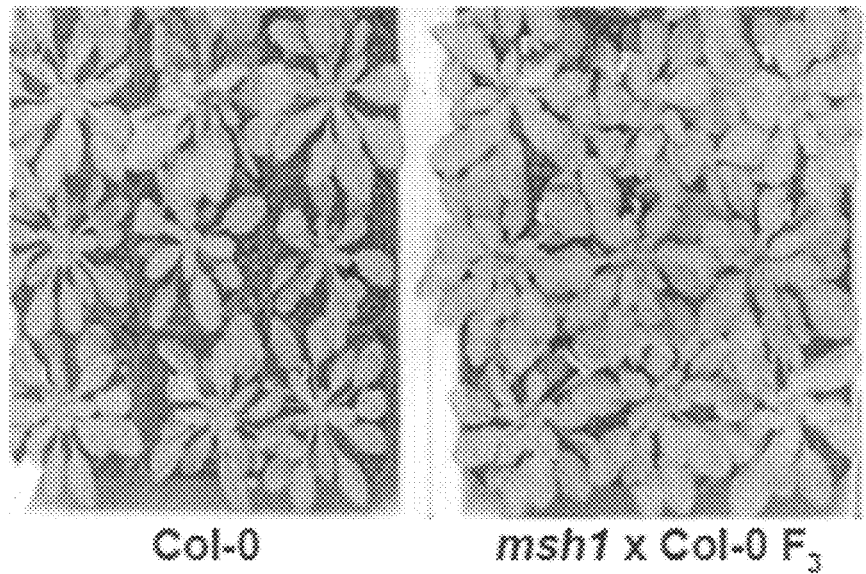
FIG. 7 illustrates an *Arabidopsis* plant line (msh1×Col-0 $F_3$) that exhibits increases in biomass relative to an otherwise isogenic parental plant that had not been subjected to MSH1 suppression (Col-0).

To assess phenotypic variation in the selected F3 MSH1/MSH1 *Arabidopsis* lines, measurements were averaged from four plants each of wildtype Col-0 and the selected F3 progeny line as shown in Table 3. Fresh biomass was total aboveground leaf tissue, base diameter was the diameter of root-stem transition zone, and stalk diameter was the diameter of the floral stalk. Each parameter showed a 20-24% increase in the selected F3 progeny line, even though the two plant populations (i.e. Col-O and MSH1/MSH1 F3) progeny should be genetically identical. Plants from each group were selected to represent the same stage of development and same number of leaves (average of 48 leaves per plant in each group). The data of Table 3 and plants shown in FIG. 7 represent one selected F3 population. Other selected F3 populations (not shown) demonstrated uniformly lower average growth relative to wildtype.

One MSH1/MSH1 F3 progeny derived from the Col-0 msh1×Col-0wt cross showed markedly enhanced growth as shown in FIG. 7 and Table 3. Such markedly enhanced growth resembles hybrid vigor in that the F3 progeny of the cross exhibit increased growth relative to the Col-O parental germplasm. However, these experiments can be distinguished from instances where hybrid vigor is obtained by crossing parental lines of two distinct heterotic genetic backgrounds since the two parental lines used here both had Columbia ecotype genetic backgrounds and differed only in the presence of the recessive msh1 mutation in one of the Columbia ecotype parents.

TABLE 3

Assessment of phenotypic variation in *Arabidopsis*.

| | Col-0 (wild-type parent) | msh1 × Col-0 F3 (MSH1 positive progeny) |
|---|---|---|
| Fresh biomass (g) | 4.9 | 6.3 |
| Base diameter (mm) | 2.2 | 2.9 |
| Stalk diameter (mm) | 1.6 | 2.0 |

Example 5

Variation in Plant Height, Panicle Weight, and Grain Yield in Individual *Sorghum* Plants in an F2 Population Obtained from an Outcross to MSH1—Suppressed *Sorghum*

F2 populations of *sorghum* plants derived from parental Tx430 *sorghum* plants that had been subjected to MSH1 suppression as describe in FIG. 6 and Example 3 were assayed for variation in plant height (FIG. 8), panicle weight (FIG. 9), and grain yield (FIG. 10) by comparing the values for individual plants in the population.

Figure 8:
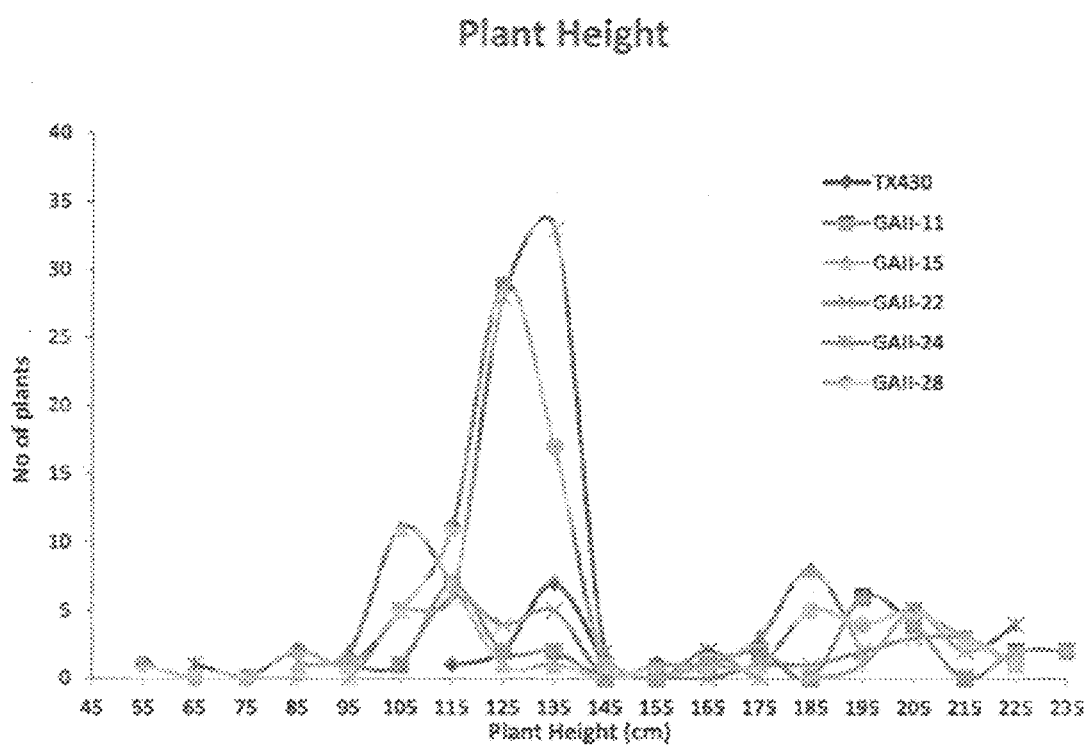
FIG. 8 illustrates the distribution of plant heights (in cM) that are obtained in distinct *sorghum* lines GAII-11 (squares), GA11-15 (triangles), GAII-22 (opposing brackets), GAII-24, and GAII-28 (circles) derived from out-crosses of plants where MSH1 expression was suppressed. The wild type reference line is fx WT (diamonds).
Figure 9:
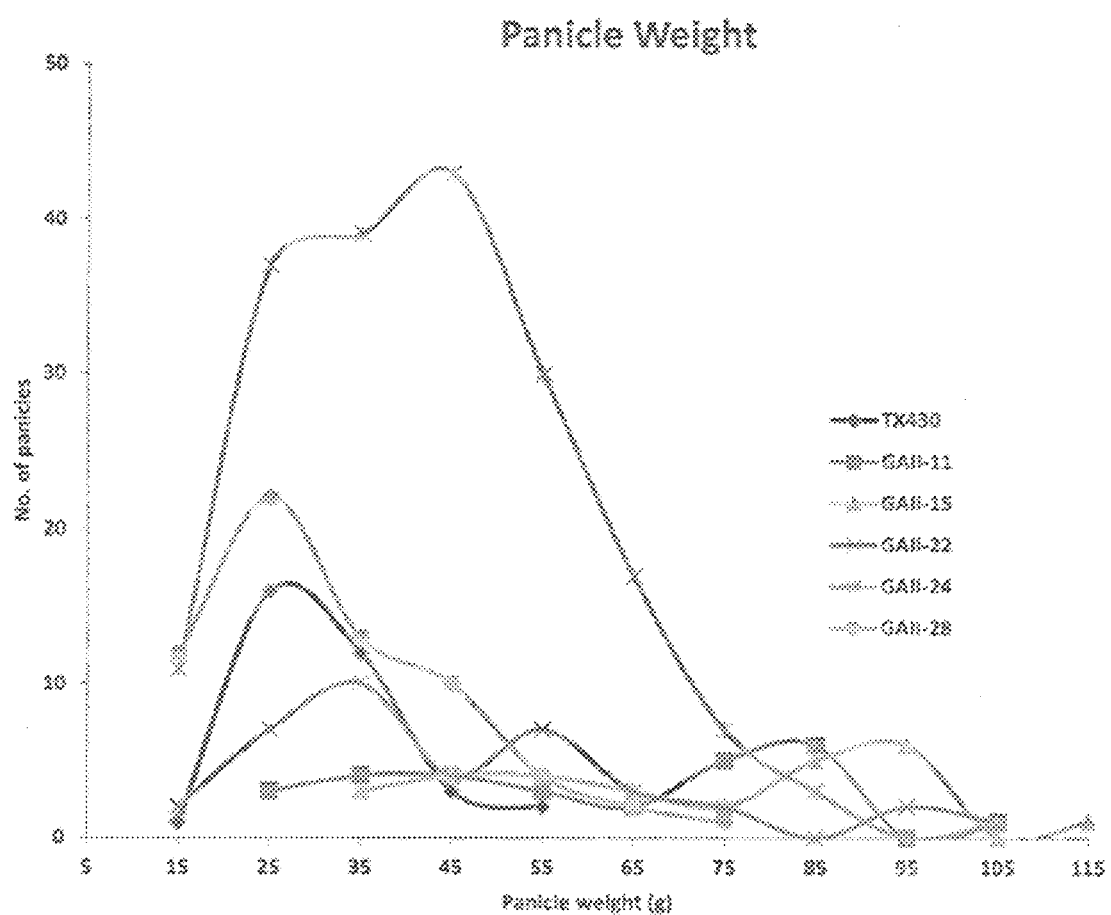
FIG. 9 illustrates the distribution of panicle weights (in grams) that are obtained in distinct *sorghum* lines GAII-11 (squares), GA11-15 (triangles), GAII-22 (opposing brackets), GAII-24, and GAII-28 (circles) derived from out-crosses of plants where MSH1 expression was suppressed. The wild type reference line is fx WT (diamonds).
Figure 10:
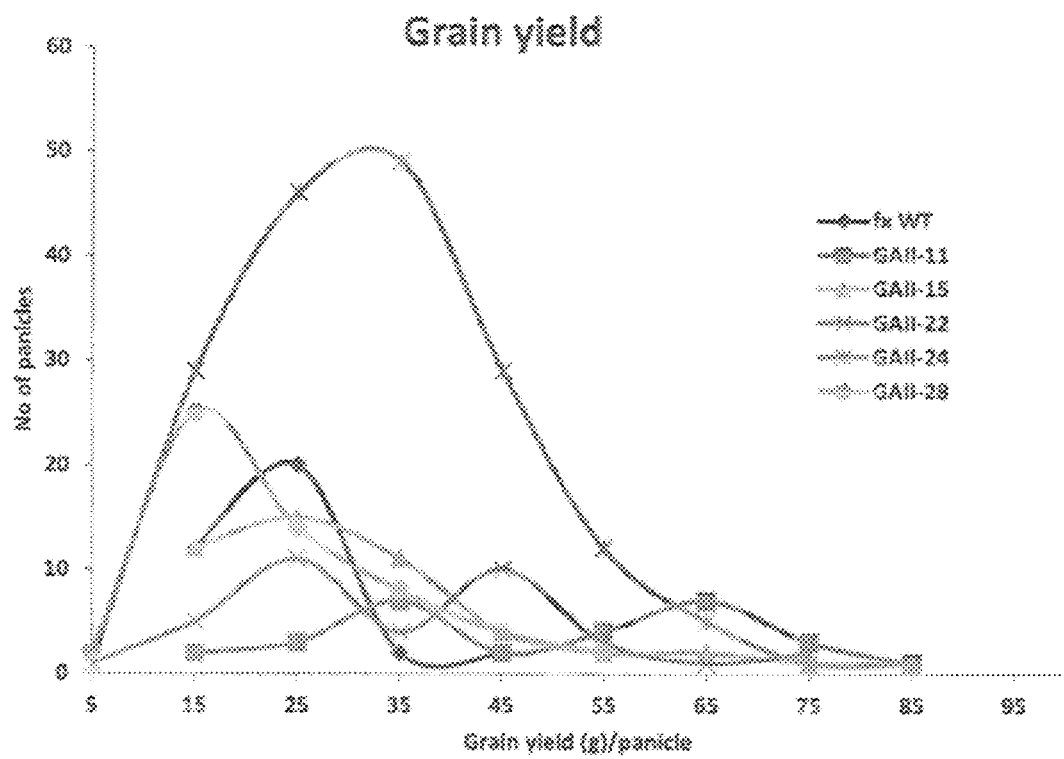
FIG. 10 illustrates the distribution of grain yield (in grams) that are obtained in distinct *sorghum* lines GAII-11 (squares), GA11-15 (triangles), GAII-22 (opposing brackets), GAII-24, and GAII-28 (circles) derived from out-crosses of plants where MSH1 expression was suppressed. The wild type reference line is fx WT (diamonds).

Significant variation was observed between individual plants within the F2 population. More specifically, certain *sorghum* lines exhibited distinctive bi-phasic distributions of plants within the F2 populations with respect to these traits. For example, the F2 population of *sorghum* line GAII-11 exhibited one subpopulation of plants with plant height between about 105 and 125 cM and another sub-population of plants with a plant height between about 185 to 215 cM. These subpopulations were represented by "peaks" in the FIG. 8 plot. Similar distributions of subpopulations are also observed for *sorghum* lines GA11-15, GA11-28 and GA11-24 in the FIG. 8 plot. For the GA11-11, GA11-15, GA11-28 and GA11-24 F2 populations, one set of sub-populations either overlapped or had a value less than that of the wild-type TA430 control plant heights while another sub-population had a value that was clearly greater than that of the wild-type PA430 control plants (FIG. 8). Subpopulations and/or individual plants in the GA11-11, GA11-15, GA11-28 and GA11-24 F2 populations also exhibited panicle weights and grain yields that either overlapped or had a value less than that of the wild-type TA430 control plant heights while other sub-populations or plants had a value that was clearly greater than that of the wild-type PA430 control plants (FIGS. 9 and 10).

It is concluded that differences in *sorghum* plant height, panicle weight, and grain yield are observed between: a) distinct subpopulations of plants within a given F2 population of *sorghum* plants of a given *sorghum* line; and/or: b) a distinct sub-populations of plants within a given F2 population of *sorghum* plants of a given *sorghum* line and the wild-type parental control line. It is further contemplated that those sub-populations of *sorghum* plants that exhibit desirable increases in plant height, panicle number, and/or grain yield may comprise certain differences in their chromosomal DNA methylation state, their chromosomal DNA sequence, post-translation modifications of a histone protein associated with a chromosomal locus, or any combination thereof that either contribute directly to such useful traits (i.e. have a direct causal relationship to the useful trait) or are associated by either genetic or epigenetic linkage(s) to loci that contribute directly to such desirable traits.

Example 6

Characterization of Small RNA Profiles and DNA Methylation State in Plants Exhibiting Useful Traits Associated with MSH1 Suppression A comparison of small RNA profiles and DNA methylation states in reference plants that do not exhibit a useful phenotype and test plants comprising an altered chromosomal locus associated with a useful trait can be used to identify altered chromosomal loci. Methods for making such comparisons that can be generalized to a variety of plants are provided in this example.

In a particular exemplary embodiment, the small RNA profiles and DNA methylation states of various chromosomal loci in: a) distinct subpopulations of plants within a given F2 population of *sorghum* plants of a given *sorghum* line; and/or: b) a distinct sub-populations of plants within a given F2 population of *sorghum* plants of a given *sorghum* line and the wild-type parental control line; are compared. The objective of these comparisons is to identify differences in the small RNA profiles and/or methylation of certain chromosomal DNA loci between those *sorghum* plants that exhibit the useful traits and *sorghum* plants that do not exhibit the useful traits. Such differences can then be used to identify sRNAs or chromosomal loci that either contribute directly to such useful traits or are associated by either genetic linkage(s) or through an epigenetic mechanism to loci that contribute directly to such useful traits. *Sorghum* plants that will be examined can include wild type plants, plants from distinct sub-populations and/or individual plants in the GA11-11, GA11-15, GA11-28 and GA11-24 or other *sorghum* line F2 populations that exhibit plant heights, panicle weights, and/or grain yields that either overlap or have a value less than that of the wildtype TA430 control plant heights as well as plants from distinct sub-populations and/or individual plants in the GA11-11, GA11-15, GA11-28 and GA11-24 or other *sorghum* line F2 populations that exhibit plant heights, panicle weights, and/or grain yields that are clearly greater than that of the wild-type TA430 control plants. Such plants and such sub-populations are exemplarily described in the preceding Example 5 and in FIGS. 8, 9, and 10.

The small RNA (sRNA) profiles of wild type *sorghum* (Tx430), F1 *sorghum*, and selected F2 *sorghum* plants derived from different sub-populations are determined. *Sorghum* sub-populations or plants that will be examined can include wild type plants, and subpopulations and/or individual plants in the GA11-11, GA11-15, GA11-28 and GA11-24 or other *sorghum* F2 populations as described above. For example, certain *sorghum* populations subjected to MSH1 suppression can exhibit panicle weights and grain yields that either overlap or have a value less than that of the wild-type TA430 control plant heights while other *sorghum* sub-populations or plants can a value that was clearly greater than that of the wild-type TA430 control plants as shown in FIGS. 9 and 10 can be subjected to deep sequencing to identify the types (qualitative analysis) and relative amounts (quantitative analysis) of sRNAs present in these various plant lines. Such qualitative and quantitative analyses can then be used to establish correlations between the presence or absence of a given phenotype and the presence, absence, or relative abundance of a given sRNA.

Deep sequencing techniques to characterize sRNA populations can be determined as described by methods including but not limited to those described by Zhou et al. PLoS One. 2010; 5(12): e15224; or Glazov et al. PLoS One. 2009 Jul. 27; 4(7):e6349. In certain embodiments, three biological replicates can be sequenced for each sample and sRNA libraries can be prepared and sequenced according to an Illumina™ protocol. Briefly, low-molecular weight sRNAs (17-27 nt in length) can be isolated from total RNA by size fractionation. Following ligation of 3' and 5' adaptors to sRNAs, RT-PCR will be performed to construct the sRNA library. The library will be purified and validated according to the Illumina™ protocol and Illumina™-based deep sequencing of the library can be performed Following removal of common sequences (rRNA, tRNA, snRNA, and snoRNA), the remaining sRNA sequences will be subjected to several analyses. The first analysis is to assess distribution of sRNAs in the genome, with the expectation of identifying altered sRNA distribution by disruption of MSH1 function. Analysis of genomic clustering will be used to examine the distribution of sRNA-generating loci in the genome. An sRNA cluster will be defined as a group of sRNAs, in which each small RNA is <100 nt from its nearest neighbor as described in Johnson et al. (2009). Based on this definition, sRNAs at the ends of a cluster are >100 nt away from the next nearest small RNA outside the cluster (Johnson et al., 2009). The differential expression of siRNA signatures among different plant lines can be compared to gain insight into their relationship with disrupted MSH1 function. This will be accomplished by comparing the relative abundance of miRNAs or siRNAs in each library derived from each plant line. The SAMseq method can be used to perform statistical analysis of significant levels of differential expression. Several sRNAs that exhibit differential expression patterns in deep-sequencing analysis can be selected for validation using RNA gel blot analysis.

To gain information on the relationship between alterations in DNA methylation and sRNAs levels in various samples, regions containing DNA methylation (described below) can be mapped against the sRNAs obtained from this study and other publicly available databases, to identify regions containing DNA methylation that are potentially targeted by sRNA.

The sRNA and DNA methylation profiles obtained from different lines can be compared to determine whether alterations in DNA methylation content correlate with changes in sRNA abundance in various plant samples that exhibit different MSH-1 induced phenotypes. One concern in such analyses is that sRNAs may be too short to be detected. sRNAs are typically generated from much longer transcripts in plants. Therefore, one can expand analyses of DNA methylation to 500 by on either side of the chromosomal locus containing sRNAs as reported (Wang et al., 2009). This analysis would indicate whether DNA methylation could potentially be induced by sRNAs. Such studies can be used to identify detectable alterations in the sRNA population that alter genome methylation patterning that can result from MSH1 suppression. Any of the sRNAs and/or genomic regions identified in such studies can then be suppressed and/or up-regulated using transgenic or other genomic alteration-based approaches to obtain desirable phenotypes that can result from MSH1 suppression.

Association of useful phenotypes induced by MSH1 suppression in various plants and plant lines with chromosomal alterations can also be determined by methyl C detection in whole genome bisulfite sequencing experiments. The genomic bisulfite deep sequencing method (Lister 2009) can be used to obtain a whole-genome view of all possible methylated cytosines in the genomes of plants subjected to MSH1 suppression including, but not limited to, those plants exhibiting desirable phenotypes or undesirable phenotypes, and suitable control plants including, but not limited to, parental lines that have not been subjected to MSH1 suppression. In an exemplary method, about five micrograms of genomic DNA can be isolated and spiked with 25 nanograms of unmethylated lambda DNA that serves as an internal control for the efficiency of bisulfite conversion of non-methylated cytosine nucleotides to uracils. The DNA can be sonicated to an average length of about 300 bp and a DNA library can be constructed. An exemplary method that follows an Illumina™ Paired End protocol comprising modifications where the end repair cocktail do not contain dCTP and the adapters contain methylated cytosines (Illumina™) can be used. Bisulfite conversion of the adapter-ligated DNA can be followed by limited cycles of PCR with a uracil insensitive PfuTurboCx DNA polymerase (Stratagene™). Gel-isolated 200-300 by products will be sequenced to a length of 110 bases on the Illumina™ GA II system. The standard Illumina™ image analysis, base calling and processing pipeline will be used to obtain the initial processed sequences. In certain embodiments, only those sequences that pass internal Illumina™ filters (Chastity >0.6) will be stored together with the PHRED-like sequence quality scores in FastQ files. Sequence reads will be trimmed to before the first Project Description 12 occurrence of a low quality base (PHRED score <2). Any remaining cytosine bases in the sequences can be converted to thymine and the genomic position of this retained in a methyl C coverage file. In certain embodiments, two reference genomes can be generated. In the first reference genome, corresponding to the "Watson" strand, the cytosines can be converted to thymines. In the second, corresponding to the Crick strand, guanines can be converted to adenines. The same conversion can be done for the internal control Lambda DNA, which will be analyzed as separate reference genomes for the efficiency of conversion of non-methylated cytosines. The Illumina sequences will be aligned to the two reference genomes with Bowtie (Langmead et al., 2009). In certain embodiments, only sequencing reads with unique starting positions will be scored (a second sequence starting at the same position will be discarded to minimize unequal PCR amplification distortion of the data). For the Lambda internal control, a conversion rate of nonmethylated cytosines to thymines of greater than 99% is expected and will be confirmed in pilot studies and a single lane analysis of each library (prior to further sequencing of the library), as determined using the internal Lambda DNA control sequences. The occurrence of cytosines in the bisulfite-treated Lambda DNA can be computed as a function of the sequence coverage (each sequence read counts as coverage of 1). Threshold values will be established to have a p-value of <0.01 for a cytosine occurring by sequencing error or incomplete conversion to uracil.

Two biological replicates can be used for each type of genome analyzed. The coverage can be 10× for each strand. This should be sufficient coverage to compare the individual biological replicates at most positions for individual variation. The combined sequence data from the two individuals will be combined for 20× coverage of each strand when comparing different genotype samples. The individual biological replicates can be used to establish coverage and methylation percentage thresholds to have a False Discovery Rate (FDR) of <0.05 for differences at specific positions. Selected regions showing methyl C differences can be analyzed by the traditional bisulfite-PCR-cloning method to validate the whole genome data and FDR predictions.

Example 7

Quantitative Analysis of Methylation and Phenotypic Variation in Response to MSH1 Suppression It is possible to exploit the quantitative phenotypic variation that emerges in an F2 population derived by crossing a MSH1 RNAi-derived phenotypic variant×wild type. The heritability and quantitative variation in various *sorghum* populations subjected to MSH1 suppression and control *sorghum* plants described herein can be determined to identify chromosomal alterations conferring useful traits. In certain embodiments, these methods can entail use of use bisulfite-derived DNA SNP polymorphisms identified by *sorghum* shotgun sequencing experiments in SNP development and detection. The *sorghum* genome is about 1628 cM, and we will aim for a SNP marker density of about 1 SNP/10 cM (centimorgans). Therefore, 163 Me-C sites for QTL analysis will be selected on the basis of their differential methylation in the whole genome analysis of up to five samples types (i.e. (1) wild type, (2) transgenic MSH1 knockdown plants showing dramatically reduced growth rate and delayed flowering, (3) nontransgenic segregants that retain the altered growth phenotype, (4) F1 plants (as shown in Figure (6) and (5) selected F2 plants exhibiting quantitative variation (FIG. 6)), and for an even 10-cM spacing across the *sorghum* genome.

DNA from 200 F2 individuals can be bisulfite-treated to create a C/T SNP in the subsequent PCR product. The ratio of C/T will depend on the degree of Me-C at each methylation site. PCR primers designed to the C-depleted sequences will be used to amplify targeted Me-C SNP regions in the bisulfite-treated DNA. The C/T polymorphism will be detected on a LightCycler 480 PCR system using Hybprobes™ (Roche, Indianapolis, Ind., USA). Hybprobes™ use fluorescence resonance energy transfer (FRET) between adjacent probes hybridized to the PCR product and differential melting to determine the C/T frequency at the Me-C SNP position. LightCycler™ Probe Design Software (Roche) will be used to design the Hyb-Probes, with the C/T polymorphism in the middle of the sensor probe. The ratio of PCR primers to obtain optimal asymmetric PCR of the Me-C strand for hybridization to the HybProbes™ will be experimentally determined for each SNP.

Heritability analysis. Up to about two hundred or more F3 families can be developed in *sorghum*. DNA can be extracted from each F2 individual giving rise to each F3 family. A replicated field trial of the F3 families can be conducted to perform heritability analysis of the putative epigenetic variation generated by the trans-generational effects of the MSH1 RNAi transgene (i.e. MSH1 suppression). For each species, single three meter rows will be arranged in a randomized complete block design with two replications. Populations will be grown in experimental fields.

QTL analysis. Along with the marker data on the 200 F2 individuals, the phenotypic data will be used in a QTL analysis to locate genomic regions affected by MSH1 in previous generations that are generating the observed variation for total biomass and seed yield. A genetic map will be

Example 8

Use of Msh1 Suppression to Alter the Epigenome to Produce Dramatic and Heritable Changes in Plant Growth Msh1 suppression was used to induce phenotypic and epigenetic variation, and to select derived phenotypes in the crop species *Sorghum bicolor* (L.) Moench and the model plant *Arabidopsis thaliana* (L.) Heynh.

Figure 11:
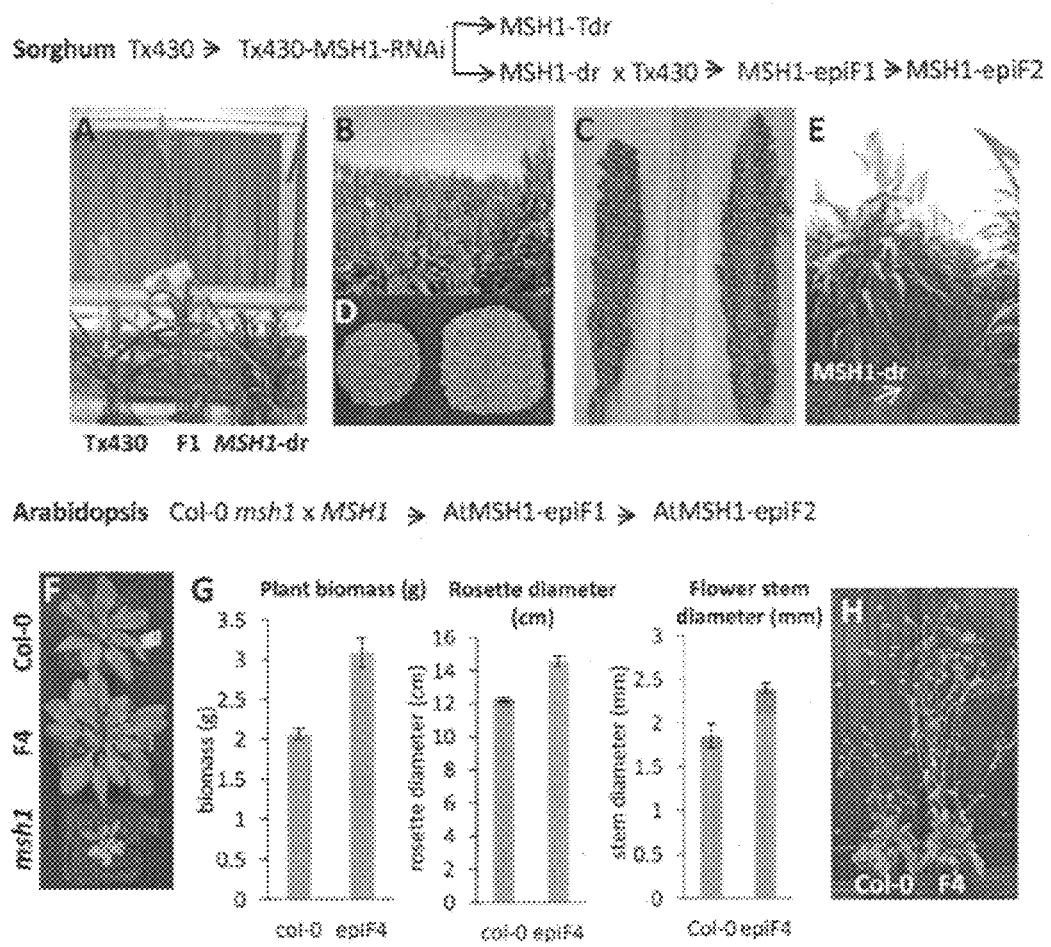
FIG. 11A-H illustrates the enhanced growth phenotype of MSH1-epi lines in *Arabidopsis* and *sorghum*. The transgene and crossing procedures used to derive *sorghum* and *Arabidopsis* epi-populations are indicated. (A) The phenotype of the F1 progeny derived from crossing Tx430×MSH1-dr. (B) Field grown epiF2, F3 and F4 *sorghum* lines show variation in plant architecture and height. (C) Panicles from Tx430 (on left, 66 gm, 8 mm stem) versus epi-F2 individual (on right, 112 gm, 11 mm stem). (D) seed yield from the panicles shown in C. (E) The MSH1-dr *sorghum* phenotype under field conditions. (F) Evidence of enhanced rosette growth in an epi-F4 line of *Arabidopsis*. (G) *Arabidopsis* epi-F4 plants shown enhanced plant biomass, rosette diameter and flower stem diameter relative to Col-0. Data shown as mean±SE from >6. (H) The *Arabidopsis* epiF4 phenotype at flowering.

FIG. 11 shows the transgene and crossing process that was used in this study for both *Arabidopsis* and *sorghum*. In *sorghum*, all experiments were conducted with the inbred line Tx430 (F. R. Miller, Crop Sci. 24, 1224, 1984), whereas *Arabidopsis* experiments were carried out in the inbred ecotype Columbia-0. MSH1-dr *sorghum* plants that no longer contain the MSH1-RNAi transgene are restored to normal MSH1 transcript levels; nevertheless, they maintain the altered growth phenotype through multiple generations of self-pollination. When crossed reciprocally to the wildtype inbred Tx430 line, progeny are restored to a normal phenotype. The derived F1 progeny, designated MSH1-epiF1, no longer show the dwarfed, tillering, late flowering phenotype. In fact, the plants grow taller and generally set more seed than the wildtype (FIG. 11A). Self-pollination of the MSH1-epiF1 plants produced an F2 population (MSH1-epiF2) that was strikingly variable in plant phenotype but showed no MSH1-dr phenotype (FIG. 11B-D). A proportion of greenhouse-grown MSH1-epiF3 families did show the MSH1-dr phenotype at a frequency of ca. 8% (Table 4), and no dwarf phenotype appeared in the epi-F4 lines.

TABLE 4

Frequency of MSH1-dr phenotype (8.4%) in epi-F3 families derived from *sorghum* Tx430 MSH1-dr × Tx430 and grown in the greenhouse. Derived epi-F4 families showed no evidence of the MSH1-dr phenotype (not shown).

| F3 family | N | Mean plant height (cm) | Tall or wildtype | Dwarf |
|---|---|---|---|---|
| 1 | 10 | 160 | 10 | 0 |
| 2 | 9 | 208 | 9 | 0 |
| 3 | 10 | 167 | 10 | 0 |
| 4 | 10 | 189 | 10 | 0 |
| 5 | 8 | 186 | 7 | 1 |
| 6 | 10 | 114 | 10 | 0 |
| 7 | 9 | 203 | 9 | 0 |
| 8 | 7 | 102 | 6 | 1 |
| 9 | 2 | 107 | 2 | 0 |
| 10 | 9 | 116 | 9 | 0 |
| 11 | 4 | 89 | 3 | 1 |
| 12 | 6 | 118 | 6 | 0 |
| 13 | 10 | 187 | 10 | 0 |
| 14 | 8 | 150 | 6 | 2 |
| 15 | 7 | 81 | 3 | 4 |
| 16 | 10 | 143 | 7 | 3 |
| 17 | 5 | 122 | 5 | 0 |
| 18 | 10 | 137 | 9 | 1 |
| 19 | 10 | 98 | 10 | 0 |
| 19 | 154 | | 141 | 13 |

The F2 plants, and subsequent populations derived by self-pollinating, showed variation for agronomic performance traits, including panicle and plant architecture, tillering time and number, plant height and above-ground biomass, and yield components of panicle and seed weight (Table 5 for plant height and grain yield). Similarly dramatic changes in growth were observed in *Arabidopsis* populations derived from crossing the msh1 mutant with wildtype, followed by selection for the homozygous MSH1/MSH1 F2 plants and serial self-pollination (FIG. 11F-H).

Figure 12:
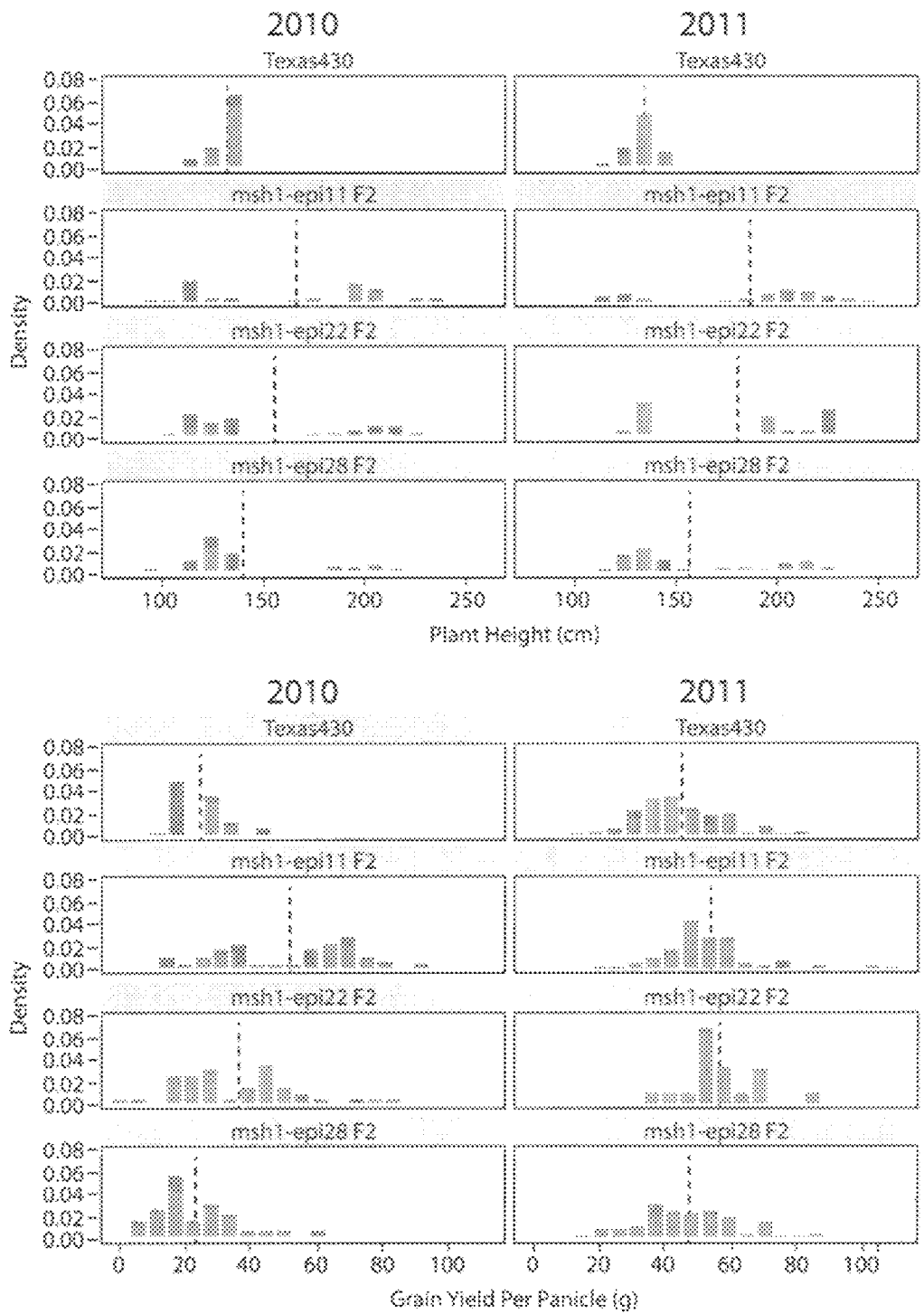
FIG. 12 illustrates enhanced phenotypic variation in *sorghum* MSH1-epiF2 lines. Phenotypic distributions are shown for plant height and grain yield from three independent *sorghum* epiF2 populations grown in two field plantings. Population means are shown by dashed vertical lines.

*Sorghum* MSH1-epiF2, MSH1-epiF3, and MSH1-epiF4 populations grown under field conditions in 2010 and 2011 permitted larger-scale evaluations of plant growth changes (Tables 5, 6, 7). Phenotypic distributions were developed from results of two *sorghum* field experiments, demonstrating patterns in the MSH1-epiF2 approaching bimodality (FIG. 12). All traits showed quantitative patterns of variation. F3 and F4 progenies were tested under both field and greenhouse conditions, displaying heritability for plant height with increasing uniformity among plants each generation, and response to selection for grain yield, although this trait was subjected to less rigorous selection during growth in the greenhouse (FIG. 13). These results suggest a high degree of heritability and selection response for the variation observed.

Altered plant development in *sorghum* MSH1-dr and *Arabidopsis* msh1 mutant lines, including variation in growth rate, branching, maturation and flowering, was conditioned by chloroplast changes (see following Example 9). We were interested in assessing the relationship of MSH1-epiF2 variation to these organellar influences. *Arabidopsis* MSH1 hemi-complementation lines, derived by introducing a mitochondrial-versus chloroplast-targeted MSH1 transgene to the msh1 mutant line (Y.-Z. Xu et al. *Plant Cell* 239:3428, 2011), distinguish mitochondrial and chloroplast contributions to the phenomenon. Both mitochondrial and chloroplast hemi-complementation lines were crossed as females to wildtype (Col-0) to produce F1 and F2 progeny. F1 plants from crosses to the chloroplast-complemented line produced phenotypes similar to wildtype, although about 25% of the F1 plants showed altered leaf curling and delayed flowering (FIG. 16). This curling phenotype may be a consequence of MSH1 overexpression, since F1 plants contain both the wildtype MSH1 allele and the transgene. The phenotype resembles effects of altered salicylic acid pathway regulation, an epigenetically regulated process (T. L. Stokes et al. Genes Dev 16, 171, 2002). F1 progeny from crosses to the mitochondrial complemented line displayed phenotypic variation in plant growth, with over 30% of the plants showing enhanced growth, larger rosette diameter, thicker floral stems and earlier flowering time, similar to MSH1-epiF3 phenotypes (FIGS. 14A & 17; Table 8). These results were further confirmed in the mitochondrial vs. chloroplast-complemented F2 populations (FIG. 14B-E), and suggest that the MSH1-epiF3 enhanced growth changes derive from restoring MSH1 function to plants that have undergone the MSH1-dr developmental reprogramming phenomenon.

Figure 18C:
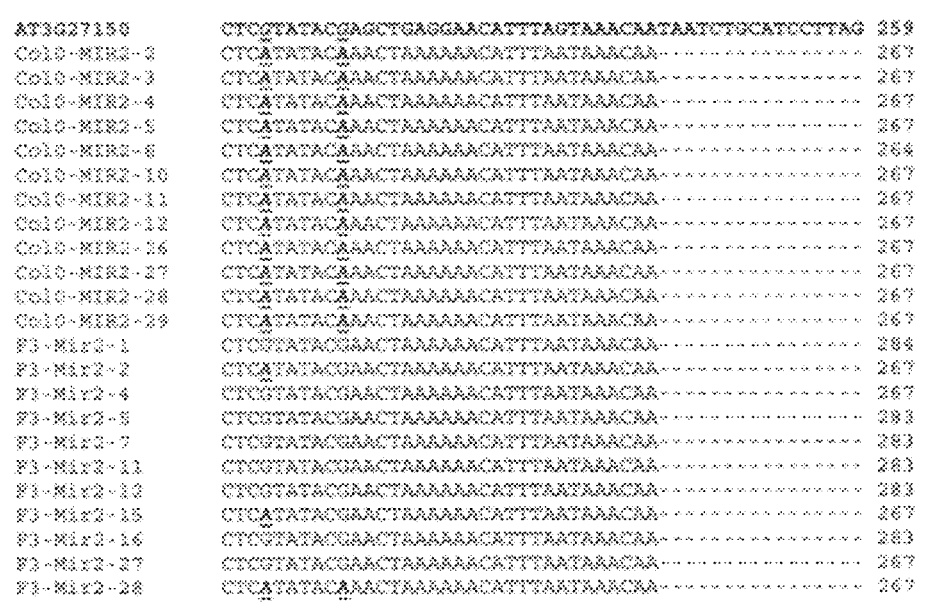

*Arabidopsis* wildtype and MSH1-epiF3 plants, both Col-0 background, were investigated for evidence of methylome changes that might accompany heritable MSH1-derived phenotypes. Experiments used sodium bisulfite treated genomic DNA and genome-wide next-gen sequence analysis (Lister et al. *Cell* 133, 523, 2008). Methylation changes were extensive, with differentially methylated positions involving predominantly CpG sites, with over 91,000 differentially methylated positions in over 1700 regions (Table 11, FIG. 15A). The pattern of methylation changes were consistent with observed heritability of altered phenotypes, with the large proportion of changes in gene coding regions of the genome, resembling data from studies of natural epigenetic variation (C. Becker et al. Nature 480, 245,2011; R. J. Schmitz et al. Science 334, 369, 2011). Comparison of the non-differential methylation patterns in wildtype and MSH1-epiF3 lines in this study against patterns reported by a recent *Arabidopsis* study of natural methylation variation (C. Becker et al. Nature 480, 245,2011), showed remarkable correspondence of pattern (FIG. 15B, MSH1-epiF5 line2), confirming consistency of the Col-0 genome methylation analysis between the two studies. Striking differences were evident between the two studies for the regions of the chromosomes enriched for differentially methylated positions; the Becker et al. analysis of natural variation, shown for illustration purposes in FIG. 15C, showed fairly uniform distribution of differential methylation spanning each chromosome, whereas the MSH1-epiF3 lines revealed irregular patterns of differential methylation that concentrated in discrete regions of the genome (FIG. 15B). Several DMRs showing changes in methylation were confirmed by targeted PCR amplification and sequencing of bisulfite-treated DNA intervals (FIG. 18, Table 9). From these results we infer that the developmental variation that accompanies MSH1 disruption involves pronounced changes in the methylation architecture of the plant. The inheritance pattern of the MSH1-dr phenotype, showing independence from the transgene and involvement of numerous developmental pathways, also indicates that epigenetic changes occur in the MSH1-dr lines.

TABLE 5

The majority of *sorghum* $F_2$ epi-line families consistently show a statistically significant increase in variation (p-value <0.05) in plant height and grain yield compared to wild-type Tx430. Data were collected from plants grown under field conditions in 2010 and 2011

| | | Plant Height | | | | Grain Yield Per Panicle | | | |
|---|---|---|---|---|---|---|---|---|---|
| Year | Family | Mean (cm) | Std. Error (cm) | Variance (cm$^2$) | p-value † | Mean (g) | Std. Error (g) | Variance (g$^2$) | p-value † |
| 2010 | Tx430 | 132.10 | 2.42 | 58.54 | — | 24.19 | 0.93 | 27.11 | — |
| 2010 | msh1-epi11 F2 | 165.77 | 8.40 | 2116.67 | <0.001 | 51.29 | 3.45 | 368.88 | <0.001 |
| 2010 | msh1-epi15 F2 | 135.30 | 5.02 | 1182.95 | <0.001 | 33.69 | 2.47 | 293.54 | <0.001 |
| 2010 | msh1-epi22 F2 | 155.96 | 8.13 | 1783.50 | <0.001 | 35.84 | 2.77 | 290.84 | <0.001 |
| 2010 | msh1-epi24 F2 | 140.04 | 3.40 | 1031.38 | <0.05 | 34.35 | 1.04 | 185.51 | <0.001 |
| 2010 | msh1-epi28 F2 | 140.87 | 3.61 | 1130.67 | <0.01 | 23.75 | 1.58 | 141.69 | <0.001 |
| 2011 | Tx430 | 134.50 | 0.55 | 64.95 | — | 45.20 | 0.89 | 146.49 | — |
| 2011 | msh1-epi11 F2 | 186.57 | 3.93 | 1912.00 | <0.001 | 53.96 | 1.55 | 272.73 | <0.05 |
| 2011 | msh1-epi15 F2 | 177.04 | 2.41 | 1532.86 | <0.001 | 53.66 | 0.94 | 184.36 | <0.05 |
| 2011 | msh1-epi22 F2 | 180.73 | 10.62 | 1691.50 | <0.001 | 56.62 | 2.59 | 114.08 | NS |
| 2011 | msh1-epi24 F2 | 154.78 | 1.98 | 1196.96 | <0.001 | 47.92 | 1.12 | 266.97 | <0.001 |
| 2011 | msh1-epi28 F2 | 156.91 | 3.57 | 1238.75 | <0.001 | 47.49 | 1.27 | 222.84 | <0.05 |

† p-values based on Levene's test for homogeneity of variance in comparison to wild-type Tx430.
NS = not significant

TABLE 6

Three of five *sorghum* epi-F2 line families measured for dry biomass show a statistically significant increase in variation (p-value <0.05) compared to wildtype Tx430. Data were collected from plants grown under field conditions in 2011.

| | Dry Biomass Yield | | | |
|---|---|---|---|---|
| Family | Mean (g) | Std. Error (g) | Variance (g$^2$) | p-value† |
| Tx430 | 53.11 | 1.94 | 79.35 | — |
| msh1-epi11 F2 | 85.49 | 2.77 | 99.53 | NS |
| msh1-epi15 F2 | 75.08 | 3.24 | 252.04 | <0.05 |
| msh1-epi22 F2 | 92.33 | 7.90 | 311.83 | NS |
| msh1-epi24 F2 | 68.26 | 3.54 | 363.73 | <0.001 |
| msh1-epi28 F2 | 66.93 | 5.79 | 503.32 | <0.001 |

†p-values based on Levene's test for homogeneity of variance in comparison to wildtype Tx430.
NS = not significant

TABLE 7

*Sorghum* $F_4$ generation data showing significant differences (p-value <0.05) for many epi-F4 families in plant height (37 of 39 lines) and grain yield (11 of 39 lines) compared to wildtype Tx430. Data were collected from plants grown under field conditions in 2011.

| | Plant Height | | | | Grain Yield Per Panicle | | | |
|---|---|---|---|---|---|---|---|---|
| | | | | | Mean | Std. Error | Std. Dev. | |
| Line | Mean (cm) | Std. Error (cm) | Std. Dev. (cm) | p-value * | (g) | (g) | (g) | p-value * |
| Tx430 | 134.45 | 0.56 | 8.08 | — | 45.44 | 0.88 | 11.95 | — |
| 10.3 | 135.29 | 1.42 | 6.515 | NS | 40.71 | 2.17 | 9.71 | NS |
| 12.1 | 186.24 | 8.77 | 47.23 | <0.001 | 44.33 | 2.73 | 11.60 | NS |
| 12.10 | 238.85 | 2.01 | 9.00 | <0.001 | 51.84 | 2.68 | 11.99 | NS |
| 12.3 | 220.00 | 2.55 | 11.11 | <0.001 | 54.86 | 3.15 | 13.72 | NS |
| 14.1 | 187.20 | 5.72 | 25.59 | <0.001 | 56.59 | 3.50 | 14.87 | <0.05 |
| 15.2 | 222.75 | 1.76 | 8.63 | <0.001 | 33.88 | 1.74 | 8.52 | <0.001 |
| 17.2 | 174.52 | 6.55 | 36.49 | <0.001 | 61.25 | 2.54 | 11.05 | <0.001 |
| 17.3 | 192.54 | 5.66 | 27.72 | <0.001 | 47.02 | 1.74 | 8.16 | NS |
| 2a-9 | 216.00 | 4.44 | 19.34 | <0.001 | 48.12 | 3.40 | 14.41 | NS |
| 2b-1 | 217.83 | 3.41 | 14.49 | <0.001 | 43.88 | 4.29 | 17.69 | NS |
| 2b-3 | 221.24 | 2.10 | 8.67 | <0.001 | 54.82 | 3.94 | 16.25 | NS |
| 2b-4 | 217.44 | 2.65 | 10.60 | <0.001 | 44.75 | 3.36 | 12.08 | NS |
| 2b-5 | 231.32 | 3.46 | 15.07 | <0.001 | 53.40 | 3.00 | 12.70 | NS |
| 2b-6 | 229.90 | 1.49 | 6.67 | <0.001 | 50.52 | 2.43 | 10.87 | NS |
| 2b-8 | 231.21 | 1.61 | 7.89 | <0.001 | 39.95 | 2.71 | 13.27 | NS |
| 2b-10 | 207.80 | 4.01 | 17.94 | <0.001 | 66.94 | 3.99 | 17.84 | <0.001 |
| 3a-1 | 226.79 | 2.74 | 11.93 | <0.001 | 44.39 | 3.09 | 12.73 | NS |
| 3a-2 | 141.10 | 1.78 | 7.97 | <0.05 | 46.61 | 2.61 | 11.96 | NS |
| 3a-6 | 233.14 | 1.63 | 7.48 | <0.001 | 44.35 | 2.24 | 10.27 | NS |
| 3a-7 | 190.29 | 9.58 | 43.89 | <0.001 | 40.30 | 3.91 | 15.15 | NS |
| 3b-1 | 219.44 | 2.51 | 10.68 | <0.001 | 41.47 | 3.69 | 13.82 | NS |
| 3b-2 | 216.65 | 2.49 | 11.12 | <0.001 | 52.14 | 1.96 | 8.77 | <0.05 |
| 3b-3 | 210.28 | 3.34 | 14.17 | <0.001 | 39.99 | 3.69 | 11.08 | NS |
| 3b-4 | 207.64 | 4.72927 | 22.18 | <0.001 | 51.17 | 2.27 | 10.39 | NS |
| 3b-7 | 223.41 | 2.353125 | 9.70 | <0.001 | 53.10 | 3.45 | 14.22 | NS |
| 3b-10 | 234.14 | 2.170879 | 8.12 | <0.001 | 43.04 | 3.22 | 9.10 | NS |
| 4a-1 | 213.07 | 3.164821 | 11.84 | <0.001 | 60.54 | 6.29 | 22.66 | <0.01 |
| 4a-2 | 217.67 | 7.862307 | 30.45 | <0.001 | 52.33 | 3.40 | 10.77 | NS |
| 4a-4 | 225.56 | 5.02882 | 21.34 | <0.001 | 52.11 | 3.58 | 14.78 | NS |
| 4a-7 | 233.28 | 2.471809 | 10.49 | <0.001 | 41.28 | 2.15 | 8.87 | NS |
| 4a-8 | 200.31 | 7.515885 | 38.32 | <0.001 | 48.04 | 2.60 | 11.05 | NS |
| 4b-10 | 133.06 | 1.403771 | 5.62 | NS | 63.96 | 3.39 | 13.55 | <0.001 |
| 5a-1 | 216.48 | 4.470243 | 17.88 | <0.001 | 68.90 | 4.72 | 18.28 | <0.001 |
| 5a-2 | 219.05 | 2.415699 | 11.07 | <0.001 | 43.20 | 1.64 | 7.49 | NS |
| 5a-3 | 220.58 | 2.359566 | 8.17 | <0.001 | 58.30 | 2.66 | 9.58 | <0.001 |
| 5a-5 | 214.67 | 3.178769 | 13.49 | <0.001 | 52.16 | 2.60 | 11.02 | NS |
| 5a-6 | 216.94 | 3.335935 | 13.75 | <0.001 | 53.35 | 2.80 | 11.21 | NS |
| 5a-8 | 212.90 | 3.568814 | 19.55 | <0.001 | 52.74 | 1.41 | 7.74 | <0.001 |
| 5a-9 | 227.29 | 2.318808 | 10.63 | <0.001 | 59.80 | 3.36 | 15.38 | <0.01 |

* p-values based on max-t test for multiple comparison of means (Dunnett contrasts) using heteroscedastic consistent covariance estimation (E. Herberich et al. PLoS One. 5(3): e9788 (2010)), against wildtype Tx430.
NS = not significant

TABLE 8

Analysis of phenotype data from individual *Arabidopsis* $F_2$ families derived by crossing hemi-complementation lines × Col-0 wildtype. SSU-MSH1 refers to lines transformed with the plastid-targeted form of MSH1; AOX-MSH1 refers. to lines containing the mitochondrial-targeted form of the MSH1 transgene. In all genetic experiments using hemi-complementation, presence of the transgene was confirmed with a PCR-based assay.

| | Rosette diameter | | | | | Fresh biomass | | | | |
|---|---|---|---|---|---|---|---|---|---|---|
| Population | Mean (cm) | N | Std Error | Std Dev | p-value | Mean (g) | N | Std Error | Std Dev | p-value |
| AOX-MSH1 | 11.07 | 36 | 0.37 | 2.23 | <0.001 | 8.86 | 10 | 0.47 | 1.33 | NS |
| SSU-MSH1 | 11.76 | 18 | 0.26 | 1.10 | <0.001 | 10 | 10 | 0.55 | 1.55 | NS |
| Col-0 | 12.98 | 42 | 0.24 | 1.59 | — | 9.45 | 10 | 0.43 | 1.36 | — |
| F-2 | 12.83 | 21 | 0.34 | 1.57 | NS | 15.07 | 10 | 0.66 | 2.07 | <0.001 |
| (AOX-MSH1 × Col-0)F-22 | 13.82 | 21 | 0.42 | 1.92 | <0.10 | 14.62 | 10 | 0.92 | 2.24 | <0.001 |
| (AOX-MSH1 × Col-0)F-28 | 14.85 | 21 | 0.31 | 1.42 | <0.001 | 13.27 | 10 | 0.70 | 1.99 | <0.001 |
| (AOX-MSH1 × Col-0)F-26 | 12.82 | 20 | 0.25 | 1.12 | NS | 10.57 | 10 | 0.66 | 1.74 | NS |
| (SSU-MSH1 × Col-0)F-29 | 11.9 | 21 | 0.27 | 1.25 | <0.001 | 10.5 | 10 | 0.45 | 1.19 | NS |

P values are based on two-tailed Student t-test comparing to Col-0
NS = Not Significant

TABLE 9

Sample differential methylation data for four DMRs, derived by PCR-based analysis of bisulfite-treated DNA from *Arabidopsis* wildtype Col-0 and MSH1-epiF3 lines.

| AGI | Gene | Region size (bp) | No. DMP in region | Site | % methylation in Col-0 | % methylation in F3 |
|---|---|---|---|---|---|---|
| AT5G67120 | RING/U-box superfamily protein | 200 | 8 | 1 | 20% | 86% |
| | | | | 2 | 30% | 86% |
| | | | | 3 | 20% | 100% |
| | | | | 4 | 30% | 100% |
| | | | | 5 | 30% | 100% |
| | | | | 6 | 30% | 100% |
| | | | | 7 | 30% | 86% |
| | | | | 8 | 20% | 100% |
| AT1G20690 | SWI-SNF related protein | 100 | 6 | 1 | 27% | 75% |
| | | | | 2 | 27% | 83% |
| | | | | 3 | 18% | 100% |
| | | | | 4 | 18% | 92% |
| | | | | 5 | 18% | 83% |
| | | | | 6 | 63% | 92% |
| AT3G27150 | Target of MIR2111-5p | | | | | |
| | region 1 | 200 | 9 | 1 | 0 | 58% |
| | | | | 2 | 0 | 67% |
| | | | | 3 | 0 | 92% |
| | | | | 4 | 0 | 100% |
| | | | | 5 | 0 | 83% |
| | | | | 6 | 0 | 92% |
| | | | | 7 | 0 | 67% |
| | | | | 8 | 0 | 92% |
| | | | | 9 | 0 | 75% |
| | region 2 | 250 | 17 | 1 | 0 | 100% |
| AT5G67120 | RING/U-box superfamily protein | 200 | 8 | 1 | 20% | 86% |
| | | | | 2 | 0 | 100% |
| | | | | 3 | 58% | 100% |
| | | | | 4 | 0 | 100% |
| | | | | 5 | 0 | 100% |
| | | | | 6 | 0 | 100% |
| | | | | 7 | 0 | 100% |
| | | | | 8 | 0 | 73% |
| | | | | 9 | 8% | 100% |
| | | | | 10 | 8% | 82% |
| | | | | 11 | 0 | 82% |
| | | | | 12 | 8% | 100% |
| | | | | 13 | 0 | 91% |
| | | | | 14 | 0 | 82% |
| | | | | 15 | 0 | 82% |
| | | | | 16 | 0 | 73% |
| | | | | 17 | 0 | 91% |

TABLE 10

Primers used in the study

| Primer name | Sequence (SEQ ID NO:) |
|---|---|
| *For bisulfite sequencing:* | |
| AT5G67120RING-F | 5'-TTTTTAGGAATTATTGAGTATTA TTGA-3' (SEQ ID NO: 17) |
| AT5G67120RING-R | 5'-AAATAAAAATCATACCCACATCC C-3' (SEQ ID NO: 18) |
| AT1G20690SWI-F | 5'-TGTTGAATTATTAAGATATTTAA GAT-3' (SEQ ID NO: 19) |
| AT1G20690SWI-R | 5'-TCAACCAATAAAAATTACCATCT AC-3' (SEQ ID NO: 20) |
| AT3g271501stMir2-F | 5'-TAAGTTTTTTTTAAGAGTTTGTA TTTGTAT-3' (SEQ ID NO: 21) |
| AT3g271501stMir2-R | 5'-TAAAAATAATCAAAACCTAACTT AC-3' (SEQ ID NO: 22) |
| AT3g271502ndMir2-F | 5'-ATTGTTTATTAAATGTTTTTTAG TT-3' (SEQ ID NO: 23) |
| AT3g271502ndMir2-R | 5'-CTAACAATTCCCAAAACCCTTAT C-3' (SEQ ID NO: 24) |
| *For PCR assay of MSHI-RNAi transgene:* | |
| RNAi-F | 5'-GTGTACTCATCTGGATCTGTATT G-3' (SEQ ID NO: 25) |
| RNAi-R | 5'-GGTTGAGGAGCCTGAATCTCTGA AC-3' (SEQ ID NO: 26) |

TABLE 11

Genome-wide 5-methylcytosine analysis in *Arabidopsis* Col-0 and MSH1-epiF3 plants.

| Background | CpG | CHG | CHH |
|---|---|---|---|
| Mapped | 4,382,312 | 4,749,451 | 19,727,351 |
| Methylated | 950,806 | 589,084 | 1,062,553 |
| DMPs | 91,150 | 10,324 | 1,789 |
| DMRs | 1,770 | 93 | 15 |

Plant phenotypes derived from crossing the MSH1-dr selections to wildtype did not appear to resemble those reported from other types of induced methylation changes, even though methylome changes were evident in the resulting populations. EpiRIL populations produced from crosses involving the *Arabidopsis* met1 mutant give rise to a variety of variant phenotypes (J. Reinders et al., Genes Dev. 23, 939 (2009). These earlier studies do not, however, report the enhanced vigor, markedly larger plant and stem size, or greater seed production that is seen with MSH1 manipulation.

The materials and methods used in this Example are as described below.

Plant Materials and Growth Conditions

*Arabidopsis* Col-0 and msh1 mutant lines were obtained from the *Arabidopsis* stock center and grown in metro mix with 12 hr daylight at 22° C. MSH1-epi lines were derived by crossing MSH1-dr lines with wild type plants. *Arabidopsis* plant biomass and rosette diameter were measured for 4-week-old plants. *Arabidopsis* flowering time was measured as date of first visible flower bud appearance. For hemi-complementation crosses, mitochondrial (AOX-MSH1) and plastid (SSU-MSH1) complemented homozygous lines were crossed to Columbia-0 wildtype plants. Each F1 plant was genotyped for transgene and the wildtype MSH1 allele and harvested separately. Three F2 families from AOX-MSH1×Col-0 and two F2 families from SSU-MSH1×Col-0 were evaluated for growth parameters. All families were grown under the same conditions, and biomass, rosette diameter and flowering time were measured. Two-tailed Student t-test was used to calculate p-values.

The sorghum germplasm used in these experiments was derived from Tx430, an inbred sorghum line (Miller, 1984). Several T3 sorghum siblings were derived from a single MSH1-dr plant, grown under greenhouse conditions and designated GAII1-GAII30. Each of the lines were confirmed to be transgene nulls. Six of them, GAII11, GAII15, GAII22, GAII24, GAII25, and GAII28 were used as females in crosses to wild type inbred Tx430 to derive F1 seed. Three additional plants, GAII22, GAII23, and GAII27 were used as males in reciprocal crosses. Day temperature in the greenhouse was 79 to 83° F., and night was 69 to 73° F. Plants were grown under short (10-hr) daylength.

F1 progenies were grown under the same greenhouse conditions, with progenies ranging in size from 5-19 individuals. Derived T4 progenies were grown from the six maternal msh1-dr plants used to derive F1s (GAII11, GAII15, GAII22, GAII24, GAII25, and GAII28), with populations ranging in size from 15-19 individuals. Self-pollinated seed of every F1 plant was harvested individually to derive the corresponding F2 families.

Field Experiments

During the summers of 2010 and 2011, F2 families were grown in two field experiments established under rainfed conditions at the Havelock Experiment Station of University of Nebraska in Lincoln. Experiments were arranged in an incomplete block design, with the 2010 experiment consisting of one replication with 15 blocks and 30 entries per block (30×15 alpha lattice). Individual lines were planted in a single panicle-per-row plan, with a single row plot of 5-m length and 0.75-m between-row spacing. The F3 seed was harvested from individual plants.

The 2011 experiment comprised seven blocks of 28 entries each (28×7 alpha lattice), with two replications fertilized with supplemental nitrogen at a dosage of 100 kg/ha. Forty eight samples from the 2010 experiment were selected to comprise the F3. These samples were derived from all six original crosses and included high and low F2 grain yield values. In addition, a greenhouse-grown subgroup of 17 F3 samples were selected, based on dry panicle weight, to derive F4 seed. Thus, the 2011 field experiment comprised 48, 77, and 42 entries corresponding to the F2, F3 and F4 generations, respectively, with wildtype Tx430 as control.

Sorghum Phenotypic Assessment

In 2010 and 2011 field experiments, the sorghum phenotypic traits recorded included plant height (PH), in cm from ground to panicle tip, panicle length (PL), in cm from panicle base to tip, fresh and dry panicle weight (FPW and DPW) (g), fresh and dry biomass yield (FBY and DBY) (g), and net grain yield (NGY) (g). Sample size for PH, PL, FPW, DPW and NGY varied from five to ten random, inner-row plants per row. Healthy, well-shaped heads were bagged before anthesis for selfing, and harvested after physiological maturity, when FPW was measured. The samples were dried at 80° F. for 30 days prior to measuring DPW and NGY. Biomass samples consisted of a three-plant sample, bagged and weighed after cutting to obtain FBW. Plants were random, inner-row selections, and samples were completely dried at 160° F. over 15 days for DBW.

PCR Assay for RNAi Transgene.

PCR assay for MSH1-RNAi transgene presence in sorghum materials used primers listed in Table S7. The reaction conditions were: 95° C. 5 min, 30 cycles of 95° C. 30 s, 55° C. 1 min, 72° C. 2 min; final extension was at 72° C. 10 min. Positive and negative controls were included from a confirmed transgenic line and wildtype Tx430, respectively.

Bisulfite Treated Genomic Library Construction and Sequencing

Arabidopsis genomic DNA (ca 15 ug) prepared from Col-0 and epi-F3 plants was sonicated to a peak range of 200 bp to 600 bp, phenol/chloroform purified and ethanol precipitated. Sonicated DNA (ca 12 ug) was treated with Mung Bean Nuclease (New England Biolabs), phenol/chloroform extracted and ethanol precipitated. Mung Bean Nuclease-treated genomic DNA (ca 3 ug) was end-repaired and 3' end-adenylated with Illumina Genomic DNA Samples Prep Kit (Illumina, San Diego Calif.). The adenylated DNA fragment was then ligated to methylation adapters (Illumina, San Diego, Calif.). Samples were then column purified and fractionated in agarose. A fraction of 280 bp to 400 bp was gel purified with the QIAquick Gel Purification kit (Qiagen, Valencia, Calif.). Another 3 ug of Mung Bean Nuclease treated genomic DNA was used to repeat the process, and the two fractions were pooled and subjected to sodium bisulfite treatment with the MethylEasy Xceed kit (Human Genetic Signatures Pty Ltd, North Ryde, Australia) according to manufacturer's instructions. Three independent library PCR enrichments were carried out with 10 ul from a total of 30 ul bisulfate treated DNA as input template. The PCR reaction mixture was 10 ul DNA, 5 ul of 10× pfuTurbo Cx buffer, 0.7 ul of PE1.0 primer, 0.7 ul PE2.0 primer, 0.5 ul of dNTP (25 mM), 1 ul of PfuTurbo Cx Hotstart DNA Polymerase (Stratagene, Santa Clara, Calif.), and water to a total volume of 50 ul. The PCR parameters were 950 C for 2 min, followed by 12 cycles of 950 C 30 sec, 650 C 30 sec and 720 C 1 min, then 720 C for 5 min. PCR product was column-purified and an equal volume from each PCR reaction was pooled together to a final concentration of 10 nM.

Libraries were DNA sequenced on the Illumina Genome Analyzer II with three 36-cycle TrueSeq sequencing kits v5 to read 116 nucleotides of sequence from a single end of each insert (V8 protocol).

Bisulfite Treatment of DNA for PCR Analysis

Arabidopsis genomic DNA was bisulfite treated using the MethylEasy Xceed kit according to manufacturer's instructions. PCR was performed using primers listed in Table S7, and the PCR products were cloned (Topo TA cloning kit, Invitrogen) and DNA-sequenced. Sequence alignment was performed using the T-Coffee multiple sequence alignment server (C Notredame, et al., J Mol Biol. 302:205-217, 2000).

DNA Sequence analysis and identification of differentially methylated cytosines (DMCs).

Fastq files were aligned to the TAIR10 reference genome using Bismark (F Krueger, S R Andrews. Bioinformatics 27:1571-1572 (2011), which was also used to determine the methylation state of cytosines. One mismatch was allowed in the first 50 nucleotides of the read. Bismark only retains reads that can be uniquely mapped to a location in the genome.

Only cytosine positions identified as methylated in at least two reads for at least one of the genotypes and sequenced at least four times in each of the genotypes were used for the identification of DMCs. For these cytosine positions, the number of reads indicating methylation or non-methylation for each genotype was tabulated using R (http://www.r-project.org). Fisher's exact test was carried out for testing differential methylation at each position. Adjustment for multiple testing over the entire genome was done as suggested in Storey and Tibshirani (J D Storey, R Tibshirani. Proc. Natl. Acad. Sci. USA 100:9440-9445 (2003) and a false discovery rate (FDR) of 0.05 was used for identifying differentially methylated cytosines. Methylome sequence data have been uploaded to the Gene Expression Omnibus with accession number GSE36783.

Mapping DMCs to genomic context and identifying differentially methylated regions (DMRs).

TAIR10 annotation (available on the internet ftp site "ftp.*arabidopsis*.org/home/tair/Genes/TAIR10_genome_release/TAIR10_gff3") was used to determine the counts for DMCs or nondifferentially methylated cytosines in gene coding regions, 5'-UTRs, 3'-UTRs, introns, pseudogenes, non-coding RNAs, transposable element genes, and intergenic regions. Intergenic regions were defined as regions not corresponding to any annotated feature.

For each methylation context (CpG, CHG, CHH), the genome was scanned for regions enriched in DMCs using a 1-kb window in 100-bp increments. Windows with at least four DMCs were retained and overlapping windows were merged into regions. Regions with at least 10 DMCs were retained with the boundary trimmed to the furthest DMCs in the region. Fisher's exact test was then performed for each region by merging all methylated/non-methylated read counts at all cytosine positions in the region. Adjusting for all tested regions, the FDR is controlled at 0.1.

Example 10

Summary Table of Nucleic Acid Sequences and SEQ ID NO

TABLE 12

| Nucleotide Sequences provided in the Sequence Listing | | |
|---|---|---|
| Internet Accession Information | SEQ ID NO | Comments |
| The Arabidopsis Information Resource (TAIR) 1009043787 on the internet (world wide web) at arabidopsis.org | 1 | *Arabidopsis* MSH1 Full length cDNA (DNA sequence) |
| The Arabidopsis Information Resource (TAIR) 1009118392 on the internet (world wide web) at arabidopsis.org | 2 | *Arabidopsis* MSH1 Protein (amino acid sequence) |
| NCBI AY856369 on the world wide web at ncbi.nlm.nih.gov/nuccore | 3 | Soybean MSH1 >gi\|61696668\|gb\|AY856369.1\| *Glycine max* DNA mismatch repair protein (MSH1) complete cds; (DNA sequence) |
| NCBI Accession AY856370 on the world wide web at ncbi.nlm.nih.gov/nuccore | 4 | *Zea mays* MSH1 gi\|61696670\|gb\|AY856370.1\| *Zea mays* DNA mismatch repair protein (MSH1), complete cds; (DNA sequence) |
| NCBI Accession AY866434.1 on the world wide web at ncbi.nlm.nih.gov/nuccore | 5 | Tomato MSH1 >gi\|61696672\|gb\|AY866434.1\| *Lycopersicon esculentum* DNA mismatch repair protein (MSH1), partial cds; (DNA sequence) |
| NCBI XM002448093.1 on the world wide web at ncbi.nlm.nih.gov/nuccore | 6 | *Sorghum* MSH1 >gi\|242076403:1-3180 *Sorghum bicolor* hypothetical protein; (DNA sequence) |
| Os04g42784.1 Rice Genome Annotation Project - MSU Rice Genome Annotation (Osa1) Release 6.1 Internet address rice.plantbiology.msu.edu/index.shtml | 7 | Rice (*Oryza sativa*) MSH1 coding sequence (DNA sequence) |
| *Brachypodium* Bradi5g15120.1 On the world wide web at gramene.org/Brachypodium_distachyon/Gene/Summary?db=core;g=BRADI5G15120;r=5:18500245-18518223;t=BRADI5G15120.1 | 8 | *Brachypodium* MSH1 coding region (DNA sequence) |
| GSVIVT01027931001 On the world wide web at genoscope.cns.fr/spip/Vitis-vinifera-e.html | 9 | *Vitis Vinifera* MSH1 cDNA (DNA sequence) |
| Cucsa.255860.1 On the internet (world wide web) at phytozome.net/ | 10 | Cucumber (*Cucumis sativa*) MSH1 coding sequence; (DNA sequence) |
| TOM-CD1F | 11 | Primer (DNA sequence) |
| TOM-CD1R | 12 | Primer (DNA sequence) |

TABLE 12-continued

Nucleotide Sequences provided in the Sequence Listing

| Internet Accession Information | SEQ ID NO | Comments |
|---|---|---|
| At4g02840 The Arabidopsis Information Resource (TAIR) on the internet (world wide web) at arabidopsis.org | 13 | second intron of the *Arabidopsis* small nuclear riboprotein (At4g02840); (DNA sequence) |
| GenBank Accession ES831813.1 on the world wide web at ncbi.nlm.nih.gov/nucest | 14 | Cotton (*Gossypium hirsutum*) MSH1 partial cDNA sequence (EST); (DNA sequence) |
| Primer zm-msf8 | 15 | Primer (DNA sequence) |
| Primer zm-msr8 | 16 | primer(DNA sequence) |
| AT5G67120RING-F | 17 | primer(DNA sequence) |
| AT5G67120RING-R | 18 | primer(DNA sequence) |
| AT1G20690SWI-F | 19 | primer(DNA sequence) |
| AT1G20690SWI-R | 20 | primer(DNA sequence) |
| AT3g271501stMir2-F | 21 | primer(DNA sequence) |
| AT3g271501stMir2-R | 22 | primer(DNA sequence) |
| AT3g271502ndMir2-F | 23 | primer(DNA sequence) |
| AT3g271502ndMir2-R | 24 | primer(DNA sequence) |
| RNAi-F | 25 | primer(DNA sequence) |
| RNAi-R | 26 | primer(DNA sequence) |
| AT3G27150 The Arabidopsis Information Resource (TAIR) on the internet (world wide web) at arabidopsis.org | 27 | DNA sequence |
| Col0-MIR2-2 | 28 | DNA sequence (bisulfite sequencing) |
| Col0-MIR2-3 | 29 | DNA sequence (bisulfite sequencing) |
| Col0-MIR2-4 | 30 | DNA sequence (bisulfite sequencing) |
| Col0-MIR2-5 | 31 | DNA sequence (bisulfite sequencing) |
| Col0-MIR2-6 | 32 | DNA sequence (bisulfite sequencing) |
| Col0-MIR2-10 | 33 | DNA sequence (bisulfite sequencing) |
| Col0-MIR2-11 | 34 | DNA sequence (bisulfite sequencing) |
| Col0-MIR2-12 | 35 | DNA sequence (bisulfite sequencing) |
| Col0-MIR2-26 | 36 | DNA sequence (bisulfite sequencing) |
| Col0-MIR2-27 | 37 | DNA sequence (bisulfite sequencing) |
| Col0-MIR2-28 | 38 | DNA sequence (bisulfite sequencing) |
| Col0-MIR2-29 | 39 | DNA sequence (bisulfite sequencing) |
| F3-Mir2-1 | 40 | DNA sequence (bisulfite sequencing) |
| F3-Mir2-2 | 41 | DNA sequence (bisulfite sequencing) |
| F3-Mir2-4 | 42 | DNA sequence (bisulfite sequencing) |
| F3-Mir2-5 | 43 | DNA sequence (bisulfite sequencing) |
| F3-Mir2-7 | 44 | DNA sequence (bisulfite sequencing) |
| F3-Mir2-11 | 45 | DNA sequence (bisulfite sequencing) |
| F3-Mir2-12 | 46 | DNA sequence (bisulfite sequencing) |
| F3-Mir2-15 | 47 | DNA sequence (bisulfite sequencing) |
| F3-Mir2-16 | 48 | DNA sequence (bisulfite sequencing) |
| F3-Mir2-27 | 49 | DNA sequence (bisulfite sequencing) |
| F3-Mir2-28 | 50 | DNA sequence (bisulfite sequencing) |

TABLE 12-continued

| Nucleotide Sequences provided in the Sequence Listing | | |
|---|---|---|
| Internet Accession Information | SEQ ID NO | Comments |
| *Brassica Locus* Bra015033 (Msh1 ortholog) Available on the internet (world wide web) at chibba.agtec.uga.edu/duplication/index/details?lc=Bra015033 | 51 | DNA sequence of the *Brassica rapa* Msh1 ortholog |
| Wheat Locus Q8RVT1 GenBank Accession No.: AF354709.1 Partial coding sequence Available on the internet (world wide web) at ncbi.nlm.nih.gov/nuccore/AF354709 | 52 | WHEAT MutS homolog 7 (Fragment) |

REFERENCES

Abdelnoor, R. V., Christensen, A. C., Mohammed, S., Munoz-Castillo, B., Moriyama, H. and Mackenzie, S. A. 2006. Mitochondrial genome dynamics in plants and animals: Convergent gene fusions of a MutS homolog. J. Molec. Evol. 63(2):165-73.

Abdelnoor, R. V., Yule, R., Elo, A., Christensen, A., Meyer-Gauen, G. and Mackenzie, S. 2003. Substoichiometric shifting in the plant mitochondrial genome is influenced by a gene homologous to MutS. Proc. Natl Acad. Sci. USA 100:5968-5973.

Arrieta-Montiel M P, Shedge V, Davila J, Christensen A C, Mackenzie S A. 2009. Diversity of the *Arabidopsis* mitochondrial genome occurs via nuclear-controlled recombination activity. Genetics 183:1261-8et al Bellaoui M, Martin-Canadell A, Pelletier G, Budar F. 1998. Low-copy-number molecules are produced by recombination, actively maintained and can be amplified in the mitochondrialgenome of Brassicaceae: relationship to reversion of the male sterile phenotype in some cybrids. Mol Gen Genet. 257:177-85

Buchanan BB, Balmer Y (2005). Redox Regulation: A Broadening Horizon. Annu Rev Plant Biol 56: 187-220.

Cokus, S J, Feng S, Zhang X, Chen Z, Merriman B, Haudenschild C D, Pradhan S, Nelson S F, Pellegrini M and Jacobsen S E (2008) Shotgun bisulphate sequencing of the *Arabidopsis* genome reveals DNA methylation patterning. Nature 452:215-219.

Davila, J., Arrieta-Montiel, M., Wamboldt, Y., Xu, Y.-Z., Mackenzie, S A. 2011. Double-strandbreak repair processes drive evolution of the mitochondrial genome in *Arabidopsis*. Theor Appl Genet. 2012 Mar. 18. [Epub ahead of print].

De Gara L, Locato V, Dipierro S, de Pinto M C (2010) Redox homeostasis in plants. The challenge of living with endogenous oxygen production. Respir Physiol Neurobiol. 173 Suppl:S13-9.

Fu J, Keurentjes J J B, Bouwmeester H, American T, Verstappen F W A, Ward J L, Beale M H, de Vos R C H, Dijkstra M, Scheltema R A, Johannes F, Koornneef M, Vreugdenhil D, Breitling R, Jansen R C (2009) System-wide molecular evidence for phenotypic buffering in *Arabidopsis*. Nature Genet 41:166-167.

Hanson, M. and Bentolila, S. 2004. Interactions of mitochondrial and nuclear genes that affect male gametophyte development. Plant Cell 16 (suppl.): S154-S169.

Hawes S M, Sapienza C, Latham K E (2002) Ooplasmic donation in humans: the potential for epigenetic modifications. Hum Reprod 17:850-2.

Hauben M, Haesendonckx B, Standaert E, Van Der Kelen K, Azmi A, Akpo H, Ven Breusegem F, Guisez Y, Bots M, Lambert B, Laga B, De Block M (2009) Energy use efficiency is characterized by an epigenetic component that can be directed through artificial selection to increase yield. Proc Natl Acad Sci USA 106:20109-20114.

Hruz T, Laule O, Szabo G, Wessendorp F, Bleuler S, Oertle L, Widmayer P, Gruissem W, Zimmermann P. (2008) Genevestigator v3: a reference expression database for the metaanalysis of transcriptomes. Adv Bioinformatics. 2008: 420747.

Ifuku K, Ishihara S, Sato F (2010). Molecular functions of oxygen-evolving complex family proteins in photosynthetic electron flow. J Integr. Plant Biol 52:723-734.

Jablonka E, Oborny B, Molnar I, Kisdi E, Holbauer J, et al. (1995) The adaptive advantage of phenotypic memory in changing environments. Philos Trans R Soc Lond B Biol Sci 350:133-141.

Janska, H., Sarria, R., Woloszynska, M., Arrieta-Montiel, M. and Mackenzie, S. 1998. Stoichiometric shifts in the common bean mitochondrial genome leading to male sterility and spontaneous reversion to fertility. Plant Cell 10:1163-1180.

Johannes F, Porcher E, Teixeira F K, Saliba-Colombani V, Simon M, Agier N, Bulski A, Albuisson J, Heredia F, Audigier P, Bouchez D, Dillmann C, Guerche P, Hospital F, Colot V (2009) Assessing the impact of transgenerational epigenetic variation on complex traits. PLoS Genet 5:1-11.

Johnson, C., Kasprzewska, A., Tennessen, K., Fernandes, J., Nan, G. L., Walbot, V., Sundaresan, V., Vance, V., and Bowman, L. H. (2009). Clusters and superclusters of phased small RNAs in the developing inflorescence of rice. Genome Res 19, 1429-1440.

Langmead B, Trapnell C, Pop M, Salzberg S L (2009) Ultrafast and memory-efficient alignment of short DNA sequences to the human genome. Genome Biol 10:R25.

Lister R, Pelizzola M, Dowen R H, Hawkins R D, Hon G, Tonti-Filippini J, Nery J R, Lee L, Ye Z, Ngo Q-M, Edsall L, Antosiewicz-Bourget J, Stewart R, Ruotti V, Millar A H, Thomson J A, Ren B, Echer J R (2009). Human DNA methylomes at base resolution show widespread epigenomic differences. Nature 462:315-322.

Llorente B, Smith C E, Symington L S 2008. Break-induced replication: What is it and what is it for? Cell Cycle 7:859-864.

Mackenzie, S A. 2011. Male sterility and hybrid seed production. In A. Altman and P. M. Hasegawa (eds). Plant Biotechnology and Agriculture: Prospects for the 21st Century, Elsevier Publ, in press.

McCauley D E and Olson M S 2008 Do recent findings in plant mitochondrial molecular and population genetics have implications for the study of gynodioecy and cytonuclear conflict? Evolution 62:1013-1025.

Pfannschmidt, T. (2010) Plastidial retrograde signaling—a true "plastid factor" or just metabolite signatures? Trends Plant Sci 15:427-435.

Redei, G. P. 1973. Extra-chromosomal mutability determined by a nuclear gene locus in *Arabidopsis*. Mutat. Res. 18, 149-162.

Reik, W., Walter J (2000) Genomic imprinting: parental influence on the genome. Nature Rev Genet 2: 21-32.

Sandhu, A. S., Abdelnoor, R. V. and Mackenzie, S. A. 2007. Transgenic induction of mitochondrial rearrangements for cytoplasmic male sterility in crop plants. Proc Natl Acad Sci USA. 104:1766-70.

Shedge, V., Arrieta-Montiel, M., Christensen, A. C. and Mackenzie, S. A. 2007. Plant mitochondrial recombination surveillance requires novel RecA and MutS homologs. Plant Cell 19:1251-1264.

Shedge V, Davila J, Arrieta-Montiel M P, Mohammed S, Mackenzie S A. 2010. Extensive rearrangement of the *Arabidopsis* mitochondrial genome elicits cellular conditions for thermotolerance. Plant Physiol. 152:1960-70.

Smiraglia D J, Kulawiec M, Bistulfi G L, Gupta S G, Singh K K (2008) A novel role for mitochondria in regulating epigenetic modification in the nucleus. Cancer Biol Ther. 7: 1182-1190.

Vaughn, M W, Tanurd IcM, Lippman Z, Jiang H, Carrasquillo R, et al. (2007) Epigenetic natural variation in *Arabidopsis thaliana*. PLoS Biol 5:e174.

Xu Y-Z, Arrieta-Montiel M P, Wamboldt Y J, Virdi K, De Paula W B M, Widhalm J R, Basset G J, Davila J I, Elthon T E, Elowsky C G, Sato S J, Clemente T E and Mackenzie S A, (2011). MSH1 is a multi-functional protein in plants that alters mitochondrial and plastid properties and response to high light. Manuscript submitted.

Wang, X., Elling, A. A., Li, X., Li, N., Peng, Z., He, G., Sun, H., Qi, Y., Liu, X. S., and Deng, X. W. (2009). Genome-wide and organ-specific landscapes of epigenetic modifications and their relationships to mRNA and small RNA transcriptomes in maize. Plant Cell 21, 1053-1069.

Waters M T, Wang P, Korkaric M, Capper R G, Saunders N J, Langdale J A. (2009) Plant Cell. 21:1109-28.

Zhang, X, Shiu S, Cal A, Borevitz J O (2008) Global analysis of genetic, epigenetic and transcriptional polymorphisms in *Arabidopsis thaliana* using whole genome tiling arrays. PLoS Genet 4:e1000032.

Having illustrated and described the principles of the present invention, it should be apparent to persons skilled in the art that the invention can be modified in arrangement and detail without departing from such principles.

Although the materials and methods of this invention have been described in terms of various embodiments and illustrative examples, it will be apparent to those of skill in the art that variations can be applied to the materials and methods described herein without departing from the concept, spirit and scope of the invention. All such similar substitutes and modifications apparent to those skilled in the art are deemed to be within the spirit, scope and concept of the invention as defined by the appended claims.

What is claimed is:

1. A method for producing a plant exhibiting improved yield comprising the steps of:
   a. suppressing expression of endogenous MSH1 gene(s) in a plant or plant cell to obtain a first parental plant, wherein suppression of MSH1 expression is effected with: (i) a transgene comprising a polynucleotide of at least 19 nucleotides in length and having at least 90% sequence identity to the endogenous MSH1 gene(s) of the plant or plant cell; (ii) a mutation in the endogenous MSH1 gene(s); or (iii) a nucleic acid of at least 19 nucleotides in length and having at least 90% sequence identity to the endogenous MSH1 gene(s);
   b. selfing the first parental plant or crossing the first parental plant to a second parental plant;
   c. recovering progeny plants or a progeny plant line from the self or cross of the first parental plant of step (b) wherein MSH1 function is restored; and,
   d. selecting a progeny plant or a progeny plant line from a recovered progeny plant or plant line of step (c) or from a self or outcross of a recovered progeny plant or plant line of step (c) wherein the selected progeny plant or plant line exhibits improved yield in comparison to a control plant, wherein said improved yield is associated with one or more epigenetic changes in the nucleus of the progeny plant cells relative to the corresponding parental chromosomal loci and is heritable.

2. The method of claim 1, wherein at least one of said epigenetic changes is methylation of chromosomal DNA.

3. The method of claim 1, wherein said method further comprises the step of producing seed by: i) selfing the selected progeny plant or plant line of step (d), ii) outcrossing the selected progeny plant or plant line of step (d) or, iii) both selfing and outcrossing the selected progeny plant or plant line of step (d).

4. The method of claim 3, wherein said method further comprises the step of assaying said seed or plants grown from said seed for the presence of improved yield.

5. The method of claim 1, wherein said first parental plant or plant cell comprises a mutation or a transgene that can suppress expression of MSH1.

6. The method of claim 1, wherein said first parental plant or plant cell is obtained by crossing a female plant with a distinct male plant, wherein at least one of said female or male plants comprise a mutation or a transgene that suppresses expression of the endogenous MSH1 gene of said parental plant(s), and wherein said plants were isogenic inbred lines prior to introduction of said transgene.

7. The method of claim 1, wherein said first parental plant or plant cell was isogenic to said second parental plant prior to suppression of MSH1 in said first parental plant or plant cell.

8. The method of claim 1, wherein said improved yield is not caused by substoichiometric shifting (SSS) in mitochondria of said progeny plant.

9. The method of claim 1, wherein said selected progeny plant or plant line in step (d) exhibit an improvement in yield in comparison to a control plant that had not been subjected to suppression of MSH1 expression but was otherwise isogenic to said first parental plant or plant cell.

10. The method of claim 1, wherein said plant is a crop plant is selected from the group consisting of corn, soybean, cotton, canola, wheat, rice, tomato, tobacco, millet, potato, and sorghum.

11. The method of claim 10, wherein said crop plant is sorghum and said yield improvement comprises increased panicle length, increased panicle weight, increased dry biomass, and combinations thereof.

12. The method of claim 1, wherein MSH1 had not been suppressed in said second parental plant.

13. The method of claim 1, wherein said first parental plant or plant cell is obtained by crossing a female plant with a distinct male plant, wherein at least one of said female or male plants comprise a mutation or a transgene that suppresses expression of the endogenous MSH 1 gene of said parental plant(s), and wherein said plants were isogenic lines prior to introduction of said transgene.

14. The method of claim 1, wherein suppression of MSH1 expression is effected with a transgene comprising an MSH1 gene sequence or fragment thereof having at least 18 contiguous nucleotides of sequence identity to the endogenous MSH1 gene(s), a mutation in the endogenous MSH1 gene(s), or a nucleic acid comprising an MSH1 gene sequence or fragment thereof having at least 18 contiguous nucleotides of sequence identity to the endogenous MSH1 gene(s).

* * * * *

SEQUENCE LISTING

```
<160> NUMBER OF SEQ ID NOS: 52

<210> SEQ ID NO 1
<211> LENGTH: 3730
<212> TYPE: DNA
<213> ORGANISM: Arabidopsis thaliana

<400> SEQUENCE: 1
agaggactgt gagattgtga attgcatagt cgtcgtcttc tggcgggaaa agaagcccta      60
gaaaaagggt gaaaggtgaa aactctactt cttcttcttc ttcttcttca gagtgtgaga     120
gagatgcatt ggattgctac cagaaacgcc gtcgtttcat tcccaaaatg gcggttcttc     180
ttccgctcct catatcgcac ttactcttcc ctcaaaccct cctccccaat tctacttaat     240
agaaggtact ctgaggggat atcttgtctc agagatggaa agtctttgaa aagaatcaca     300
acggcttcta agaaagtgaa gacgtcaagt gatgttctca ctgacaaaga tctctctcat     360
ttggtttggt ggaaggagag attgcagaca tgtaagaaac catctactct tcagcttatt     420
gaaaggctta tgtacaccaa tttacttggt ttggaccta gcttgaggaa tggaagttta      480
aaagatggaa acctcaactg ggagatgttg cagtttaagt caaggtttcc acgcgaagtt     540
ttgctctgca gagtaggaga attttatgag gctattggaa tagatgcttg tatacttgtt     600
gaatatgctg gtctcaatcc ttttggtggt cttcgatcag atagtattcc aaaggctggc     660
tgcccaatta tgaatcttcg acagactttg gatgacctga cacgcaatgg ttattcagtg     720
tgtattgtgg aggaagttca ggggccaaca ccagcacgct cccgtaaagg tcgatttatt     780
tcagggcatg cacatccagg aagtcctat gtatatgggc ttgtcggtgt tgaccatgat     840
cttgactttc ctgatcctat gcctgttgtt gggatatctc gttcagcaag ggggtattgt     900
```

```
atgatatcta ttttcgagac tatgaaagca tattcgctag atgatggtct aacagaagaa    960
gccttagtta ccaagctccg cactcgtcgc tgtcatcatc ttttcttaca tgcatcgttg   1020
aggcacaatg catcagggac gtgccgctgg ggagagtttg gggaaggggg tctactctgg   1080
ggagaatgca gtagcaggaa ttttgaatgg tttgaaggag atactctttc cgagctctta   1140
tcaagggtca agatgttta tggtcttgat gatgaagttt cctttagaaa tgtcaatgta   1200
ccttcaaaaa atcggccacg tccgttgcat cttggaacgg ctacacaaat tggtgcctta   1260
cctactgaag gaataccttg tttgttgaag gtgttacttc catctacgtg cagtggtctg   1320
ccttcttttgt atgttaggga tcttcttctg aaccctcctg cttacgatat tgctctgaaa   1380
attcaagaaa cgtgcaagct catgagcaca gtaacatgtt caattccaga gtttacctgc   1440
gtctcttctg ctaagcttgt gaagcttctt gagcaacggg aagccaacta cattgagttc   1500
tgtcgaataa aaaatgtgct tgatgatgta ttacatatgc atagacatgc tgagcttgtg   1560
gaaatcctga attattgat ggatcctacc tgggtggcta ctggtttgaa aattgacttt   1620
gacacttttg tcaacgaatg tcattgggcg tctgatacaa ttggtgaaat gatctcttta   1680
gatgagaatg aaagtcatca gaatgtaagt aaatgtgaca atgtcccgaa cgaattcttt   1740
tatgatatgg agtcttcatg gcgaggtcgc gttaaggaa ttcatataga ggaagaaatc   1800
actcaagtag aaaaatcagc tgaggctta tctttagcag tagctgagga ttttcaccct   1860
attatatcaa gaattaaggc caccactgct tcacttggtg gcccgaaagg cgaaatcgca   1920
tatgcaagag agcatgagtc tgtttggttc aaggggaaac ggtttacgcc atctatctgg   1980
gctggtactg caggggaaga ccaaataaaa cagctgaaac ctgccttaga ctcgaaagga   2040
aaaaggttg gagaagaatg gtttacgacc ccaaaggtgg aaattgcttt agtcagatac   2100
catgaagcta gtgagaatgc aaaagctcgg gtgttggaac tgttgcgcga gttatccgtt   2160
aaattgcaaa caaaaataaa tgttcttgtc tttgcatcta tgcttctggt catttcaaaa   2220
gcattatttt cccatgcttg tgaagggaga aggcgaaagt gggtttttcc aacgcttgtc   2280
ggattcagtt tagatgaggg cgcaaaacca ttagatggtg ccagtcgaat gaagctgaca   2340
ggcctgtcac cttattggtt tgatgtatct tctggaaccg ctgttcacaa taccgttgac   2400
atgcaatcac tgtttcttct aactggacct aacggtggtg gtaaatcgag tttgctcaga   2460
tcaatatgcg cagctgctct acttggaatt ccggttttaa tggttccagc tgaatcagct   2520
tgtattcctc actttgattc catcatgctt cacatgaaat catatgacag ccctgtagac   2580
ggaaaaagtt ctttccaggt agaaatgtcg gaaatacgat ctattgtaag ccaggctact   2640
tcgagaagcc tagtgcttat agatgagata tgccgaggga cagagacagc aaaaggcacc   2700
tgtatcgctg gtagtgtggt agagagtctt gacacaagtg gttgtttggg tattgtatct   2760
actcatctcc atggaatctt cagtttacct cttacagcga aaacatcac atataaagca   2820
atgggagccg aaaatgtcga agggcaaacc aagccaactt ggaaattgac agatggagtc   2880
tgcagagaga gtcttgcgtt tgaaacagct aagagggaag tgttcccga gtcagttatc   2940
caaagagctg aagctctta cctctcggtc tatgcaaaag acgcatcagc tgaagttgtc   3000
aaacccgacc aaatcataac ttcatccaac aatgaccagc agatccaaaa accagtcagc   3060
tctgagagaa gtttggagaa ggacttagca aaagctatcg tcaaaatctg tgggaaaaag   3120
atgattgagc tgaagcaat agaatgtctt tcaattggtg ctcgtgagct tccacctcca   3180
tctacagttg gttcttcatg cgtgtatgtg atgcggagac ccgataagag attgtacatt   3240
ggacagaccg atgatcttga aggacgaata cgtgcgcatc gagcaaagga aggactgcaa   3300
```

```
gggtcaagtt ttctatacct tatggttcaa ggtaagagca tggcttgtca gttagagact    3360
ctattgatta atcaactcca tgaacaaggc tactctctgg ctaacctagc cgatggaaag    3420
caccgtaatt tcggaacgtc ctcaagcttg agtacatcag acgtagtcag catcttatag    3480
tttgaaacat tagctgtgtt tgtagttgat catctctatg tgcaattgaa caagtcagtt    3540
tgctagaact agagtagatt actaagaaac catgccgttt ttcattttga gattttgcaa    3600
aacggcatgc agttcgggta agtcggatgc cgcaattacc aatttgggt cagtctgtgt    3660 aattgtcgtt tcataaatcc gattaacgtg tactttgaac aaaactcagc agtaaacttc    3720
tttattcatc                                                          3730

<210> SEQ ID NO 2
<211> LENGTH: 1118
<212> TYPE: PRT
<213> ORGANISM: Arabidopsis thaliana

<400> SEQUENCE: 2
```

| | | | | | | | | | | | | | | |
|---|---|---|---|---|---|---|---|---|---|---|---|---|---|---|
| Met | His | Trp | Ile | Ala | Thr | Arg | Asn | Ala | Val | Ser | Phe | Pro | Lys | Trp |
| 1 | | | | 5 | | | | | 10 | | | | | 15 |
| Arg | Phe | Phe | Arg | Ser | Ser | Tyr | Arg | Thr | Tyr | Ser | Ser | Leu | Lys | Pro |
| | | | 20 | | | | | 25 | | | | | 30 | |
| Ser | Ser | Pro | Ile | Leu | Leu | Asn | Arg | Arg | Tyr | Ser | Glu | Gly | Ile | Ser | Cys |
| | | 35 | | | | | 40 | | | | | 45 | | |
| Leu | Arg | Asp | Gly | Lys | Ser | Leu | Lys | Arg | Ile | Thr | Thr | Ala | Ser | Lys | Lys |
| | 50 | | | | | 55 | | | | | 60 | | | | |
| Val | Lys | Thr | Ser | Ser | Asp | Val | Leu | Thr | Asp | Lys | Asp | Leu | Ser | His | Leu |
| 65 | | | | | 70 | | | | | 75 | | | | | 80 |
| Val | Trp | Trp | Lys | Glu | Arg | Leu | Gln | Thr | Cys | Lys | Lys | Pro | Ser | Thr | Leu |
| | | | | 85 | | | | | 90 | | | | | 95 | |
| Gln | Leu | Ile | Glu | Arg | Leu | Met | Tyr | Thr | Asn | Leu | Leu | Gly | Leu | Asp | Pro |
| | | | 100 | | | | | 105 | | | | | 110 | | |
| Ser | Leu | Arg | Asn | Gly | Ser | Leu | Lys | Asp | Gly | Asn | Leu | Asn | Trp | Glu | Met |
| | | 115 | | | | | 120 | | | | | 125 | | | |
| Leu | Gln | Phe | Lys | Ser | Arg | Phe | Pro | Arg | Glu | Val | Leu | Leu | Cys | Arg | Val |
| | 130 | | | | | 135 | | | | | 140 | | | | |
| Gly | Glu | Phe | Tyr | Glu | Ala | Ile | Gly | Ile | Asp | Ala | Cys | Ile | Leu | Val | Glu |
| 145 | | | | | 150 | | | | | 155 | | | | | 160 |
| Tyr | Ala | Gly | Leu | Asn | Pro | Phe | Gly | Gly | Leu | Arg | Ser | Asp | Ser | Ile | Pro |
| | | | | 165 | | | | | 170 | | | | | 175 | |
| Lys | Ala | Gly | Cys | Pro | Ile | Met | Asn | Leu | Arg | Gln | Thr | Leu | Asp | Asp | Leu |
| | | | 180 | | | | | 185 | | | | | 190 | | |
| Thr | Arg | Asn | Gly | Tyr | Ser | Val | Cys | Ile | Val | Glu | Glu | Val | Gln | Gly | Pro |
| | | 195 | | | | | 200 | | | | | 205 | | | |
| Thr | Pro | Ala | Arg | Ser | Arg | Lys | Gly | Arg | Phe | Ile | Ser | Gly | His | Ala | His |
| | 210 | | | | | 215 | | | | | 220 | | | | |
| Pro | Gly | Ser | Pro | Tyr | Val | Tyr | Gly | Leu | Val | Gly | Val | Asp | His | Asp | Leu |
| 225 | | | | | 230 | | | | | 235 | | | | | 240 |
| Asp | Phe | Pro | Asp | Pro | Met | Pro | Val | Val | Gly | Ile | Ser | Arg | Ser | Ala | Arg |
| | | | | 245 | | | | | 250 | | | | | 255 | |
| Gly | Tyr | Cys | Met | Ile | Ser | Ile | Phe | Glu | Thr | Met | Lys | Ala | Tyr | Ser | Leu |
| | | | 260 | | | | | 265 | | | | | 270 | | |
| Asp | Asp | Gly | Leu | Thr | Glu | Glu | Ala | Leu | Val | Thr | Lys | Leu | Arg | Thr | Arg |
| | | 275 | | | | | 280 | | | | | 285 | | | |

-continued

```
Arg Cys His His Leu Phe Leu His Ala Ser Leu Arg His Asn Ala Ser
    290                 295                 300
Gly Thr Cys Arg Trp Gly Glu Phe Gly Glu Gly Leu Leu Trp Gly
305                 310                 315                 320
Glu Cys Ser Ser Arg Asn Phe Glu Trp Phe Glu Gly Asp Thr Leu Ser
                325                 330                 335
Glu Leu Leu Ser Arg Val Lys Asp Val Tyr Gly Leu Asp Asp Glu Val
            340                 345                 350
Ser Phe Arg Asn Val Asn Val Pro Ser Lys Asn Arg Pro Arg Pro Leu
        355                 360                 365
His Leu Gly Thr Ala Thr Gln Ile Gly Ala Leu Pro Thr Glu Gly Ile
    370                 375                 380
Pro Cys Leu Leu Lys Val Leu Leu Pro Ser Thr Cys Ser Gly Leu Pro
385                 390                 395                 400
Ser Leu Tyr Val Arg Asp Leu Leu Asn Pro Ala Tyr Asp Ile
                405                 410                 415
Ala Leu Lys Ile Gln Glu Thr Cys Lys Leu Met Ser Val Thr Cys
            420                 425                 430
Ser Ile Pro Glu Phe Thr Cys Val Ser Ser Ala Lys Leu Val Lys Leu
        435                 440                 445
Leu Glu Gln Arg Glu Ala Asn Tyr Ile Glu Phe Cys Arg Ile Lys Asn
    450                 455                 460
Val Leu Asp Asp Val Leu His Met His Arg His Ala Glu Leu Val Glu
465                 470                 475                 480
Ile Leu Lys Leu Leu Met Asp Pro Thr Trp Val Ala Thr Gly Leu Lys
                485                 490                 495
Ile Asp Phe Asp Thr Phe Val Asn Glu Cys His Trp Ala Ser Asp Thr
            500                 505                 510
Ile Gly Glu Met Ile Ser Leu Asp Glu Asn Glu Ser His Gln Asn Val
        515                 520                 525
Ser Lys Cys Asp Asn Val Pro Asn Glu Phe Phe Tyr Asp Met Glu Ser
    530                 535                 540
Ser Trp Arg Gly Arg Val Lys Gly Ile His Ile Glu Glu Glu Ile Thr
545                 550                 555                 560
Gln Val Glu Lys Ser Ala Glu Ala Leu Ser Leu Ala Val Ala Glu Asp
                565                 570                 575
Phe His Pro Ile Ile Ser Arg Ile Lys Ala Thr Ala Ser Leu Gly
            580                 585                 590
Gly Pro Lys Gly Glu Ile Ala Tyr Ala Arg Glu His Glu Ser Val Trp
        595                 600                 605
Phe Lys Gly Lys Arg Phe Thr Pro Ser Ile Trp Ala Gly Thr Ala Gly
    610                 615                 620
Glu Asp Gln Ile Lys Gln Leu Lys Pro Ala Leu Asp Ser Lys Gly Lys
625                 630                 635                 640
Lys Val Gly Glu Glu Trp Phe Thr Thr Pro Lys Val Glu Ile Ala Leu
                645                 650                 655
Val Arg Tyr His Glu Ala Ser Glu Asn Ala Lys Ala Arg Val Leu Glu
            660                 665                 670
Leu Leu Arg Glu Leu Ser Val Lys Leu Gln Thr Lys Ile Asn Val Leu
        675                 680                 685
Val Phe Ala Ser Met Leu Leu Val Ile Ser Lys Ala Leu Phe Ser His
    690                 695                 700
Ala Cys Glu Gly Arg Arg Arg Lys Trp Val Phe Pro Thr Leu Val Gly
```

-continued

```
            705                 710                 715                 720
        Phe Ser Leu Asp Glu Gly Ala Lys Pro Leu Asp Gly Ala Ser Arg Met
                        725                 730                 735
        Lys Leu Thr Gly Leu Ser Pro Tyr Trp Phe Asp Val Ser Ser Gly Thr
                        740                 745                 750
        Ala Val His Asn Thr Val Asp Met Gln Ser Leu Phe Leu Leu Thr Gly
                        755                 760                 765
        Pro Asn Gly Gly Lys Ser Ser Leu Leu Arg Ser Ile Cys Ala Ala
        770                 775                 780
        Ala Leu Leu Gly Ile Ser Gly Leu Met Val Pro Ala Glu Ser Ala Cys
        785                 790                 795                 800
        Ile Pro His Phe Asp Ser Ile Met Leu His Met Lys Ser Tyr Asp Ser
                        805                 810                 815
        Pro Val Asp Gly Lys Ser Ser Phe Gln Val Glu Met Ser Glu Ile Arg
                        820                 825                 830
        Ser Ile Val Ser Gln Ala Thr Ser Arg Ser Leu Val Leu Ile Asp Glu
                        835                 840                 845
        Ile Cys Arg Gly Thr Glu Thr Ala Lys Gly Thr Cys Ile Ala Gly Ser
                        850                 855                 860
        Val Val Glu Ser Leu Asp Thr Ser Gly Cys Leu Gly Ile Val Ser Thr
        865                 870                 875                 880
        His Leu His Gly Ile Phe Ser Leu Pro Leu Thr Ala Lys Asn Ile Thr
                        885                 890                 895
        Tyr Lys Ala Met Gly Ala Glu Asn Val Glu Gly Gln Thr Lys Pro Thr
                        900                 905                 910
        Trp Lys Leu Thr Asp Gly Val Cys Arg Glu Ser Leu Ala Phe Glu Thr
                        915                 920                 925
        Ala Lys Arg Glu Gly Val Pro Glu Ser Val Ile Gln Arg Ala Glu Ala
                        930                 935                 940
        Leu Tyr Leu Ser Val Tyr Ala Lys Asp Ala Ser Ala Glu Val Val Lys
        945                 950                 955                 960
        Pro Asp Gln Ile Ile Thr Ser Ser Asn Asn Asp Gln Ile Gln Lys
                        965                 970                 975
        Pro Val Ser Ser Glu Arg Ser Leu Glu Lys Asp Leu Ala Lys Ala Ile
                        980                 985                 990
        Val Lys Ile Cys Gly Lys Lys Met Ile Glu Pro Glu Ala Ile Glu Cys
                        995                 1000                1005
        Leu Ser Ile Gly Ala Arg Glu Leu Pro Pro Ser Thr Val Gly
                        1010                1015                1020
        Ser Ser Cys Val Tyr Val Met Arg Arg Pro Asp Lys Arg Leu Tyr
                        1025                1030                1035
        Ile Gly Gln Thr Asp Asp Leu Glu Gly Arg Ile Arg Ala His Arg
                        1040                1045                1050
        Ala Lys Glu Gly Leu Gln Gly Ser Ser Phe Leu Tyr Leu Met Val
                        1055                1060                1065
        Gln Gly Lys Ser Met Ala Cys Gln Leu Glu Thr Leu Leu Ile Asn
                        1070                1075                1080
        Gln Leu His Glu Gln Gly Tyr Ser Leu Ala Asn Leu Ala Asp Gly
                        1085                1090                1095
        Lys His Arg Asn Phe Gly Thr Ser Ser Ser Leu Ser Thr Ser Asp
                        1100                1105                1110
        Val Val Ser Ile Leu
                        1115
```

<210> SEQ ID NO 3
<211> LENGTH: 3765
<212> TYPE: DNA
<213> ORGANISM: Glycine max

<400> SEQUENCE: 3

| | | | | | |
|---|---|---|---|---|---|
| gtcagataca | gagtccttcc | ctcctcgtgt | gtggactgtg | gcgggaactc | attttgctag | 60 |
| tttgcttcct | ctctctctct | cgttcccatt | caacgcaatg | tacagggtag | ccacaagaaa | 120 |
| cgtcgccgtt | ttcttccctc | gttgctgttc | cctcgcgcac | tacactcctt | ctctatttcc | 180 |
| cattttcact | tcattcgctc | cctctcgttt | ccttagaata | aatggatgtg | taaagaatgt | 240 |
| gtcgagttat | acggataaga | aggtttcaag | ggggagtagt | agggccacca | agaagcccaa | 300 |
| aataccaaat | aacgttttag | atgataaaga | ccttcctcac | atactgtggt | ggaaggagag | 360 |
| gttgcaaatg | tgcagaaagt | tttcaactgt | ccagttaatt | gaaagacttg | aattttctaa | 420 |
| tttgcttggc | ctgaattcca | acttgaaaaa | tggaagtctg | aaggaaggaa | cactcaactg | 480 |
| ggaaatgttg | caattcaagt | caaaatttcc | acgtcaagta | ttgctttgca | gagttgggga | 540 |
| attctatgaa | gctgggggaa | tagatgcttg | tattcttgtt | gaatatgtgg | gtttaaatcc | 600 |
| cattggtggt | ctgcgatcag | atagtatccc | aagagctagt | tgtcctgtcg | tgaatcttcg | 660 |
| gcagacttta | tgatgatctga | caacaaatgg | ttattcagtg | tgcattgtgg | aggaggctca | 720 |
| gggcccaagt | caagctcgat | ccaggaaacg | tcgctttata | tctgggcatg | ctcatcctgg | 780 |
| aaatccctat | gtatatggac | ttgctacagt | tgatcatgat | cttaactttc | cagaaccaat | 840 |
| gcctgtagta | ggaatatctc | attctgcgag | gggttattgc | attaatatgg | tactagagac | 900 |
| catgaagaca | tattcttctg | aagattgctt | gacagaagaa | gcagttgtta | cgaagcttcg | 960 |
| tacttgccaa | tatcattact | tatttttgca | tacatccttg | aggcggaatt | cttgtggaac | 1020 |
| ctgcaactgg | ggagaatttg | gtgagggagg | gctattatgg | ggagaatgta | gttctagaca | 1080 |
| ttttgattgg | tttgatggca | accctgtctc | cgatcttttg | gccaaggtaa | aggaacttta | 1140 |
| tagtattgat | gatgaggtta | cctttcggaa | cacaactgtg | tcttcaggac | atagggctcg | 1200 |
| accattaact | cttggaacat | ctactcaaat | tggtgccatt | ccaacagaag | gaataccttc | 1260 |
| tttgttgaag | gttttacttc | catcaaattg | caatggatta | ccagtattgt | acataaggga | 1320 |
| acttcttttg | aatcctcctt | catatgagat | tgcatccaaa | attcaagcaa | catgcaaact | 1380 |
| tatgagcagt | gtaacgtgtt | caattccaga | atttacatgt | gtttcgtcag | caaagcttgt | 1440 |
| aaagctactt | gaatggaggg | aggtcaatca | tatggaattt | tgtagaataa | agaatgtact | 1500 |
| ggatgaaatt | ttgcagatgt | atagtacctc | tgagctcaat | gaaatattga | acatttaat | 1560 |
| cgagcccaca | tggtggcaa | ctgggttaga | aattgacttt | gaaaccttgg | ttgcaggatg | 1620 |
| tgagatcgca | tctagtaaga | ttggtgaaat | agtatctctg | gatgatgaga | atgatcagaa | 1680 |
| aatcaactcg | ttctcttta | ttcctcacga | atttttgag | gatatggagt | ctaaatggaa | 1740 |
| aggtcgaata | aaaagaatcc | acatagatga | tgtattcact | gcagtggaaa | aagcagctga | 1800 |
| ggccttacat | atagcagtca | ctgaagattt | tgttcctgtt | gtttctagaa | taaaggctat | 1860 |
| tgtagcccct | ctcggaggtc | ctaagggaga | aatatcttat | gctcgggagc | aagaagcagt | 1920 |
| ttggttcaaa | ggcaaacgct | ttacaccgaa | tttgtgggct | ggtagccctg | agaggaaca | 1980 |
| aattaaacag | cttaggcatg | ctttagattc | taaaggtaga | aaggtagggg | aggaatggtt | 2040 |
| taccacacca | aaggtcgagg | ctgcattaac | aaggtaccat | gaagcaaatg | ccaaggcaaa | 2100 |

```
agaaagagtt ttggaaattt aagggggact cgctgctgag ttgcaataca gtataaacat    2160
tcttgtcttt tcttccatgt tgcttgttat tgccaaagct ttatttgctc atgcaagtga    2220
agggagaaga aggagatggg tctttcccac gcttgtagaa tcccatgggt ttgaggatgt    2280
gaagtcattg gacaaaaccc atgggatgaa gataagtggt ttattgccat attggttcca    2340
catagcagaa ggtgttgtgc gtaatgatgt tgatatgcaa tcattatttc tgttgacagg    2400
accgaatggt ggtgggaaat caagtttttct taggtcaatt tgtgctgctg cactacttgg    2460
gatatgtgga ctcatggttc ctgcagaatc agccctaatt ccttattttg actccatcac    2520
gcttcatatg aagtcatatg atagtccagc tgataaaaag agttcctttc aggttgaaat    2580
gtcagaactt cgatccatca ttggcggaac aaccaacagg agccttgtac ttgttgatga    2640
aatatgccga ggaacagaaa ctgcaaaagg acttgcattt gctggtagca tcattgaaac    2700
ccttgatgga attgggtgtc tgggtattgt atccactcac ttgcatggaa tatttacttt    2760 gccctaaac aaaaaaaaca ctgtgcacaa agcaatgggc acaacatcca ttgatggaca    2820
aataatgcct acatggaagt tgacagatgg agtttgtaaa gaaagtcttg cttttgaaac    2880
ggctaagagg gaaggaattc ctgagcatat tgttagaaga gctgaatatc tttatcagtt    2940
ggtttatgct aaggaaatgc ttttttgcaga aaatttccca aatgaagaaa gttttctac    3000 ctgcatcaat gttaataatt tgaatggaac acatcttcat tcaaaaaggt tcctatcagg    3060
agctaatcaa atggaagttt tacgcgagga agttgagaga gctgtcactg tgatttgcca    3120
ggatcatata aaggacctaa aatgcaaaaa gattgcattg gagcttactg agataaaatg    3180
tctcataatt ggtacaaggg agctaccacc tccatcggtt gtaggttctt caagcgtcta    3240
tgtgatgttc agaccagata agaaactcta tgtaggagag actgatgatc tcgagggacg    3300
ggtccgaaga catcgattaa aggaaggaat gcatgatgca tcattccttt atttcttgt    3360 cccaggtaaa agcttggcat gccaatttga atctctgctc atcaaccaac tttctggtca    3420
aggcttccaa ctgagcaata tagctgatgg taaacatagg aattttggca cttccaacct    3480
gtatacataa ctagtctata gacattgata ttatctacct caatcgcgta ttttgcctc    3540 ttttaaatgg ctcaaagact tcaatcatcg atgttaagtt taggaaacaa tgtctgcagc    3600 attttgtta gaattagttg ctgcagctgc atttatgtcc acatcttcaa gtgtggaaat    3660
tcttgttcat tagcttgtaa gtacaaaagt gtttgtgtac gtttggagtc ccgagagaat    3720
atacaagtac aaatgaacaa atatattagt aatgaatgca ctaga              3765

<210> SEQ ID NO 4
<211> LENGTH: 3642
<212> TYPE: DNA
<213> ORGANISM: Zea mays

<400> SEQUENCE: 4
gcgcactacc ccgagaaacg tgcgacggga acctccgcgg ttccccaagt tcgcctcctt      60
cactactctc gcgccccggc acgcctgaaa accccaccc ctcctgccgc tccgcctctc     120
ccatcacttc ccacgcccct cgccgcctcc cattccagcg tggacacgac gccactcgcc     180
agcacggaga cgcgcgcctc gaagcactac tgcactagcc agccgtcgtt cttccgcgcc     240
ggcgccatgc accgggtgct cgtgagctcg cttgtggccg ccacgccgcg atggctgccc     300
ctcgccgact ccatcctccg gcgccgccgg ccgcgctgct cccctcttcc cgtgctgatg     360
ttcgatcgga gggcttggtc caagccaagg aaggtctcac gaggcatttc agtgcgtcc     420 aggaaagcta acaaacaggg agaatactgt gatgaaagta tgctgtcgca tatcatgtgg     480
```

```
tggaaagaga aaatggagag gtgcagaaaa ccatcatcca tacaattgac tcagaggctt    540
gtgtattcaa atatattagg gttggatccg aatttaagaa acggaagctt gaaagatgga    600
accctgaaca tggagatttt ggtatttaaa tcaaaatttc ctcgtgaggt tctactttgc    660
agagtaggag atttctatga agctatcggt tttgatgcct gtattctcgt agagcatgca    720
ggcttaaatc cttttggagg tttgcgttcc gacagtattc ctaaagctgg tgtccagtc     780 gtgaatttac ggcagacatt ggatgatttg actcgatgtg ttattccgt gtgcatagtc     840 gaggaaattc aaggcccaac tcaagcccgt gctcggaaaa gtcgatttat ttctgggcat    900
gcccatcctg gtagtcctta tgtatttggt cttgctgaag tagaccatga tgtagagttc    960
cctgatccga tgcctgttgt tgggatttca cattctgcaa aaggttattg cttgatatct   1020
gtgctagaga caatgaaaac ttattcagct gaggagggct taacagagga ggctattgtt   1080
actaagctcc gcatatgtcg ttatcaccat ctataccttc acaattcttt gaagaataat   1140
tcttcaggga catcacgctg gggtgaattc ggtgaaggtg ggctcttgtg gggagagtgc   1200
agtgggaagt cctttgagtg gtttgacggt tcacctattc aagaacttt atgcaaggta    1260 cgggaaatat atggccttga tgagaaaacg gttttcgcg atgtcaccgt ctcattggaa    1320
ggcaggcccc aacctcttca tcttgggact gctactcaaa ttggagtcat accaactgag   1380
ggaataccga gtttgttaag aatggtgctt ccttcaaatt gtggcgggct tccatcaatg   1440
tatattagag atcttcttct taatcctcca tcatttgagg ttgcagcagc gatccaagag   1500
gcttgcaggc ttatgggcaa cataacctgc tccattcctg aatttacatg catatcagca   1560
gcaaagcttg tgaaactact tgagtcgaaa ggggtcaatc acattgaatt ttgtagaata   1620
aaaaatgtcc ttgatgagat tatgctcatg aacagggatg ctgagctttc tgcaatcctg   1680
catgaattac tggtacctgc ttctgtggct actggtttca aagttgaagc tgatatgcta   1740
atgaacggat gtagcattat ttcacaacga atagctgaag tgatttcttt aggtgttgaa   1800
agtgatcagg caataacttc attggaatat attccaaagg agttcttcaa tgatatggag   1860
tcatcttgga aggggcgcgt gaaaaggatc catgctgaag aagagtttgc aaatgttgat   1920
agggctgctg aggcattatc aattgcggtc attgaagatt ttatgccaat tatttcgagg   1980
gtgaaatctg tagtgtcctc gaatggaggt ttgaaaggag aaatcggtta tgcaaaagaa   2040
catgaagctg tttggtttaa aggaaagaga ttcataccaa atgtatgggc taacacacct   2100
ggtgagcagc aaataaaaca actgaagcct gcaattgatt caaaaggcag aaaggttggg   2160
gaggaatggt ttacaacaag caaagttgag aatgctttag ccaggtacca tgaagcttgt   2220
gataatgcaa gaaataaagt tcttgagctg ttgagaggcc tttctagtga attgcaggac   2280
aaaattaaca tacttgtctt ttgctcaaca ctgctcatca ttgcaaaagc acttttggt    2340 catgttagtg aggctcgaag aagaggttgg atgcttccta ctatatctcc cttatcaaag   2400
gactgtgttg tggaggaaag ttcaagtgca atggatttag taggactatt tccttactgg   2460
cttgatgtta atcaaggaaa tgcaatattg aatgatgtcc acatgcactc tttatttgtt   2520
cttactggcc caaatggtgg tgtaaatct agcatgttgc gatcagtctg tgcagctgtg   2580
cttcttggaa tatgtggcct gatggtacct tcaacttcag ctgtaatccc acattttgat   2640
tccattatgc tgcatatgaa agcctatgat agcccagcag atgggaaaag ttcatttcag   2700
attgaaatgt cggagatacg tgctttagtc agccgagcta ctgctaggag tcttgttctg   2760
attgatgaaa tatgtagagg cacagaaact gcaaaaggaa catgtatagc tggtagcatc   2820
```

```
attgaaagac ttgataatgt tggctgccta ggcatcatat caactcacct gcatgggatt   2880
ttcgacctgc ctctctcact tagcaacact gatttcaaag ctatgggaac tgaagtggtc   2940
gatggatgca ttcatccaac atggaaactg attgatggca tatgtagaga aagccttgct   3000
tttcaaacag caaggaggga aggcatgcct gacttgataa tcaccagggc tgaggagcta   3060
tatttgagta tgagtacaaa taacaagcag ggagcatcag tggcgcacaa tgagcctcct   3120
aatggcagcc ccagtgtaaa tggcttggtt gaggagcctg aatctctgaa gaacagacta   3180
gaaatgctgc ctggtacctt tgagccgctg cggaaggaag ttgagagtgc tgttactacg   3240
atgtgtaaga aaatactgtc ggacctttac aacaaaagta gcatcccaga actggtcgag   3300
gtggtctgcg ttgctgtagg tgctagagag caaccaccgc cttccactgt tggcagatct   3360
agcatctacg tgattatcag aagcgacaac aggctctatg ttggacagac ggacgatctt   3420
ctggggcgct tgaacgccca cagatcgaag gaaggcatgc gggacgctac ggtattatac   3480
gtcttggtcc ctggcaagag cgttgcctgc cagctggaaa cccttctcat aaaccagctc   3540
ccttcgaggg gcttcaagct catcaacaag gcagacggga agcacaggaa cttcggtata   3600
tctcgaatct ctggcgaggc agttgctact ggacggaact ag                      3642

<210> SEQ ID NO 5
<211> LENGTH: 3373
<212> TYPE: DNA
<213> ORGANISM: Lycopersicon esculentum

<400> SEQUENCE: 5
atgtattggg ttacggcaaa aaacgtcgtc gtttcagttc ccgttggcg ttcactgtcc     60
cttttcctcc gtccaccact tcgccggcgt ttcttatctt tctctccaca tactctgtgc    120
cgagagcaga tacgttgcgt gaaggagcgg aagttttttg ccacaacggc aaaaaaactc    180
aaacaaccaa aaagtattcc agaggaaaaa gactatgtta atattatgtg gtggaaagag    240
agaatggaat tcttgagaaa gccttcttcc gctcttctgg ctaagaggct tacatattgt    300
aacttgctgg gtgtggatcc gagtttgaga atggaagtc ttaaagaggg aacacttaac     360
tcggagatgt tgcagttcaa gtcaaaattt ccacgtgaag ttttgctctg tagagtaggt   420
gattttatg aagctattgg attcgatgct tgtattcttg tggaatatgc tggtttaaat    480
ccatttggtg gcctgcactc agatagtata ccaaaagctg gttgtccagt gtgaatcta    540
agacagacgc ttgatgatct cacacgtaat ggtttctctg tgtgcgtcgt ggaggaagtt   600
cagggtccaa ctcaagctcg tgctcgtaag agtcgattta tatcagggca tgcacatcca   660
ggcagtccct atgttttttgg ccttgttgga gatgatcaag atcttgattt tccagaacca  720
atgcctgttg ttggaatatc ccgttcagcg aaggggtatt gcattatctc tgtttacgag   780
actatgaaga cttactctgt ggaagatggc ctaactgaag aagccgtagt caccaaactt   840
cgtacttgtc gatgccatca tttttttttg cataattcat tgaagaacaa ttcctcagga   900
acatcgcgtt ggggagagtt tggtgaaggt ggacttttgt ggggagaatg taatgctaga   960
cagcaggaat ggttggatgg caatcctatc gatgagcttt tgttcaaggt aaaagagctt  1020
tatggtctca atgatgacat tccattcaga aatgtcactg ttgtttcaga aaataggccc  1080
cgtcctttac accttggaac tgccacacaa attggtgcta ttccaaccga agggattcca  1140
tgttttgttaa aggtgttgct tcctcctcat tgcagtggtc taccagtcct gtatattagg  1200
gatcttcttt taaatccacc agcctatgag attcttcag acattcaaga ggcatgcaga   1260
cttatgatga gtgtcacatg ttcaattcct gattttacct gtatttcatc tgcaaagctg  1320
```

```
gtcaagctgc ttgagttgag ggaggcaaat cacgttgagt tctgcaaaat aaagagcatg    1380
gtcgaagaga tactgcagtt gtatagaaat tcagagcttc gtgctattgt agagttactg    1440
atggatccta cttgggtggc aactgggttg aaagttgatt ttgatacact agtaaatgaa    1500
tgtggaaaga tttcttgtag aatcagtgaa ataatatccg tacatggtga aaatgatcaa    1560
aagattagtt cctatcctat catcccaaat gatttctttg aagatatgga gttgttgtgg    1620
aaaggccgtg tcaagaggat ccatttggag gaagcatatg cagaagtaga aaaggctgcg    1680
gatgctttat ctttagccat aacagaagat ttcctaccta ttatttcaag aataagggcc    1740
acgatggccc cacttggagg aactaaaggg gagattttgt atgcccgtga gcatggagct    1800
gtatggttta agggaaagag atttgtacca actgtttggg ctggaaccgc tggagaagaa    1860
caaattaagc aactcagacc tgctctagat tcaaagggga agaaggttgg agaagaatgg    1920
ttcactacaa tgagggtgga agatgcaata gctaggtatc acgaggcaag tgctaaggca    1980
aagtcaaggg tcttggaatt gctaagggga cttttcttctg aattactatc taagatcaat    2040
atccttatct ttgcatctgt cttgaatgtg atagcaaaat cattattttc tcatgtgagt    2100
gaaggaagaa gaagaaattg gattttccca caatcacac aatttaacaa atgtcaggac    2160
acagaggcac ttaatggaac tgatggaatg aagataattg gtctatctcc ttattggttt    2220
gatgcagcac gagggactgg tgtacagaat acagtagata tgcagtccat gtttctttta    2280
acaggtccaa atggtggggg caaatcaagc ttgctgcgtt cgttgtgtgc agctgcattg    2340
ctaggaatgt gtgggttcat ggttccagct gaatcagctg tcattcctca ttttgactca    2400
attatgctgc atatgaaatc atatgatagt cctgttgatg gaaaaagttc atttcagatt    2460
gaaatgtctg aaattcggtc tctgattact ggtgccactt caagaagtct tgtacttata    2520
gatgaaatat gtcgaggaac agaaacagca aagggacat gtattgctgg aagtgtcata    2580
gaaaccctgg acgaaattgg ctgtttggga attgtatcaa cccacttgca tggaatattt    2640
gatttacccc tgaaaatcaa gaagaccgtg tataaagcaa tgggagctga atatgttgac    2700
ggtcaaccaa taccaacttg gaaactcatt gatgggatct gtaaagagag tctagcattt    2760
gaaacagctc agagagaagg aattccagaa atattaatcc aaagagcaga agaattgtat    2820
aattcagctt acgggaatca gataccaagg aagatagacc aaataagacc tcttttgttca    2880
gatattgacc tcaatagcac agataacagt tctgaccaat taaatggtac aagacaaata    2940
gctttggatt ctagcacaaa gttaatgcat cgaatgggaa tttcaagcaa gaaacttgaa    3000
gatgctatct gtcttatctg tgagaagaag ttaattgagc tgtataaaat gaaaaatccg    3060
tcagaaatgc caatggtgaa ttgcgttctt attgctgcca gggaacagcc ggctccatca    3120
acaattggtg cttcaagtgt ctatataatg ctaagacctg acaaaaagtt gtatgttgga    3180
cagactgatg atcttgaggg cagagtacgt gctcatcgct tgaaggaggg aatggaaaac    3240
gcgtcattcc tatatttctt agtctctggc aagagcatcg cctgccaatt ggaaactctt    3300
ctaataaatc aacttcctaa tcatggtttt cagctaacaa acgttgctga tggtaagcat    3360
cgtaatttg gca                                                        3373
```

<210> SEQ ID NO 6
<211> LENGTH: 3180
<212> TYPE: DNA
<213> ORGANISM: Sorghum bicolor

<400> SEQUENCE: 6

```
atgcaccggg tgctcgtgag ctcgctcgtg gccgccacgc cgcggtggct ccccctcgcc      60
gactccatcc tccggcgccg ccgcccgcgc tgctctcctc ttcccatgct gctattcgac     120
cggagggctt ggtccaagcc aaggaaggtc tcacgaggca tctcagtggc gtctaggaaa     180
gctaacaaac agggagaata ttgtgatgaa agcatgctat cgcatatcat gtggtggaaa     240
gagaaaatgg agaagtgcag aaaaccatca tccgtacaat tgactcagag gcttgtgtat     300
tcaaatatat tagggttgga tccaaatcta agaaatggaa gcttgaaaga tggaaccctg     360
aacatggaga ttttgctatt taaatcaaaa tttcctcgtg aggttctact ttgcagagta     420
ggagacttct atgaagctat tggttttgat gcctgtattc tcgtagagca tgcaggctta     480
aatccttttg gaggtttgcg ttctgacagt atccctaaag ctgggtgtcc agtcgtgaat     540
ttacggcaga cattggatga tttgactcga tgtggttatt ctgtgtgcat agttgaggaa     600
attcaaggcc aacacaagc ccgttcccgg aaaagtcgat ttatttctgg gcatgcccat     660
cctggtagtc cttatgtatt tggtcttgct gaagtagacc atgatgtaga gttccctgat     720
ccgatgcctg ttgttgggat ttcacattct gcaaaaggtt attgcttgat atctgtgcta     780
gagacaatga aaacttattc agctgaggag ggcttaacag aagaggctat tgttactaag     840
ctccgcatat gtcgttatca tcatctatac cttcacaatt cttttgaagaa taattcttca     900 gggacatcac gctggggtga attcggtgaa ggagggctct tgtggggaga gtgcagtggg     960
aagtcctttg agtggtttga tggtttacct attgaagaac ttttatgcaa ggtacgggaa    1020
atatatggcc ttgatgagaa aactgttttt cgcaatgtca ccgtctcatt ggaaggcagg    1080
ccccaacctc tttatcttgg aactgctact caaattggag tcataccaac tgagggaata    1140
ccgagtttgc taaaaatggc actcccttca agttgtggcg ggcttccatc aatgtatatt    1200
agagatcttc ttcttaatcc tccatcattt gatgttgcgg cagcggtcca agaggcttgc    1260
aggcttatgg ggagcataac ttgttctgtt cctgaattta cttgcatatc acttgtgaag    1320
ctacttgagt ctaaagaggt caatcacatt gaattttgta gaataaaaaa tgtccttgat    1380
gagattatgc tcatgaacag gaatgctgag cttctgcaa tcctgaacaa attgctggta    1440
cctggttctg tggctactgg tttgaaagtt gaagctgata tgctagtcat tgaagatttt    1500
atgccaatta tttcaagggt gaaatctgta gtgtcctcaa atggaggttc gaaaggagaa    1560
atctgttatg caaagaaaca tgaagctgtt tggtttaaag gaaagcgatt cacaccaact    1620
gtatgggcta acacacctgg tgagcagcaa ataaaacaac tgaagcctgc aattgattcg    1680
aaaggcagaa aggttgggga ggaatggttt acaacaagca agttgagaa tgctttagcc    1740 aggtaccatg aagcttgtga taatgcaaga aataaagttg ttgagctgtt gagagggctt    1800
tcaagtgaat tgcaggacaa aattaacata cttgtctttt gctcaacact gctcatcatt    1860
gcaaaagcac tttttggtca tgttagtgag ctcggagaa gaggctggat gcttcctact    1920
atatttccct tgtcaaagga ctgtgttgca gaggaaagtt caaatgcaat ggatttagta    1980
ggactctttc cttactggct tgatgttaat caaggaaatg caatattgaa tgatgtccac    2040
atgcactctt tatttgttct tactggtcca aatggtggtg gtaaatctag tatgttgcga    2100
tcagtctgtg cagctgcgct gcttggaata tgtggcctga tggtaccttc aacttcagct    2160
gtaatcccgc attttgattc cattatgctg catatgaaag cctacgatag cccagccgat    2220
gggaaaagtt catttcagat tgaaatgtcg gagatacgtg cttagtcag ccgagctact    2280 gctaggagtc ttgtcctgat tgatgaaata tgtaggggca cagaaactgc aaaaggaacc    2340
tgtattgctg gtagcatcat cgaaaggctg gataatgttg gctgcctagg catcatatca    2400
```

| | |
|---|---|
| actcacctgc atgggatttt tgacttgcct ctctcactca gcactactga tttcaaagct | 2460 |
| atgggaactg aagtggtcga cgggtgcatt catccaacat ggaaactgat ggatggcatc | 2520 |
| tgtagagaaa gccttgcttt tcaaacagcc aggagggaag gcatgcctga gttcataatc | 2580 |
| agaagggctg aggagctata tttgactatg agtacaaata acaagcagac cgcatcaatg | 2640 |
| gtccacaatg agcctcgtaa tgacagcccc agtgtaaatg gcttggttga aagcctgaa | 2700 |
| tatctgaaat acagactaga aattctgcct ggtacctttg agccgttgcg gagggaagtt | 2760 |
| gagagtgctg ttactatgat atgcaagaaa aaactgttgg atctttacaa taaaagtagc | 2820 |
| atcccagaac tggttgaggt ggtctgtgtt gctgtaggtg ctagagagca accaccacct | 2880 |
| tccactgttg gcaggtctag catctatgtg attatcagaa gcgacaacaa gctttatgtt | 2940 |
| ggacagacgg atgatcttct ggggcgcctt cacgcccaca gatcgaagga aggcatgcag | 3000 |
| gatgctacga tattatacat cttggttcct ggcaagagcg ttgcctgcca gctggaaacc | 3060 |
| cttctcataa atcagcttcc ttcgaggggc ttcaagctca tcaacaaggc agacggaaag | 3120 |
| cataggaact tcggtatatc tcgaatctct ggagaggcaa tcgccaccca gctaaactaa | 3180 |

<210> SEQ ID NO 7
<211> LENGTH: 3399
<212> TYPE: DNA
<213> ORGANISM: Oryza sativa

<400> SEQUENCE: 7

| | |
|---|---|
| atggccattc agcggctgct cgcgagctcg ctcgtggccg ccacgccgcg gtggcttccc | 60 |
| gtcgccgccg actcgtttct ccggcgccgc caccgccctc gctgctcccc gctcccgcg | 120 |
| ctgctatttta acaggaggtc ctggtctaaa ccaaggaaag tctcacgaag catttccatt | 180 |
| gtgtctagga agatgaacaa acaaggagat ctctgtaatg aaggcatgct gccacatatt | 240 |
| ctgtggtgga agagaaaat ggagaggtgc aggaaaccat catcaatgca attgactcag | 300 |
| agacttgtgt attcaaatat tttaggattg gatccaactt taagaaatgg aagcttgaag | 360 |
| gatgaagcc tgaacacgga aatgttgcaa ttcaaatcga agtttcctcg tgaagttcta | 420 |
| cttttgcagag tgggagattt ctacgaggct gttgggtttg atgcatgtat ccttgtggag | 480 |
| catgcaggct aaatcctttt tggaggcttg cgttctgata gtattccaaa agctggatgt | 540 |
| ccagtcatga atttgcggca gacattggat gatttgactc gatgtggtta ctctgtgtgc | 600 |
| atagttgaag aaattcaagg cccaacccaa gctcgtgcta ggaaaggccg atttatttct | 660 |
| ggccatgcac atcctggtag tccttatgta tttggtcttg ctgaagtaga ccatgatgtt | 720 |
| gagttccctg atccaatgcc tgtagttggg atttcacgat ctgcaaaagg ctattgcctg | 780 |
| atttctgtgc tagagacaat gaaaacatat tcagctgagg agggcttaac agaggaagca | 840 |
| gttgttacta gcttcgcat atgccgttat catcatctat accttcatag ttctttgagg | 900 |
| aacaattctt caggcacatc acgctgggga gaatttggcg aaggtgggct attgtgggga | 960 |
| gagtgcagtg aaaatctttt tgagtggttt gatggtaatc ctattgaaga actgttatgc | 1020 |
| aaggtaaggg aaatatatgg gcttgaagag aagactgttt tccgtaatgt cagtgtctca | 1080 |
| ttggaaggga ggcctcaacc cttgtatctt ggaacagcta ctcaaattgg ggtgatacca | 1140 |
| actgagggaa tacccagttt gctaaaaatt gttctccctc caaactttgg tggccttcca | 1200 |
| tcattgtata ttagagatct tcttcttaac cctccatctt ttgatgttgc atcatcagtt | 1260 |
| caagaggctt gcaggcttat gggtagcata acttgctcga ttcctgaatt tacatgcata | 1320 |

```
ccggcagcaa agcttgtgaa attactcgag tcaaagagg ttaatcacat cgaattttgt      1380
agaataaaga atgtcctcga tgaggtgttg ttcatgggta gcaatgctga gctttctgct      1440
atcctgaata aattgcttga tcctgccgcc atagttactg ggttcaaagt tgaagccgat      1500
atactagtga atgaatgtag ctttatttca caacgtatag ctgaagtaat ctctttaggt      1560
ggtgaaagtg accaggcaat aacttcatct gaatatattc cgaaagagtt cttcaatgat      1620
atggagtcat cttggaaggg acgtgtaaaa agggtgcatg ctgaagagga gttctcaaat      1680
gttgatatag ctgctgaggc actgtcaaca gcggtcattg aagattttct gccaattatt      1740
tcaagagtaa aatctgtgat gtcctcaaat ggaagttcga agggagaaat cagttatgca      1800
aaagagcatg aatctgtttg gtttaaaggg aggcgattca caccaaatgt gtgggccaac      1860
actcctggtg aactacagat aaagcaattg aagcctgcaa ttgactcaaa aggtagaaag      1920
gtcggagaag aatggttcac cactatcaaa gttgagaatg ctttaaccag gtaccatgaa      1980
gcttgtgata atgcaaaacg taaagttctt gagttgttga gaggactttc aagtgaattg      2040
caggacaaga ttaatgtcct tgtcttttgc tcaacgatgc tcatcataac aaaagcactt      2100
tttggtcatg ttagtgaagg acgaagaagg ggttgggtgc ttcctactat atctcccttg      2160
tgtaaggata atgttacaga ggaaatctca agtgaaatgg aattgtcagg aacttttcct      2220
tactggcttg atactaacca agggaatgca atactgaatg atgtccatat gcactctttg      2280
tttattctta ctggtccaaa cggtggtggt aaatccagta tgctgagatc agtctgtgct      2340
gctgcattac ttggaatatg tggcctgatg gtgccagctg cttcagctgt catcccacat      2400
ttcgattcca tcatgctgca tatgaaagca tatgatagcc cagctgatgg taaaagttcg      2460
tttcagattg aaatgtcaga gatacgatct ttagtctgcc gagctacagc taggagtctt      2520
gttctaattg atgaaatatg taggggcaca gaaacagcaa aaggaacatg tatagctggt      2580
agcatcattg aaagactcga taatgttggc tgcataggca tcatatcaac tcatttgcat      2640
ggcatttttg accttccact gtcactccac aatactgatt tcaaagctat gggaaccgaa      2700
atcatcgata ggtgcattca gccaacatgg aaattaatgg atggcatctg tagagagagt      2760
cttgcttttc aaacagccag gaaagaaggt atgcctgact tgataattag aagagctgag      2820
gaactatatt tggctatgag cacaaacagc aagcagacat catcagctgt ccaccatgaa      2880
atatccatag ccaactctac tgtaaatagc ttggttgaga agcctaatta cctgagaaat      2940
ggactagagc ttcaatctgg ttccttcgga ttactaagaa aagaaattga gagtgttgtt      3000
accacaatat gcaagaagaa actgttggat ctctacaaca aaaggagcat ctcagaactg      3060
attgaggtgg tctgtgttgc tgtgggtgct agggagcaac ccccaccttc aactgttggc      3120
aggtccagca tttatgtaat tatcagacgt gacagcaagc tctatattgg acagacggat      3180
gatcttgtgg gtcgacttag tgctcacaga tcgaaggaag gtatgcagga tgccacgata      3240
ttatatattt tggtacctgg gaagagcatt gcatgccaac tggaaactct tctcataaat      3300
cagctacctt tgaaaggttt caagctcatc aacaaggcag atggcaagca tcgaaatttc      3360
ggtatatctc ttgtcccagg agaggcaatt gccgcatag                            3399
```

<210> SEQ ID NO 8
<211> LENGTH: 3381
<212> TYPE: DNA
<213> ORGANISM: Brachypodium distachyon

<400> SEQUENCE: 8

```
atgcagcggc ttctggcgag cacgatcgtg gccgccacgc cgcgttggct ccccctcgcc        60
```

```
gactctatcg tccggcgccg ccgcccgcgc cgttccccgc tccccgtcct gctattccac    120
agatcattgt acaaaccaag gaaggtttca cgaggcatta caatggtgtc taataaggtg    180
aacaaacagg gagatctctg caatgaaggc atgctgtcac atattatgtg gtggaaagag    240
aaaatggaga gctgcaggaa accatcatct gtgcagttga ctcagagact tgtgtactct    300
aatatattag ggttggatcc aactttaagg aatggaagct taaagatgg  aaccctgaac    360 atggagatgt tacaatttaa atcaaagttt ccacgtgagg tcctactttg cagagtagga    420
gatttctatg aagccattgg gtttgatgcc tgcattcttg tagagcatgc aggcctaaat    480
ccttttgggg gcttgcgttc tgacagtatt ccaaaagctg gatgtccaat catgaatttg    540
cggcaaacat tggatgattt gactcggtct ggttattctg tgtgcatagt tgaggaaatt    600
caaggcccaa ctcaagcccg tgctcggaaa ggtcgattta tctctggcca tgcgcatcct    660
ggcagtcctt atgtatttgg tcttgctgaa gtagatcatg atcttgagtt tcctgaccca    720
atgcctgtag ttgggatttc acgctctgca aaaggctatt gcttgatttc tgtgctagag    780
acgatgaaaa cttattcagc tgaggagggc ctaacagaag aagctgtagt gactaagctg    840
cgcatatgcc gttatcatca tctataccct cacagttctt tgaggaataa ttcttcaggg    900
acatcacgct gggggggaatt cggagaggga ggactcttgt ggggagagtg cagtggaaag    960
tgttttgaat ggtttgatgg ttctcctatt gaggaacttt tatgcaaggt aagggagata   1020
tatgggctgg atgagaaaac taatttccgc aatgtcactg tctcattgga agggaggcct   1080
caacctttat atcttggaac tgctactcaa attggagtga tacaaacgga gggaattccc   1140
agtttactaa aaatgctact ccctccaaac tatggcgggc ttccatcaat gtatatcaga   1200
gatcttcttc ttaatcctcc atcttttgat gtcgcgtctg caattcagga ggcttgcagg   1260
cttatgggca gcataacttg ttcgattcct gaatttactt gcataccatc agcgaagctt   1320
gtgaaattac tcgagtcaaa agaggttaat cacattgaat tttgtagaat aaagaatgtc   1380
cttgatgaca ttatattaat gaatggaaac actgagcttt ctgctatcat ggacaaattg   1440
ctcgaacctg cttcggtggt tactggttttg aaagttgatg ctgatatact aattagagaa   1500
tgtagcctta tctcacaacg tataggtgaa gtcatctctt taggtgggga aagcgatcag   1560
gcaataactt catcggaata tattcccaag gagttcttta atgatatgga gtcatcttgg   1620 aagggggcgtg tgaaaagggt tcatgctgaa gaagagttca caaatgtcga tgtagctgct   1680
gaagcattat caaccgcggt aactgaagat tttctgccaa ttattgtaag agttaaatct   1740
gtgatatctt cacatggagg ttctaaaggg gaaatctctt atgcaaaaga acacgaaget   1800 gtttggttta aagggaagcg attcacacca aatgtctggg cgaacacacc tggtgaacaa   1860
cagataaaac aactaaagcc tgcgattgat tcaaaggta gaaaagttgg ggaggaatgg   1920
tttacaacaa tcaaagttga gaatgcttta gccaggtatc atgaagcttg tgatagtgca   1980
aaaggcaaag ttcttgagct gttgagaggt ctttcaagtg aattgcagga caagattaat   2040
atacttgtct tctgctcgac gctgctcatc atagcaaaag cacttttttgg tcatgttagc   2100 gagggtctta aagggggttg ggtgcttcct gccatatctc ccctatctaa ggactatagt   2160
actgaagaag gctcaagtga atggattta  ttgagactct ttccttactg gcttgacagt   2220
aatcaaggga atgcaatact gaatgatgtc aatatgcact ctttgtttat tctgactggc   2280
ccaaatggtg gaggtaaatc cagtatgttg cgatcagtct gtgcagctgc attgcttgga   2340
atatgtggtc tgatggtgcc agctgcttca gctgtcatcc cacactttga ttccatcatg   2400
```

```
ctgcatatga aggcctatga tagcccagct gatgggaaaa gttcgtttca gattgaaatg    2460
tcagagatcc gatctttagt cagccgtgct actggtagga gtcttgttct cattgatgaa    2520
atatgtaggg gcacagaaac tgcaaaagga acttgtatag ctggtagcat catcgaaagg    2580
ctcgacgatg ttggctgcct aggcatcata tcaacccatt tgcatggcat ttttgacttg    2640
cctctgtcac tcggcaatac tgatttcaaa gctatgggaa cagaagttgt caatgggtgc    2700
attcagccaa catggagatt aatggatggt atctgtagag aaagccttgc ttttcaaaca    2760
gcaaggaagg aaggtatgcc tgacttgata attaaaagag cagaggagct atacagtact    2820
atgggcagaa gcaagacgtc atcaacagtc caccatggtc catccgttgc taagtctaaa    2880
gcaagtggat tggttgatat gcctgatggt ctgggaaatg gattagaact tccatctggt    2940
gcttttgcac tgctgcgaaa ggatgtcgaa ataattgtga ccgcaatatg caaggataaa    3000
ttgttggatc tctacaacaa aagaagcatc tcagagctgg ttgaggtggt ttgtgttact    3060
gtaggtgcta gggagcaacc gccaccttca actgttggca ggtccagcat ctacatagtt    3120
atcaggcgtg acaacaagct ctatgttgga cagacggatg atcttgttgg ccgtcttgct    3180
gttcatagat ccaaggaagg tatgcagggt gccacaatat tatatatcgt ggttcctggc    3240
aagagcgttg cgtgccagct ggagacactt ctcataaacc agcttccctc gaaaggtttt    3300
aagctcacga caaggcaga tgcaagcat cggaacttcg gcatgtctgt tatctctgga    3360
gaagccattg ctgcacactg a                                              3381

<210> SEQ ID NO 9
<211> LENGTH: 3520
<212> TYPE: DNA
<213> ORGANISM: Vitis vinifera

<400> SEQUENCE: 9
atgtactggc tgtcaaccaa aaacgtcgtc gtttcattcc ctcgattcta ctctctcgct      60
cttcttctcc gttcccctgc ctgcaaatac acttcatttc gttcttctac acttctactc     120
caacagtttg agaagagccg atgtctcaac gaaaggaggg ttttgaaagg agctggaaga     180
atgacaaaaa atgttatagg attgcaaaat gagctagatg aaaaggatct ttctcacata     240
atgtggtgga aggagaggat gcaaatgtgt aaaaagccgt ccactgtcca ccttgttaaa     300
aggcttatat attccaattt gctaggagtg gatcctaact tgaaaaatgg gaatctaaaa     360
gaaggaacgc tgaactggga gatgttgcag ttcaagtcaa agtttcctcg tgaagtttta     420
ctctgcagag taggggattt ttatgaagcc atcggaattg atgcttgtat tcttgttgaa     480
tatgctggtt tgaatccttt tggtggtttg cgctcagaca gtataccaag agctggctgc     540
ccagtcatga atctacgaca aactttggat gacctgacac gtagcgggta ttcagtttgc     600
atagtggagg aagttcaggg tccaactcaa gctcgttctc gtaaaggtcg ttttatctct     660
gggcatgcgc atccgggtag tccttatgta tttggacttg ttggggttga tcatgatctt     720
gattttccag aaccaatgcc tgtagttgga atttctcgtt ctgcgaaggg ttattctata     780 atttagtcc ttgagactat gaagacgttt tcagtagagg atggtctgac agaagaggct     840
ttagttacca agcttcgcac ttgtcactac catcatttat tgctgcatac atctctgaga     900
cgcaactcct caggtacttg tcgttgggga gaatttggtg agggaggact attatgggga     960
gaatgtagtg ctagacactt tgaatggttt gaagggggatc ctgtatctca acttttgttt    1020
aaggtgaagg agctctatgg ttttgatgat caagttacat ttagaaatgt cactgtgtct    1080
tcagagaaaa gaccccgttc tttacacctt ggcacagcta cacaaattgg tgccatacca    1140
```

```
acagagggca taccgtgttt gttaaaggtg ttgcttccat caaattgcac tggtctacct    1200
cttttgtatg ttagagatct tcttctcaac cctcctgctt atgagattgc atccataatt    1260
caagcaacat gcagactcat gaacaatgta acgtgctcga ttcctgagtt tacttgtgtt    1320
tccctgcaa agcttgtgaa gctacttgag cttagggagg ctaatcatat tgagttctgc    1380
agaataaaaa gtgtacttga tgaaatattg cagatgcata gaaactctga tcttaacaaa    1440
atccttaaat tattgatgga tcctacctgg gtggcaactg gattgaagat tgactttgac    1500
acattggtga acgaatgtga atggatttca gctagaattg gtaaaatgat ctttcttgat    1560
ggtgaaaatg atcaaaagat aagttaccat cctatcattc caaatgactt ttttgaggac    1620
atggaatctc cttggaaggg tcgtgtgaag aggatccatg tagaagaagc atttgctgaa    1680
gtggaaagag cagctgaggc attatcttta gctatctccg aagatttcct acctattatt    1740
tcaagaataa aagctaccac agccccactt ggaggtccaa aaggagaagt tgtatatgct    1800
cgagagcatg aagctgtttg gttcaaggga aaacgttttg caccagttgc atgggcaggt    1860
actccagggg aagaacaaat taagcagctt agacctgcta tagattcaaa aggtagaaag    1920
gttggattgg aatggtttac cacagtgaag gtggaggatg cactaacaag gtaccatgag    1980
gctggggaca aggcaaaagc aagggtcttg gaattgttga ggggactttc tgcggagtta    2040
caaactaaaa ttaacatcct tatctttgct tccatgttgc ttgtcattgc aaaggcatta    2100
tttgctcatg tgagtgaagg gagaagaagg aaatgggttt tcccctctct tgtagagttg    2160
cataggtcta aggacatgga acctctggat ggagctaatt ggatgaagat aactggttta    2220
tcaccatatt ggttggacgt ggcacaaggc agtgctgtgc ataatacagt tgatatgaaa    2280
tcattgtttc ttttgacagg acctaatggg ggtggtaaat caagtttgct tcgatcaatt    2340
tgtgcagccg cattacttgg aatatgtgga tttatggtgc ctgcagaatc ggccttgatt    2400
cctcattttg attctattat gcttcacatg aaatcttatg atagcccagc tgatggaaaa    2460
agttcatttc agattgaaat gtcagagatg cgatccataa tcactggagc cacttcaaga    2520
agcctggtgc tgatagatga aatctgccga ggaacagaaa cagcaaaggg gacatgtatt    2580
gctggtagca tagttgaaac tcttgataag attggttgtc tgggtattgt atccactcac    2640
ttgcatggta tatttacctt gggactgaat actaagaatg ctatttgtaa agcaatggga    2700
actgaatatg ttgatggcaa aacaaaaccg acctggaagt tgatagatgg aatctgtaga    2760
gaaagccttg cctttgaaac agctcagaag gagggaattc ctgaaacaat tatccgaaga    2820
gcagaagagc tgtatctttc aatccattca aaagacttaa ttacagggg aactatttgt    2880
cctaaaattg agtcaacaaa tgaaatggaa gtcttacata gaaagttga gagtgcagtc    2940
accattgttt gccaaaagaa gctgaaggag ctctataagc agaaaaacac gtcaaaactt    3000
ccagagataa actgtgtggc cattttgcca ggggaacagc cgccgccatc aacaattggt    3060
gcttcaagtg tgtatgtgtt gtttagcact gataagaaac tttatgttgg agagacagat    3120
gatcttgaag gcagagtccg tgcgcatcga tcaaggaag gaatgcagaa ggcctcattc    3180
ctttattttg tggtcccagg gaagagcttg gcatgccaac tcgaaacgct tctcatcaac    3240
cagctccctg tccaggggtt ccaactggtc aatagagctg atggtaaaca tcgaaatttt    3300
ggcacattgg atcactccgt ggaagttgtg accttgcatc aatgagcctg cgctccttgc    3360
cacccatttt gtgaatggt tccatctttg aaatatgtac ttgaatgaca aaaccagat    3420
gaaagtggct gcagcaattt tggttttttg atgtacgttg ctccacttgc attagtatta    3480
```

| tctacctgat gaaatatgca ttgatattgc ttgctctaca | 3520 |

<210> SEQ ID NO 10
<211> LENGTH: 3615
<212> TYPE: DNA
<213> ORGANISM: Cucumis sativus

<400> SEQUENCE: 10

| atggaaatat ccatctatgt cgatgtggca ttgtggcggg aagtatcgga aaccaagggt | 60 |
| tttctgttcc ggcgacgacg agttacaaac accctcctca tttcaaacca aaacgcttta | 120 |
| aaacttccaa tcacaacaag attgaagctc acaaaccatc cattttatc caccgccatg | 180 |
| tactgggcgg caacacgaac cgttgtttct gcttcccggt ggcgttttct ggctcttttg | 240 |
| attcgcttcc ctccgcgtaa cttcacctca gttactcatt cgccggcatt tatagaaagg | 300 |
| caacagcttg aaaagttgca ctgttggaaa agcagaaaag gttcaagagg aagcatcaaa | 360 |
| gctgctaaga gtttaagga taataatatt ctccaagaca ataagtttct ttctcacatt | 420 |
| ttatggtgga aagagacggt ggaatcatgc aagaagccgt catctgtcca gctggttaag | 480 |
| aggcttgact tttccaactt gctaggttta gatacaaacc tgaaaaatgg gagtcttaaa | 540 |
| gaaggaactc ttaactgtga gattctacag ttcaaggcaa agtttcctcg agaagttttg | 600 |
| ctctgtagag ttggagattt ttatgaagca attggaatag atgcttgcat acttgtggaa | 660 |
| tatgctggtt taaatccttt tggaggtcag cgtatggata gtattccaaa agctggttgc | 720 |
| cccgttgtga atcttcgtca aactttggat gatctgacac gcaatgggtt ctcagtgtgc | 780 |
| atagtggaag aagttcaggg cccaattcaa gctcgttctc gcaaaggacg ttttatatct | 840 |
| gggcatgcac acccaggcag tccctatgtt tttgggcttg tcggggttga tcacgatctt | 900 |
| gactttccag aaccgatgcc tgtgattgga atatctcgat ccgcaagggg ctattgcatg | 960 |
| agccttgtca tagagaccat gaagacatat tcatcagagg atggtttgac agaagaggcc | 1020 |
| ttagttacta aactgcgcac ttgtcaatac catcattat ttcttcacac gtcattaagg | 1080 |
| aacaactcct caggcacttg ccgctggggt gaatttggtg agggtggccg gctatgggg | 1140 |
| gaatgtaatc ccagacattt tgagtggttc gatggaaagc ctcttgataa tcttatttct | 1200 |
| aaggttaaag agctttatgg tcttgatgat gaagttacat ttagaaatgt tacaatatcg | 1260 |
| tcagaaaata ggccacatcc gttaactcta ggaactgcaa cacagattgg tgccatacca | 1320 |
| acagagggaa taccttgttt gctgaaggtt ttgcttccat ccaattgtgc tggccttcct | 1380 |
| gcattgtata tgagggatct tcttctcaat cctcctgctt atgagactgc atcgactatt | 1440 |
| caagctatat gcaggcttat gagcaatgtc acatgtgcaa ttccagactt cacttgcttt | 1500 |
| cccccagcca agcttgtgaa gttattggaa acgagggagg cgaatcatat tgaattctgt | 1560 |
| agaatgaaga atgtacttga cgaaatatta caaatgcaca aaaattgcaa gctaaacaat | 1620 |
| atcctgaaat tgctgatgga tcctgcatct gtggcaactg ggttgaaaat tgactatgat | 1680 |
| acatttgtca acgaatgtga atgggcttcc agtagagttg atgaaatgat ttttcttggt | 1740 |
| agtgaaagtg aaagtgatca gaaaatcagt tcttatccta ttattcctaa tggttttttc | 1800 |
| gaggacatgg aattttcttg gaaaggtcgt gtgaagagga ttcacattga gaatcttgt | 1860 |
| acagaagttg aacgggcagc tgaagcactc tcccttgcag ttactgaaga ttttgtccca | 1920 |
| atcatttcta gaatcagggc tactaatgca ccactaggag gtccaaaggg agaaatatta | 1980 |
| tatgctcggg accatcaatc tgtctggttc aaaggaaaac ggtttgcacc atctgtatgg | 2040 |
| gctggaagcc ctggagaagc agaaattaaa caactgaaac ctgctcttga ttcaaaggga | 2100 |

```
aaaaaagttg gggaggagtg gtttaccacg aagaaggtgg aggattctt  aacaaggtac    2160 caagaggcca ataccaaagc aaaagcaaaa gtagtagatc tgctgaggga actttcttct    2220
gaattgttag ctaaaattaa cgtcctaata tttgcttcca tgctactcat aattgccaag    2280
gcgttatttg ctcatgtgag tgaagggagg aggaggaaat gggttttttcc cacccttgct   2340 gcacccagtg ataggtccaa ggggaaagtt gcgatgaagc tggttggtct atctccctat    2400
tggtttgatg ttgtcgaagg caatgctgtg cagaatacta ttgagatgga atcattattt    2460
cttttgactg gtccaaatgg gggtggaaaa tctagtttgc ttcgatcgat ttgtgctgct    2520
actttgcttg ggatatgtgg atttatggta ccggcagagt ccgccctgat tccccacttc    2580
gactcaatta tgcttcatat gaaatctttt gatagtcctg ctgatggaaa agttcttttt    2640
caggtggaaa tgtcagagat gagatccatt gtcaatagag taacggagag aagtcttgta    2700
cttatcgatg aaatctgtcg tggaacagaa acagcaaaag gaacttgtat tgccgggagc    2760
attattgaag ctcttgataa agcaggttgt cttggcattg tctccactca cttgcatgga    2820
atatttgatt tgcctttaga tacccaaaac attgtgtaca aagcaatggg aactgtttct    2880
gcggaaggac gcacggttcc cacttggaag ttgattagtg gaatatgtcg agagagcctt    2940
gcctttgaaa cagcaaagaa tgaaggaatc tctgaagcta taattcaaag ggctgaagat    3000
ttgtatctct caaattatgc taagaagggg atttcaggaa aagagacgac agatctgaac    3060
ttttttgttt cttctcatcc aagccttaat ggtaatggca ctggaaaatc caatctcaag    3120
tcaaacggtg tgattgtaaa ggctgatcag ccaaaaacag agacaactag caaaacaggt    3180
gtcttgtgga agaaacttga gagggctatc acaaagatat gccaaaagaa gttgatagag    3240
tttcatagag ataaaaacac attgacacct gctgaaattc aatgtgttct aattgatgca    3300
agagagaagc cacctccatc aacaataggt gcttcgagcg tatatgtgat tcttagaccg    3360
gatggcaaat tctatgttgg acagactgat gatctggatg gtagggtcca atcacatcgt    3420
ttaaaggaag gaatgcggga tgctgcattc ctttatctta tggtgcctgg gaagagctta    3480
gcttgccaac ttgaaactct tctcatcaat cgacttcctg atcacgggtt ccagctaact    3540
aacgttgctg atgaaaagca tcggaatttt ggcacagcca atctcttatc cgacaatgtg    3600 actgttgct catga                                                      3615
```

<210> SEQ ID NO 11
<211> LENGTH: 28
<212> TYPE: DNA
<213> ORGANISM: Artificial
<220> FEATURE:
<223> OTHER INFORMATION: synthetic

<400> SEQUENCE: 11

```
cgcaggtatc acgaggcaag tgctaagg                                         28
```

<210> SEQ ID NO 12
<211> LENGTH: 54
<212> TYPE: DNA
<213> ORGANISM: Artificial
<220> FEATURE:
<223> OTHER INFORMATION: synthetic

<400> SEQUENCE: 12

```
atccccaaac agccaatttc gtccaggatc cccaaacagc caatttcgtc cagg            54
```

<210> SEQ ID NO 13

```
<211> LENGTH: 961
<212> TYPE: DNA
<213> ORGANISM: Arabidopsis thaliana

<400> SEQUENCE: 13
gtacgcttct cttaaaaacc cagctctatt cgctgtttag ggttttgtgt aaaatctacg      60
atgcttacct gtaatcgatg gttactcgcg tattcacaaa ttctgatggt gtagtttgag     120
tttagctagt gtcttttcccc taataatgct ttgttggtat aaccctagt gacactggtc     180
aagtcagatg cagatgagta cactagattt tacttgaatc gaggtttatg agatagttta     240
gttcttcttc aaactttgat cacccatgag gtagtttact ttctcctttg atggttgtaa     300
ccaatggagc tctcgaattt actaattctg atgtgtaatt ctgttaatag acctagaaat     360
gcattgtggg tgttgaatct ctcttgtttg caataagtga atgataatgg tggtctagtc     420
agatggagat gatacatttt attttgcttt atagttgggt gtatgagaat gcttagttct     480
tctgggagtg agtttagcac atgattatat atgagatagt ttactttagt ttccctcttt     540
atcattgtgg acctctcttg ttaacaaatc ctgaggctta attctgttat tagtgatagt     600
atctgaagaa gttagagttt agctgagtct taattatttt tttacctcga aatgctttgt     660
tggtaacccct cttgttagca agaactgagt gatacttgtc gagtcagatg cagatgatta     720
gatttagcac atgaaagtca ctcttatctc tttccttgta aagaaaatct ctgattttc     780
acagaacagt taccgtgtgg cttcttgttt caacttctct tttagtctga ttgatctaat     840
acaagtggtc tctgctgtta atgtttggtt tggtttcctt tttctgccat catcttgttt     900
agaatgcaat tatcaatcaa ctcactgact ggtactatct acttgtgatg acttaatgca     960
g                                                                    961

<210> SEQ ID NO 14
<211> LENGTH: 660
<212> TYPE: DNA
<213> ORGANISM: Gossypium hirsutum

<400> SEQUENCE: 14
ggcacgaggt tgctattgct gcaagggaac agccacctcc atcaactatc ggtgcttctt      60
gcgtatatgt catgttcaga cctgataaga aactatacat tggagagacg gatgatcttg     120
atggtcgaat tcgttcgcat cgttcaaagg acgggatgga aaatgcttct ttcctatatt     180
tcacagttcc agggaagagt attgctcgcc aactcgaaac tcttctaatc aaccaactct     240
taagtcaagg cttcccgatc gccaacttgg ctgacggtaa gcatcagaat tttggcacat     300
ccagtctctc atttgacggc ataaccgtag cctaacgagt taaaatgtat atcaatacgt     360
aatttatatc gaaattgaca tagaagtggc ggcagcaatt ttgcctttga tctcggttgc     420
tccacttgct ttgtacatgc atcacccttt taaccaaggg taaagttttc tagtcataat     480
ttaatagcat gtatcctatta agtccatttt gaggtttata tgaatcaggt tttcatcatt     540
aattggttaa attctgttat tagctcctct actttactaa agttgtagat ttagttctta     600
tactttaatt agattatttt tactctatac ttttcgaatg ataaaatttt agtcttcatt     660

<210> SEQ ID NO 15
<211> LENGTH: 28
<212> TYPE: DNA
<213> ORGANISM: Artificial
<220> FEATURE:
<223> OTHER INFORMATION: synthetic

<400> SEQUENCE: 15
```
ggttgaggag cctgaatctc tgaagaac                                              28

<210> SEQ ID NO 16
<211> LENGTH: 28
<212> TYPE: DNA
<213> ORGANISM: Artificial
<220> FEATURE:
<223> OTHER INFORMATION: synthetic

<400> SEQUENCE: 16
ctcgccagag attcgagata taccgaag                                              28

<210> SEQ ID NO 17
<211> LENGTH: 27
<212> TYPE: DNA
<213> ORGANISM: Artificial
<220> FEATURE:
<223> OTHER INFORMATION: synthetic

<400> SEQUENCE: 17
tttttaggaa ttattgagta ttattga                                               27

<210> SEQ ID NO 18
<211> LENGTH: 24
<212> TYPE: DNA
<213> ORGANISM: Artificial
<220> FEATURE:
<223> OTHER INFORMATION: synthetic

<400> SEQUENCE: 18
aaataaaaat catacccaca tccc                                                  24

<210> SEQ ID NO 19
<211> LENGTH: 26
<212> TYPE: DNA
<213> ORGANISM: Artificial
<220> FEATURE:
<223> OTHER INFORMATION: synthetic

<400> SEQUENCE: 19
tgttgaatta ttaagatatt taagat                                                26

<210> SEQ ID NO 20
<211> LENGTH: 25
<212> TYPE: DNA
<213> ORGANISM: Artificial
<220> FEATURE:
<223> OTHER INFORMATION: synthetic

<400> SEQUENCE: 20
tcaaccaata aaaattacca tctac                                                 25

<210> SEQ ID NO 21
<211> LENGTH: 30
<212> TYPE: DNA
<213> ORGANISM: Artificial
<220> FEATURE:
<223> OTHER INFORMATION: synthetic

<400> SEQUENCE: 21
taagtttttt ttaagagttt gtatttgtat                                            30

<210> SEQ ID NO 22
<211> LENGTH: 25
<212> TYPE: DNA

```
<213> ORGANISM: Artificial
<220> FEATURE:
<223> OTHER INFORMATION: synthetic

<400> SEQUENCE: 22
taaaaataat caaaacctaa cttac                                           25

<210> SEQ ID NO 23
<211> LENGTH: 25
<212> TYPE: DNA
<213> ORGANISM: Artificial
<220> FEATURE:
<223> OTHER INFORMATION: synthetic

<400> SEQUENCE: 23
attgtttatt aaatgttttt tagtt                                           25

<210> SEQ ID NO 24
<211> LENGTH: 24
<212> TYPE: DNA
<213> ORGANISM: Artificial
<220> FEATURE:
<223> OTHER INFORMATION: synthetic

<400> SEQUENCE: 24
ctaacaattc ccaaaaccct tatc                                            24

<210> SEQ ID NO 25
<211> LENGTH: 24
<212> TYPE: DNA
<213> ORGANISM: Artificial
<220> FEATURE:
<223> OTHER INFORMATION: synthetic

<400> SEQUENCE: 25
gtgtactcat ctggatctgt attg                                            24

<210> SEQ ID NO 26
<211> LENGTH: 25
<212> TYPE: DNA
<213> ORGANISM: Artificial
<220> FEATURE:
<223> OTHER INFORMATION: synthetic

<400> SEQUENCE: 26
ggttgaggag cctgaatctc tgaac                                           25

<210> SEQ ID NO 27
<211> LENGTH: 250
<212> TYPE: DNA
<213> ORGANISM: Arabidopsis thaliana

<400> SEQUENCE: 27
cagttcccaa agcccttgtc aaacatcgtc caacacgtat caccactcga caacataaag     60
acagacggtt caactacacc gcgctcgcgc ctcaccttga aaatctcatc actctttagc    120
aaacgcgaaa acccttatt aagtaacttt agtttccaat actcgaaacg cggcacgcgt    180
gcgagtatct cgacctctaa ctcgtatacg agctgaggaa catttagtaa acaataatct    240
gcatccttag                                                          250

<210> SEQ ID NO 28
<211> LENGTH: 234
<212> TYPE: DNA
<213> ORGANISM: Arabidopsis thaliana
```

<400> SEQUENCE: 28
caattcccaa aacccttatc aaacatcatc caacacatat caccactcga caacataaaa    60
acaaacaatt caactacacc acactcacac ctcaccttaa aaatctcatc attctttaac   120
aaacacaaaa accccttatt aaataacttt aatttccaat actcaaaaca caacacacat   180
acaaatatct caacctctaa ctcatataca aactaaaaaa catttaataa acaa          234

<210> SEQ ID NO 29
<211> LENGTH: 234
<212> TYPE: DNA
<213> ORGANISM: Arabidopsis thaliana

<400> SEQUENCE: 29
caattcccaa aacccttatc aaacatcatc caacacatat caccactcaa caacataaaa    60
acaaacaatt caactacacc acactcacac ctcaccttaa aaatctcatc actctttaac   120
aaacacaaaa accccttatt aaataacttt aatttccaat actcgaaaca cgacacacat   180
acaaatatct caacctctaa ctcatataca aactaaaaaa catttaataa acaa          234

<210> SEQ ID NO 30
<211> LENGTH: 233
<212> TYPE: DNA
<213> ORGANISM: Arabidopsis thaliana

<400> SEQUENCE: 30
caattcccaa aacccttatc aaacatcatc caacacatat caccactcaa caacataaaa    60
acaaacaatt caactacacc acactcacac ctcaccttaa aaatctcatc actctttaac   120
aaacacaaaa accccttatt aaataacttt aatttccaat actcaaaaca caacacacat   180
acaaatatct caacctctaa tcatatacaa actaaaaaac atttaataaa caa           233

<210> SEQ ID NO 31
<211> LENGTH: 234
<212> TYPE: DNA
<213> ORGANISM: Arabidopsis thaliana

<400> SEQUENCE: 31
caattcccaa aacccttatc aaacatcatc caacacatat caccactcga caacataaaa    60
acaaacaatt caactacacc acattcacac ctcaccttaa aaatctcatc actctttaac   120
aaacacaaaa accccttatt aaataacttt aatttccaat actcaaaaca caacacacat   180
acaaatatct caacctctaa ctcatataca aactaaaaaa catttaataa acaa          234

<210> SEQ ID NO 32
<211> LENGTH: 234
<212> TYPE: DNA
<213> ORGANISM: Arabidopsis thaliana

<400> SEQUENCE: 32
caattcccag gacccttatc aaacatcatc caacacatat caccactcaa caacataaaa    60
acaaacaatt caactacacc acactcacac ctcaccttaa aaatctcatc actctttaac   120
aaacacaaaa accccttatt aaataacttt aatttccaat actcaaaaca caacacacat   180
acaaatatct caacctctaa ctcatataca aactaaaaaa catttaataa acaa          234

<210> SEQ ID NO 33
<211> LENGTH: 234
<212> TYPE: DNA

<213> ORGANISM: Arabidopsis thaliana

<400> SEQUENCE: 33

| caattcccaa aacccttatc aaacatcatc caacacatat caccactcga caacataaaa | 60 |
| acaaacaatt caactacacc acactcacac ctcaccttaa aaatctcatc actctttaac | 120 |
| aaacacaaaa accccttatt aaataacttt aatttccaat actcaaaaca caacacacat | 180 |
| acaaatatct caacctctaa ctcatataca aactaaaaaa catttaataa acaa | 234 |

<210> SEQ ID NO 34
<211> LENGTH: 234
<212> TYPE: DNA
<213> ORGANISM: Arabidopsis thaliana
<220> FEATURE:
<221> NAME/KEY: misc_feature
<222> LOCATION: (98)..(98)
<223> OTHER INFORMATION: n is a, c, g, or t

<400> SEQUENCE: 34

| caattcccaa aacccttatc aaacatcatc caacacatat caccactcaa caacataaaa | 60 |
| acaaacaatt caactacacc acactcacac ctcacctnaa aaatctcatc actctttaac | 120 |
| aaacacaaaa accccttatt aaataacttt aatttccaat actcaaaaca caacacacat | 180 |
| acaaatatct caacctctaa ctcatataca aactaaaaaa catttaataa acaa | 234 |

<210> SEQ ID NO 35
<211> LENGTH: 234
<212> TYPE: DNA
<213> ORGANISM: Arabidopsis thaliana

<400> SEQUENCE: 35

| caattcccaa aacccttatc aaacatcatc caacacatat caccactcga caacataaaa | 60 |
| acaaacaatt caactacacc acactcacac ctcaccttaa aaatctcatc actctttaac | 120 |
| aaacacgaaa accccttatt aaataacttt aatttccaat actcaaaaca caacacacat | 180 |
| acaaatatct caacctctaa ctcatataca aactaaaaaa catttaataa acaa | 234 |

<210> SEQ ID NO 36
<211> LENGTH: 234
<212> TYPE: DNA
<213> ORGANISM: Arabidopsis thaliana

<400> SEQUENCE: 36

| caattcccaa aacccttatc aaacatcatc caacacatat caccactcga caacataaaa | 60 |
| acaaacaatt caactacacc acactcacac ctcaccttaa aaatctcatc actctttaac | 120 |
| aaacacaaaa accccttatt aaataacttt aatttccaat actcaaaaca caacacacat | 180 |
| acaaatatct caacctctaa ctcatataca aactaaaaaa catttaataa acaa | 234 |

<210> SEQ ID NO 37
<211> LENGTH: 234
<212> TYPE: DNA
<213> ORGANISM: Arabidopsis thaliana

<400> SEQUENCE: 37

| caattcccaa aacccttatc aaacatcatc caacacatat caccactcga caacataaaa | 60 |
| acaaacaatt caactacacc acactcacac ctcaccttaa aaatctcatc actctttaac | 120 |
| aaacacaaaa accccttatt aaataacttt aatttccaat actcaaaaca caacacacat | 180 |
| acaaatatct caacctctaa ctcatataca aactaaaaaa catttaataa acaa | 234 |

<210> SEQ ID NO 38
<211> LENGTH: 234
<212> TYPE: DNA
<213> ORGANISM: Arabidopsis thaliana

<400> SEQUENCE: 38

```
caattcccaa aacccttatc aaacatcatc caacacatat caccactcaa caacataaaa      60
acaaacaatt caactacacc acactcacac ctcaccttaa aaatctcatc actctttaac     120
aaacacaaaa acccttatt aaataacttt aatttccaat actcaaaaca caacacacat      180
acaaatatct caacctctaa ctcatataca aactaaaaaa catttaataa acaa            234
```

<210> SEQ ID NO 39
<211> LENGTH: 234
<212> TYPE: DNA
<213> ORGANISM: Arabidopsis thaliana

<400> SEQUENCE: 39

```
caattcccaa aacccttatc aaacatcatc caacacatat caccactcga caacataaaa      60
acaaacaatt caactacacc acactcacac ctcaccttaa aaatctcatc actctttaac     120
aaacacaaaa acccttatt aaataacttt aatttccaat actcaaaaca caacacacat      180
acaaatatct caacctctaa ctcatataca aactaaaaaa catttaataa acaa            234
```

<210> SEQ ID NO 40
<211> LENGTH: 234
<212> TYPE: DNA
<213> ORGANISM: Arabidopsis thaliana

<400> SEQUENCE: 40

```
caattcccaa aacccttatc aaacatcgtc caacacgtat caccactcga caacataaaa      60
acaaacggtt caactacacc gcactcgcgc ctcaccttaa aaatctcatc gctctttaac     120
aaacacgaaa acccttatt aaataacttt aatttccaat actcgaaacg cgacacgcgt      180
acgaatatct cgacctctaa ctcgtatacg aactaaaaaa catttaataa acaa            234
```

<210> SEQ ID NO 41
<211> LENGTH: 234
<212> TYPE: DNA
<213> ORGANISM: Arabidopsis thaliana

<400> SEQUENCE: 41

```
caattcccaa aacccttatc aaacatcgtc caacacgtat caccactcga caacataaaa      60
acaaacgatt caactacacc gcactcgcgc ctcaccttaa aaatctcatc actctttaac     120
aaacgcggaa acccttatt aaataacttt aatttccaat actcaaaacg cgacacgcgt      180
acaaatatct cgacctctaa ctcatatacg aactaaaaaa catttaataa acaa            234
```

<210> SEQ ID NO 42
<211> LENGTH: 234
<212> TYPE: DNA
<213> ORGANISM: Arabidopsis thaliana

<400> SEQUENCE: 42

```
caattcccaa aacccttatc aaacatcgtc caacacgtat caccactcga caacataaaa      60
acaaacgatt caactacacc gcgctcgcgc ctcaccttaa aaatctcatc actctttaac     120
aaacgcgaaa acccttatt aaataactct aatttccaat actcgaaaca cgacacgcat      180
```

```
acgaatatct caacctctaa ctcgtatacg aactaaaaaa catttaataa acaa          234

<210> SEQ ID NO 43
<211> LENGTH: 234
<212> TYPE: DNA
<213> ORGANISM: Arabidopsis thaliana

<400> SEQUENCE: 43
caattcccaa aacccttatc aaacatcgtc caacacgtat caccactcga caacataaaa    60
acaaacgatt caactacacc gcgctcgcgc ctcaccttaa aaatctcatc actctttaac   120
aaacacgaaa acccctttatt aaataacttt aatttccaat actcgaaacg cgacacgcgt   180
acgaatatct cgacctctaa ctcgtatacg aactaaaaaa catttaataa acaa          234

<210> SEQ ID NO 44
<211> LENGTH: 234
<212> TYPE: DNA
<213> ORGANISM: Arabidopsis thaliana

<400> SEQUENCE: 44
caattcccaa aacccttatc aaacatcgtc caacacatat caccactcga caacataaaa    60
acaaacgatt caactacacc gcgctcgcgc ctcaccttaa aaatctcatc actctttaac   120
aaacgcgaaa acccctttatt aaataacttt aatttccaat actcgaaacg cgacacacgt   180
acgaatatct cgacctctaa ctcgtatacg aactaaaaaa catttaataa acaa          234

<210> SEQ ID NO 45
<211> LENGTH: 234
<212> TYPE: DNA
<213> ORGANISM: Arabidopsis thaliana

<400> SEQUENCE: 45
caattcccaa aacccttatc aaacatcgtc caacacgtat caccactcga caacataaaa    60
acaaacaatt caactacacc gcgctcgcgc ctcaccttaa aaatctcatc actctttaac   120
aaacgcgaaa acccctttatt aaataacttt aatttccaat actcgaaaca cgacacgcgt   180
acgaatatct cgacctctaa ctcgtatacg aactaaaaaa catttaataa acaa          234

<210> SEQ ID NO 46
<211> LENGTH: 234
<212> TYPE: DNA
<213> ORGANISM: Arabidopsis thaliana

<400> SEQUENCE: 46
caattcccaa aacccttatc aaacatcgtc caacacgtat caccactcga caacataaaa    60
acaaacgatt caactacacc gcgctcgcgc ctcaccttaa aaatctcatc actctttaac   120
aaacgcgaaa acccctttatt aaataacttt aatttccaat actcgaaacg cgacacacgt   180
acaaatatct cgacctctaa ctcgtatacg aactaaaaaa catttaataa acaa          234

<210> SEQ ID NO 47
<211> LENGTH: 234
<212> TYPE: DNA
<213> ORGANISM: Arabidopsis thaliana

<400> SEQUENCE: 47
caattcccaa aacccttatc aaacatcgtc caacacgtat caccactcga caacataaaa    60
acaaacgatt caactacacc gcgcttgcgc ctcaccttaa aaatctcatc actctttaac   120
aaacgcgaaa acccctttatt aaataacttt aatttccaat actcgaaacg cgacacgcgt   180
```

```
acgaatatct cgacctctaa ctcatatacg aactaaaaaa catttaataa acaa        234
```

<210> SEQ ID NO 48
<211> LENGTH: 234
<212> TYPE: DNA
<213> ORGANISM: Arabidopsis thaliana

<400> SEQUENCE: 48

```
caattcccaa aacccttatc aaacatcgtc caacacgtat caccactcga caacataaaa         60
acaaacgatt caactacacc gcgctcgcgc ctcaccttaa aaatctcatc actctttaac        120
aaacgcgaaa accccttatt aaataacttt aatttccaat actcgaaacg cgacacgcgt        180
acgaatatct cgacctctaa ctcgtatacg aactaaaaaa catttaataa acaa             234
```

<210> SEQ ID NO 49
<211> LENGTH: 234
<212> TYPE: DNA
<213> ORGANISM: Arabidopsis thaliana

<400> SEQUENCE: 49

```
caattcccaa aacccttatc aaacatcgtc caacacatat caccactcga caacataaaa         60
acaaacgatt caactacacc gcgctcgcgc ctcaccttaa aaatctcatc actctttgac        120
aaacacaaaa accccttatt aaataacttt aatttccaat actcaaaacg cgacacgcgt        180
acgaatatct caacctctaa ctcgtatacg aactaaaaaa catttaataa acaa             234
```

<210> SEQ ID NO 50
<211> LENGTH: 234
<212> TYPE: DNA
<213> ORGANISM: Arabidopsis thaliana

<400> SEQUENCE: 50

```
caattcccaa aacccttatc aaacatcgtc caacacgtat caccactcga caacataaaa         60
acaaacgatt caactacacc gcactcgcgc ctcaccttaa aaatctcatc actctttaac        120
aaacgcgaaa accccttatt aaataacttt aatttccaat actcgaaacg cgacacgcgt        180
acgaatatct cgacctctaa ctcatataca aactaaaaaa catttaataa acaa             234
```

<210> SEQ ID NO 51
<211> LENGTH: 3369
<212> TYPE: DNA
<213> ORGANISM: Brassica rapa

<400> SEQUENCE: 51

```
atgcactgga ttgccaccag aaacgccgtc gtttcgctcc ctagatggcg ttccttcgcc         60
ttcctcttcc gctcgccatt tcgcacccac tcttccctca aaccctcccc acttcttcta        120
cttaatacaa ggtactctga gaggagatac tgtttaggag atggaaagtc tgtgaaagga        180
atcactacgg cttcttctaa gaaagttaag accaagtcta ctgatgttct cactgacaaa        240
gatctctctc atttgctctg gtggaaggag agattgcaga catgtaagaa accatctact        300
cttcaactta tcgaaaggct tatgtacacc aatctacttg gtttggaccc cagcttgagg        360
aatggaagtc ttaaagacgg aaacctcaac tgggagatgt gcagtttaa gtcaaggttt        420
ccacgtgaag ttttgctctg cagagttgga gacttctatg aggctattgg aatagatgct        480
tgtatactcg ttgaatatgc tggtttaaat ccttttggtg gtcttcgttc agatagtgtt        540
ccaaaggctg gctgcccagt tgtgaatctt agacaaactt ggatgaccct aacacgcaat        600
```

-continued

```
ggttttcag tgtgtattgt ggaagaaatt caggggccaa caccagcacg ttctcgtaaa        660
ggtcgattca tttcagggca tgcacatcca ggaagtcctt atgtctatgg gctcgttggt       720
gttgaccatg atcttgactt tccggagcct atgcctgtgg ttgggatatc tcgttcagca       780
aggggctact gtatgatatc tatcttcgag actatgaaag catattcact agatgatggt       840
ctaacagaag aagctctggt caccaagctc cgcacccgtc gctgtcatca tcttttctta       900
catgcatcat tgagacacaa tgcatcagga acatgccggt ggggagagtt tggagaaggg       960
ggtctcctct ggggagaatg tagtggcaga aattttgaat ggtttgaagg agatactctt      1020
tccgagctct taacaaaggt cagagatgtt tatggtcttg atgatgaagt ttcctttaga      1080
aatgtcaatg tacctttaga aaaccggcca cgtcctttgc atcttggaac ggctacacaa      1140
attggtgcct tacctactga aggaataccct tgtttgttga aggtgctact tccatctacg     1200
tgcagtggcc tgccttcttt gtatctccgg gatcttcttc taaaccctcc tgcttatgat      1260
attgctctga aaatccaaga aacgtgcaag ctcatgagca caataacatg ctcagttccg      1320
gagtttacct gtgtttcatc tgctaagctt gtgaagcttt tgaacagcg ggaagccaac       1380
tacattgagt tctgccggat aaaaaatgtg cttgatgaag tattacacat gcacagacat      1440
cctgagcttg tggaaatact gaagttattg atggaaccta cttgggtggc tactggtttg     1500
aagattgact ttgaaacttt tgtcaatgaa tgtcattggg cttctgattc aattggtgaa     1560
atgatctcat tagatgacga tgaaagtcat cagaacgtta gtaaatgtgc taatgtcccg     1620
aacgagttct tttacgatat ggagtcttca tggcgtggtc gcgttaaggg aatccatata     1680
gaggaagaaa tcacacaagt ggccaaatcg gcagaggctt tatctttagc ggtaactgaa     1740
gatttccacc ctattatatc aagaatcaag gctatggctg catcacttgg tggctcaaag     1800
ggagaaattg tgtatgcaaa agaacatgag tctgtttggt tcaaagggaa acggtttacc     1860
ccatctgtat ggggtggtac tgctggggaa gaacaaatta aacagctgaa acctgctttt    1920
gactccaaag ggaaaaaggt tggagaagaa tggtttacaa ctcaaaaggt ggaaactgct    1980
ttagtcagat atcatgaagc tagtgagaac gcaaatgccc gggtcttgga gcttttgagg    2040
gaattatctg ctaaacttca acaaaaata aacgttcttg tatttgcatc tatgcttctc     2100
gtcattgcaa aagcattatt ttctcatgct tgtgaaggga gaagacgaaa gtgggttttt     2160
ccaactcttg ttggtttcag tacagatgag gccgcaaatc cattagatgg tggtgccact    2220
cgaatgaagc tgactgggct atcaccttat tggtttgatg tagcttctgg aactgctgtt    2280
cacaatacgg tcgacatgca atcactgttt cttctaaccg gacctaacgg tggtggtaaa    2340
tcaagtttgc tcagatcgat atgcgcagct gctttgcttg gaatctgtgg ttttatggtt    2400
ccagctgaat cagcttatat ccctcacttc gattccatca tgcttcatat gaaatcttat    2460
gacagtcctg tagatgggaa gagttctttt caggtggaaa tgtcggagat acggtctatt    2520
gtaagccagg ctacttcaag aagcctagtg cttatagatg agatctgcag agggacagag    2580
acagctaaag gcacatgtat tgctggtagt gtgatcgaga gtcttgacgc aagtggttgc    2640
ttgggtattg tgtctacaca tctccatgga atcttcgatt tgcctcttac ggccaaaaac    2700
gtcacgtata aagcaatggg agcagagaat gtggaagggc aaacaaaacc aacatggaaa    2760
ctgacagatg gagtttgcag agagagtctt gcgtttgaaa cagctaagag agaaggtgtt    2820
ccggagacaa ttatccaaag agccgaagct ctttacatct ccgtttatgc caaagacgca    2880
tcgtttgggg ttgtcaggcc aaacaaaacg gagacttcat cggacaatga gatcagcaaa    2940
ccagtcaggt ctgagagaag cttggagaag gacttggcaa aagctatcct taagatttgt    3000
```

-continued

```
gggataaaga tgaatgagcc tgtaggttta aatgtctttt caataggtgc tcgagagctt    3060
ccacctccat ctacagttgg ttcatcatgc gtgtatgtga tgaagagacc agataagaga    3120
ttgtacattg gacagacgga tgatcttgaa ggaagaatac gtgcgcatag ggcaaaggaa    3180
ggactgcaag ggtcaagttt cctataccct gtggtacaag gtaagagtat ggcttgtcag    3240
ctagagaccc ttttgattaa ccagctccat gagcaaggct actctctagc taacttagcc    3300
gatggaaagc accgcaattt tgggacgtca tcaagcttga ctgcgtcaga tgtagtcagt    3360
atctcctag                                                           3369
```

<210> SEQ ID NO 52
<211> LENGTH: 3768
<212> TYPE: DNA
<213> ORGANISM: Triticum aestivum
<220> FEATURE:
<221> NAME/KEY: misc_feature
<222> LOCATION: (3557)..(3557)
<223> OTHER INFORMATION: n is a, c, g, or t

<400> SEQUENCE: 52

```
actcagatta gaaatgctga gagagcctta cctggtaaaa atgaagatac ctcaaatgag     60
cagccaagtg catcttcccc tgtacggtac aacggcaaat atagcagagg aactgtgtta    120
tttgcagaac atagcacgga taccactccg ccacaggagc cactgaagtt ttctgcaagg    180
tcttccacag atgaatttgt taaagcaagc acgctgttcc ctgaacttgg ttcagatcaa    240
actctgcttc aagagtgtcc gaagaagtta tcctcagagt gccccagcaa ccagtacgtt    300
caagctaatt cagtgtttga agcatttgat gtacaaactc cgtcccagga tccgttaaag    360
agaatctttt ctgggccttt tcatggagca gatacacctt taccagagta tcgttcatat    420
ccaattcctt tgcagcatcc atcgaaaaat ttgtcatcgg gctcttctag tggtgaatac    480
cttagagcag tgacaccgct tggacttgat tcgaatgata ctcccacagc aaaacactca    540
aagaagctat tctctgggtc ttcagaccat tcatacatta agcaactaa tttgttttccg    600
gaatttgatt caaatggaac tccgctgcag aaccactcga ataagttctc agtatctatg    660
aatggtaagc atattggagc agctgctaca ctgtttccag aacttgattc tgttcttctg    720
aaaccagaaa ctccagtgac acgagcagtg gctcctcgcg ggaagagagt tcaacaggat    780
caacgcatga ctgccaataa cagccagtct cctttgtggg gttcaaataa gaaggtgaaa    840
tcagctcatt gttctccacc tgggaaaatg gttcatgatg aaatggctga aagtgcacgt    900
agtaaatttg aatggctgaa tcctttgaat atcaggggatg caaataaaag gcggccagat    960
gacccacttt atgacaagag aactctttttt attccacctg atgcactgag aaagatgtca   1020
acatctcaaa agcaatactg gtctattaag tgcaaatata tggatgttct cctcttcttc   1080
aaagtgggga aattttatga gctctatgaa gtagatgctg agatcggcca aaaggaactt   1140
gattggaaaa tgactattag tggggttgga aaatgccgac aggttggtat ttcagagagt   1200
gggattgacg atgctgttga aaagctttta gctcgggggat ataaagttgg aaggatagaa   1260
caaatggaat ctgcagcaca ggcgaaatct agaggaccaa attcagttat cgaaagaaag   1320
ttagctcatg tatccacacc gtcaactgca gctgacagca atatagggcc tgatgctgtt   1380
catcttcttg cattgaaaga ggttactcta gcttctaatg ttctcggct tacggatttt   1440
gcttttctag attatgctgc acttaaaatc tgggttggtt cacttcaaga tgatgattcg   1500
tctgcagctt ggggggcttt gctggtgcag gtttccccga gggagataat ctatgaatcc   1560
```

-continued

```
tcaggcctct caagagaaag tcgtaaatca atgataaaat atgcctcagc aggctctgtg    1620
aaaatgcaac tgaccccact acctgggaca gatttctctg atgcctcaca aattcaaatg    1680
ctagtacatt ctaaaggata ctttaaagca tcaacagatt cttggttatc tgcattggat    1740
tattcagtga atcgagatgc agttatcttt gcacttggtg gacttattgg tcatttgact    1800
agacttatgc tagacgatgc tctaaaaaat ggggaagtct taccttacaa tgtgtaccaa    1860
acttgtttaa ggatggatgg tcagactctt gtgaacctgg agattttcgg caataacttt    1920
gatggtggct catcaggtac tctgtacaag cacctcaatc actgcataac cgcatctggt    1980
aagcggcttt taagaagatg gatatgccat ccactaaaag atgtcgatgc tataaataga    2040
aggcttgatg ttgttgaggg tttcatccag cattgtgggg taggctctat tacactttat    2100
tatctccgga aaattcctga ccttgagagg ttacttgggc gaatcagatc tactgttggg    2160
ctaacatctg ctgtcctgtt gccttttgtt ggtgaaaaga tattaaagag gcggattaaa    2220
atgtttggca tgcttatcaa gggcctccgg gttggaattg acttattaag tgccttgcgt    2280
agagatgacc atggcatccc agcgctgtca aaatcagttg atattccaac cctgagttct    2340
cttgatgaat tagttcatca gtttgaggag gatatacaca atgactttga acagtaccag    2400
gatcatgata tcaaagacgg tgatgctacc accttggcta atttagtgga acattttgtt    2460
ggaaaagcta ccgaatggtc tttggtaatc aatgccatca gcactgttga tgtccttagg    2520
tcctttgcag caatggcatt gtcatcattt ggcaccatgt gcagaccatg tattctgttg    2580
aaagacaaat cgcctatact tcggatgaag ggtctatggc atccatatgc ttttgcagaa    2640
agtggaactg gcttgtacc aaacgatttg tctcttggcc aggatttatc gggtcataat    2700
cgctttgcat tgttgttgac tggtccaaat atgggaggaa atctacaat aatgcgcgct    2760 acctgcttgg ctatcgtgct tgcccagctt ggctgttatg tccctgcat atcatgtgaa    2820 ttgaccttg cagactccat cttt acacgg ctaggcgcaa cggatcggat tatgtctgga    2880
gaaagtactt tcttgtcga atgtagtgag actgcatctg ttcttcagaa tgcaactgag    2940
gattctcttg tcttgcttga tgaacttggc agaggaacta gcacatttga tggatacgcg    3000
attgcatatg cagtattccg ccacctggtg gaacaggtgc gatgccgtct gctctttgcc    3060
acccactacc acccctctca caaggagttc gcctcccacc ccacgtgag cctccagcac    3120 atggcctgca tgctgaggcc aaggagcggc ggcaacggcg agatggagct caccttcctc    3180
taccgtcttg tgtcaggcgc ctctccggag agctacggcc tgcaggtcgc cacgatggcg    3240
gggatcccaa agtccatagt ggagaaggcg gcggtcgcgg gcgagatgat gaagtcgagg    3300
atcgcaggga acttcaggtc gagcgaaggg cgagcggagt tctccaccct ccacgaggac    3360
tggctgcaga cgatcctggc gatcggcggc gtcaaggacg cgcacctgga cgaggacacc    3420
atggacacga tgttctgcgt cgcccaggag ctcaagtctc atttcaggaa aggaggaagc    3480
tgagcgctga gaagtcgcca ccggtaatta tgcgtggcac cattagatgc aggtagtctg    3540
aaggaggaag atgagcnccg agaaagtcgc cgctcaccat taatcatcag tgttttaatc    3600
cgtcccagtc gacggctttg tatatagtta cctcgcgttt gtaatcacgc aagcgcacct    3660
gggcctgagt tcatctgaac tgtcaaaaac ttcatctcgt agtttgtaat cacatgcaca    3720
ttcctagtga ttagtcgaga gtttcaaaaa aaaaaaaaa aaaaaaaa                 3768
```